(12) United States Patent
Zhang

(10) Patent No.: US 10,828,156 B2
(45) Date of Patent: *Nov. 10, 2020

(54) DEVICES AND METHODS FOR DELIVERY OF VALVE PROSTHESES

(71) Applicant: Suzhou Jiecheng Medical Technology Co., Ltd., Jiangsu (CN)

(72) Inventor: Ji Zhang, Burnaby (CA)

(73) Assignee: JC Medical, Inc., Burlingame, CA (US)

(*) Notice: Subject to any disclaimer, the term of this patent is extended or adjusted under 35 U.S.C. 154(b) by 235 days.

This patent is subject to a terminal disclaimer.

(21) Appl. No.: 15/913,843

(22) Filed: Mar. 6, 2018

(65) Prior Publication Data

US 2018/0193143 A1 Jul. 12, 2018

Related U.S. Application Data

(63) Continuation of application No. 14/033,054, filed on Sep. 20, 2013, now Pat. No. 9,907,650, which is a (Continued)

(51) Int. Cl.
*A61F 2/24* (2006.01)
*A61F 2/966* (2013.01)
*A61F 2/95* (2013.01)

(52) U.S. Cl.
CPC .......... *A61F 2/2427* (2013.01); *A61F 2/2418* (2013.01); *A61F 2/2436* (2013.01);
(Continued)

(58) Field of Classification Search
CPC ........ A61F 2/24; A61F 2/2409; A61F 2/2418; A61F 2/2427–2439; A61F 2250/0063
See application file for complete search history.

(56) References Cited

U.S. PATENT DOCUMENTS 4,705,516 A * 11/1987 Barone ................. A61F 2/2409
623/2.39
5,800,508 A * 9/1998 Goicoechea ............ A61F 2/954
623/1.15
(Continued)

FOREIGN PATENT DOCUMENTS

WO WO-2004/019825 A1 3/2004
WO WO 2005/002466 1/2005
(Continued)

OTHER PUBLICATIONS

International Search Report and Written Opinion from related PCT Patent Application No. PCT/US2010/028843, dated Jul. 19, 2010, 18 pages.

*Primary Examiner* — Tan-Uyen T Ho
*Assistant Examiner* — Charles M Wei
(74) *Attorney, Agent, or Firm* — Nathan S. Smith; Sujohn Das; Morgan, Lewis & Bockius LLP

(57) ABSTRACT

Valve prostheses, implantation devices, and methods for use are provided. The devices may be used for transcatheter delivery of an aortic valve prosthesis or transapical delivery of a mitral valve prosthesis. The implantation device can utilize movable claspers for both positioning and anchoring the valve prosthesis, reducing the extent of imaging needed during the implantation procedure.

15 Claims, 52 Drawing Sheets

Related U.S. Application Data continuation of application No. 12/748,059, filed on Mar. 26, 2010, now Pat. No. 8,540,767.

(60) Provisional application No. 61/228,423, filed on Jul. 24, 2009, provisional application No. 61/211,431, filed on Mar. 30, 2009, provisional application No. 61/211,433, filed on Mar. 30, 2009, provisional application No. 61/211,430, filed on Mar. 30, 2009, provisional application No. 61/211,432, filed on Mar. 30, 2009.

(52) U.S. Cl.
CPC ............ *A61F 2/9517* (2020.05); *A61F 2/966* (2013.01); *A61F 2220/005* (2013.01); *A61F 2220/0016* (2013.01); *A61F 2220/0058* (2013.01); *A61F 2220/0066* (2013.01); *A61F 2230/0054* (2013.01); *A61F 2230/0067* (2013.01); *A61F 2250/006* (2013.01)

(56) References Cited

U.S. PATENT DOCUMENTS

| | | | |
|---|---|---|---|
| 6,425,916 B1 * | 7/2002 | Garrison | A61F 2/2418 623/1.26 |
| 7,018,406 B2 * | 3/2006 | Seguin | A61F 2/2418 623/2.1 |
| 7,025,780 B2 | 4/2006 | Gabbay | |
| 7,387,640 B2 | 6/2008 | Cummings | |
| 7,510,572 B2 | 3/2009 | Gabbay | |
| 7,621,948 B2 | 11/2009 | Herrmann et al. | |
| 7,789,009 B1 | 9/2010 | Brittingham | |
| 7,803,185 B2 | 9/2010 | Gabbay | |
| 7,824,443 B2 | 11/2010 | Salahieh et al. | |
| 8,052,750 B2 | 11/2011 | Tuval et al. | |
| 8,105,375 B2 | 1/2012 | Navia et al. | |
| 8,206,437 B2 | 6/2012 | Styrc et al. | |
| 8,308,798 B2 * | 11/2012 | Pintor | A61F 2/2418 623/2.18 |
| 8,313,525 B2 | 11/2012 | Tuval et al. | |
| 8,323,335 B2 | 12/2012 | Bonhoeffer et al. | |
| 8,366,767 B2 * | 2/2013 | Zhang | A61F 2/2418 623/2.11 |
| 8,366,768 B2 * | 2/2013 | Zhang | A61F 2/2418 623/2.11 |
| 8,444,689 B2 | 5/2013 | Zhang | |
| 8,540,767 B2 * | 9/2013 | Zhang | A61F 2/2418 623/2.11 |
| 9,554,903 B2 | 1/2017 | Rowe et al. | |
| 9,907,605 B2 | 3/2018 | Takashino | |
| 9,907,650 B2 | 3/2018 | Zhang | |
| 2002/0032431 A1 | 3/2002 | Kiemeneij | |
| 2003/0036791 A1 | 2/2003 | Philipp et al. | |
| 2003/0040792 A1 | 2/2003 | Gabbay | |
| 2003/0149478 A1 | 8/2003 | Figulla et al. | |
| 2004/0127912 A1 * | 7/2004 | Rabkin | A61F 2/95 606/108 |
| 2004/0260394 A1 | 12/2004 | Douk et al. | |
| 2005/0137688 A1 * | 6/2005 | Salahieh | A61F 2/2412 623/2.11 |
| 2005/0137689 A1 | 6/2005 | Salahieh | |
| 2005/0182486 A1 * | 8/2005 | Gabbay | A61F 2/2409 623/2.11 |
| 2005/0251251 A1 * | 11/2005 | Cribier | A61F 2/2412 623/2.11 |
| 2006/0052867 A1 * | 3/2006 | Revuelta | A61F 2/2418 623/2.18 |
| 2006/0058872 A1 | 3/2006 | Salahieh et al. | |
| 2006/0173524 A1 * | 8/2006 | Salahieh | A61F 2/2418 623/1.11 |
| 2006/0217802 A1 | 9/2006 | Ruiz et al. | |
| 2006/0259135 A1 | 11/2006 | Navia et al. | |
| 2006/0287719 A1 * | 12/2006 | Rowe | A61F 2/2445 623/2.18 |
| 2007/0016286 A1 | 1/2007 | Herrmann et al. | |
| 2007/0027533 A1 | 2/2007 | Douk | |
| 2007/0100440 A1 | 5/2007 | Figulla et al. | |
| 2007/0142907 A1 * | 6/2007 | Moaddeb | A61F 2/2418 623/2.11 |
| 2007/0244552 A1 | 10/2007 | Salahieh et al. | |
| 2007/0250161 A1 | 10/2007 | Dolan | |
| 2007/0260225 A1 | 11/2007 | Sakakine | |
| 2008/0071361 A1 * | 3/2008 | Tuval | A61F 2/2418 623/2.1 |
| 2008/0071363 A1 | 3/2008 | Tuval et al. | |
| 2008/0082166 A1 | 4/2008 | Styrc et al. | |
| 2008/0177381 A1 | 7/2008 | Navia et al. | |
| 2009/0054968 A1 | 2/2009 | Bonhoeffer et al. | |
| 2009/0054976 A1 | 2/2009 | Tuval et al. | |
| 2009/0132035 A1 | 5/2009 | Roth et al. | |
| 2009/0192585 A1 | 7/2009 | Bloom et al. | |
| 2009/0216310 A1 | 8/2009 | Straubinger et al. | |
| 2009/0240320 A1 * | 9/2009 | Tuval | A61F 2/2418 623/1.24 |
| 2009/0275934 A1 | 11/2009 | Baxter | |
| 2009/0287299 A1 | 11/2009 | Tabor et al. | |
| 2009/0319037 A1 * | 12/2009 | Rowe | A61F 2/2445 623/2.11 |
| 2010/0249915 A1 | 9/2010 | Zhang | |
| 2010/0274088 A1 | 10/2010 | West et al. | |
| 2014/0200649 A1 * | 7/2014 | Essinger | A61F 2/2439 623/1.12 |
| 2016/0015512 A1 * | 1/2016 | Zhang | A61F 2/2436 623/2.11 |
| 2018/0021129 A1 | 1/2018 | Peterson et al. | |
| 2018/0193141 A1 * | 7/2018 | Zhang | A61F 2/2418 |
| 2018/0193142 A1 * | 7/2018 | Zhang | A61F 2/2418 |

FOREIGN PATENT DOCUMENTS

| | | |
|---|---|---|
| WO | WO-2009/155561 A2 | 12/2009 |
| WO | WO 2010/121076 | 10/2010 |
| WO | WO 2012/095455 | 7/2012 |
| WO | WO 2014/153152 | 9/2014 |

* cited by examiner

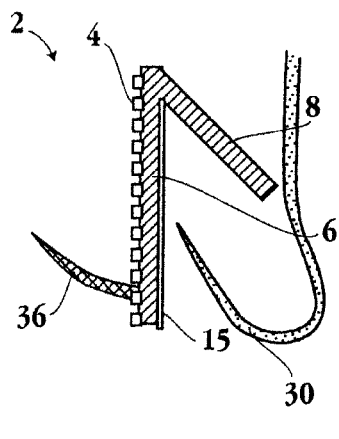
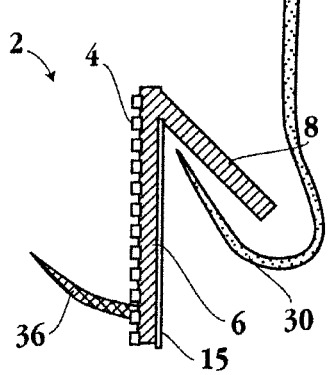
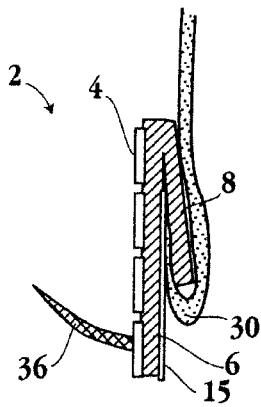
Fig. 5A        Fig. 5B        Fig. 5C
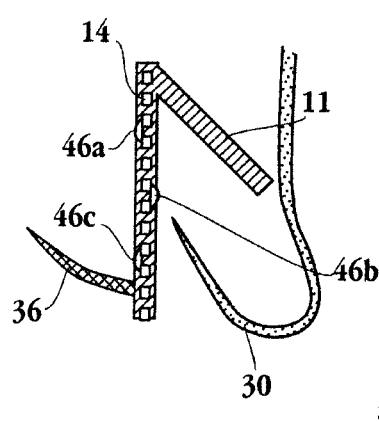
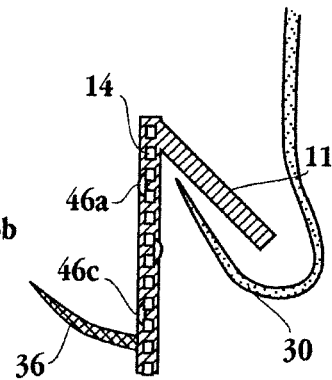
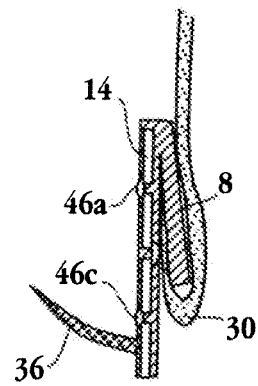
Fig. 5D        Fig. 5E        Fig. 5F

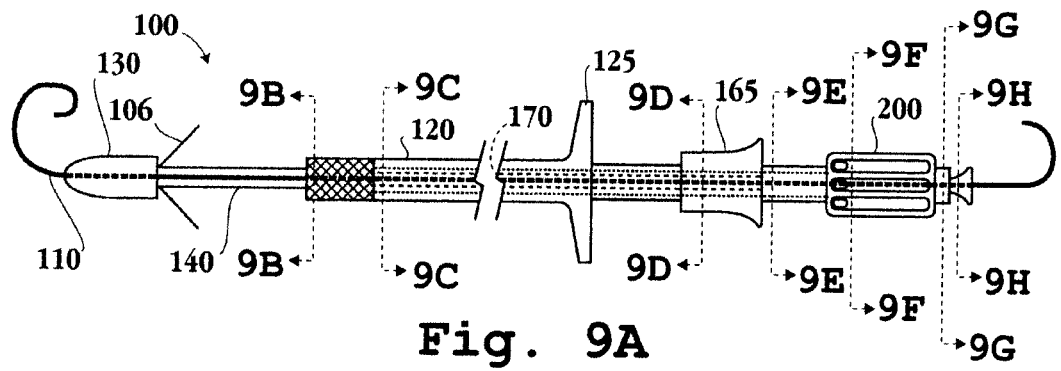
Fig. 9A
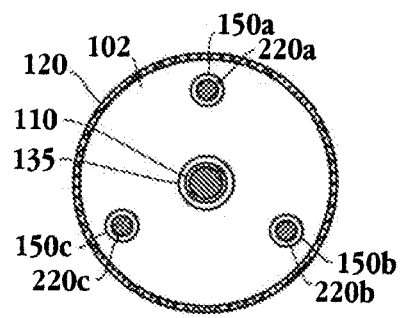
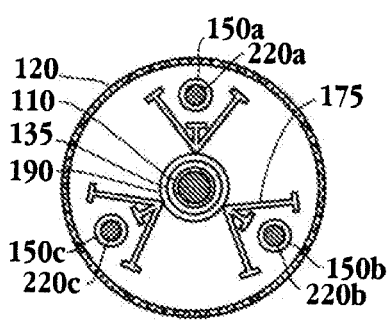
Fig. 9B  Fig. 9C
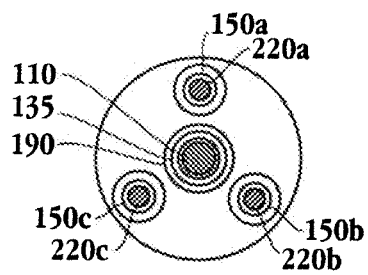
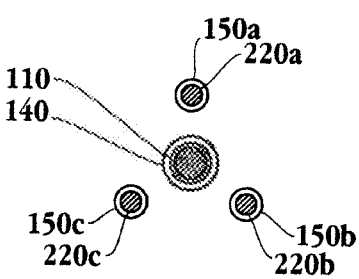
Fig. 9D  Fig. 9E
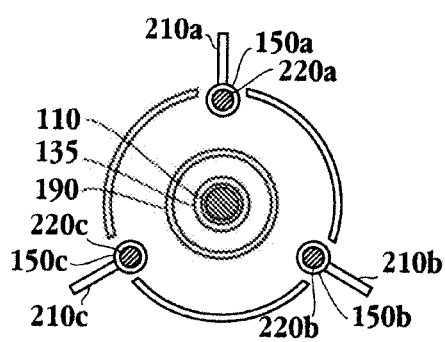
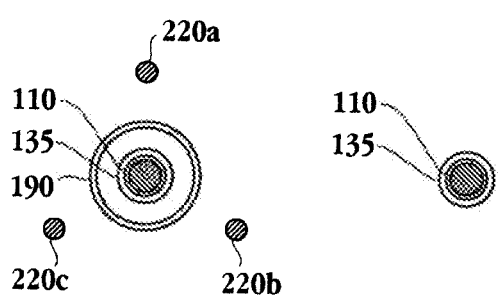
Fig. 9F  Fig. 9G  Fig. 9H

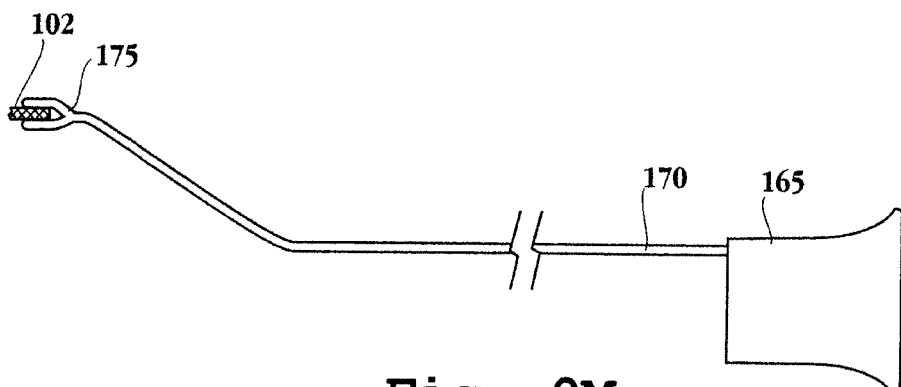
Fig. 9M
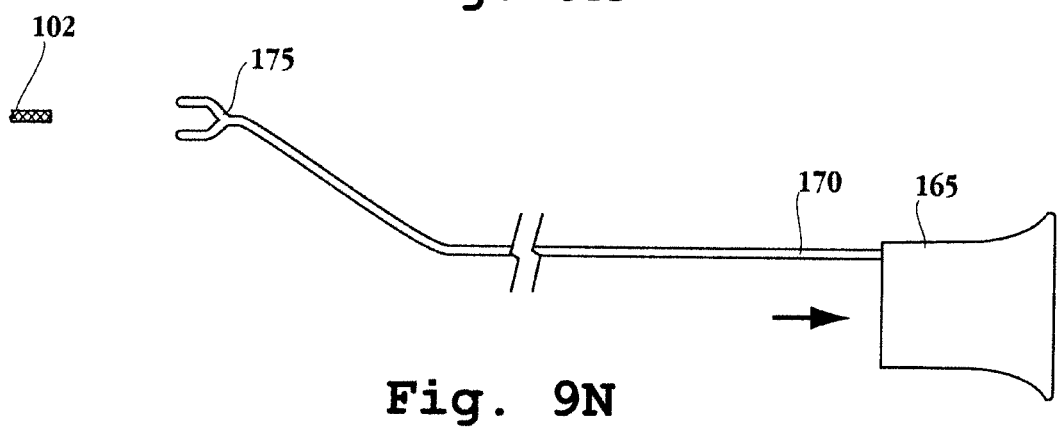
Fig. 9N
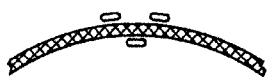  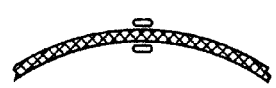
Fig. 9O    Fig. 9P    Fig. 9Q

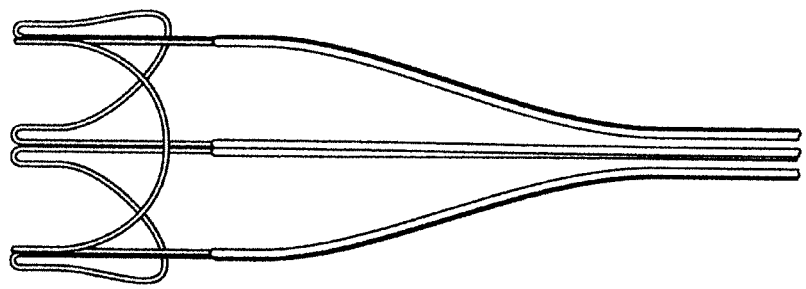
Fig. 10A
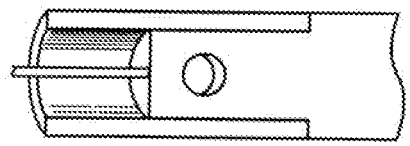 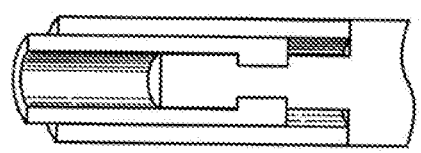
Fig. 10B            Fig. 10C

DEVICES AND METHODS FOR DELIVERY OF VALVE PROSTHESES

CROSS-REFERENCE TO RELATED APPLICATIONS

This application is a continuation of Ser. No. 14/033,054, filed Sep. 20, 2013, which is a continuation of Ser. No. 12/748,059, filed Mar. 26, 2010, now U.S. Pat. No. 8,540,767, which claims the benefit of U.S. Provisional Application No. 61/211,430, filed Mar. 30, 2009, U.S. Provisional Application No. 61/211,431, filed Mar. 30, 2009, U.S. Provisional Application No. 61/211,432, filed Mar. 30, 2009, U.S. Provisional Application No. 61/211,433, filed Mar. 30, 2009, and U.S. Provisional Application No. 61/228,423, filed Jul. 24, 2009, all of which are incorporated herein by reference in their entirety.

TECHNICAL FIELD

The subject matter described herein relates to medical devices and methods for the implantation of a sutureless prosthetic heart valve using minimally invasive procedures.

BACKGROUND

Prosthetic heart valves are used to replace damaged or diseased heart valves. In vertebrate animals, the heart is a muscular organ with four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is more common since they reside in the left side of the heart where pressures are the greatest.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Minimally invasive surgical techniques are evolving, where a valve prosthesis can be introduced into a patient using a catheter that is introduced via a small incision that provides access to, for example, a femoral artery or the heart. A major issue during heart valve replacement is positioning the prosthetic valve within a small, approximately 2-5 mm, range at the target site. Medical doctors have tried a variety of methods to confirm their judgment during heart valve replacement procedures, including various marking systems, contrast dye injections multiple times along the procedure, and viewing angle adjustments in the imaging systems. However, there are limitations with these methods and the current imaging systems. For example, the standard error of the current imaging systems is about 2 mm, and operator handling introduces additional variability. Furthermore, heart movement by itself can shift the target landing site by 2-5 mm. All these make it very difficult to land a prosthetic valve accurately.

Another critical issue with sutureless valves is valve migration. For example, when an aortic prosthetic valve is deployed, 100-200 mmHg pressure loads on the aortic valve immediately. The pressure times the valve surface area produces a substantial load force on the prosthetic valve and can cause valve migration towards the aortic arch. The other cause of valve migration is tilted valve landing. When tilted, the prosthetic valve will have a larger surface area facing the blood flow, which could push the prosthetic valve into the aorta.

There remains a need in the art for improved valve prosthesis and delivery devices for introducing a valve prosthesis into a patient.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a valve prosthesis is described. The valve prosthesis, in one embodiment, is comprised of a support frame radially expandable between a compact condition and an expanded condition, the support frame having an outer surface and defining a central orifice about an axis along an inflow-outflow direction. In one embodiment, the valve prosthesis is a sutureless cardiac valve prosthesis.

In one embodiment, the support frame comprises a plurality of flexible links arranged wherein one portion of the support frame can expand independently of the remaining portion.

The valve prosthesis also comprises a plurality of flexible leaflets attached to the support frame to provide a one-way valve in the orifice when the support frame is in its expanded condition and at least one valve clasper movable along the axis between a nesting position with the outer surface of the support frame and an engagement position. In one embodiment, the at least one valve clasper is physically separated from the support frame.

In one embodiment, the at least one valve clasper is comprised of first and second leg members and a u-shaped member. Each of the first and second leg members has a first and second end.

In one embodiment, each of the first ends of the leg members is attached to the u-shaped member by an apex.

In one embodiment, the second end of each leg member is proximal to the first end of each leg member.

In one embodiment, the apex is curved. In one embodiment, the first and second leg members are joined to the u-shaped member by the apex, wherein the first and second leg members are approximately parallel to each other.

In one embodiment, the valve clasper is comprised of a shape-memory material.

In one embodiment, each of the free ends of the leg members terminates in a detent. In another embodiment, the length of the detent can be variable. In another embodiment, the detent is comprised of a shape-memory material.

In one embodiment, the support frame has a length L, and the first and second leg members are at least L in length. In another embodiment, the support frame has a length L, and the first and second leg members are less than L in length. In yet another embodiment, the support frame has a length L, and the first and second leg members are approximately L in length.

In another embodiment, the support frame in its expanded condition has a radius r, and the at least one valve clasper is dimensioned to concentrically nest with the support frame when the support frame is in its expanded condition.

In another embodiment, the at least one valve clasper comprises two, three, four, or five valve claspers.

In an alternative embodiment, the valve claspers are each comprised of a u-shaped member. In one embodiment, the u-shaped member has a curved portion at the distal end of the valve clasper and two straight portions proximal to the curved portion. The two straight portions on opposite sides of the curved portion each end in a free end.

In one embodiment, the support frame has a length L, and each of the straight portions of the u-shaped member is at least L in length. In another embodiment, the support frame has a length L, and each of the straight portions of the u-shaped member is less than L in length. In yet another embodiment, the support frame has a length L and each of the straight portions of the u-shaped member is approximately L in length.

In one embodiment, each of the free ends of the u-shaped member terminates in a detent. In another embodiment, the length of the detent can be variable.

In still another embodiment, the support frame is at least partially covered by a covering. In certain embodiments, the covering is a fabric.

In yet another embodiment, the support frame is comprised of a shape-memory material.

In one embodiment, the valve clasper is comprised of a shape-memory material.

In one embodiment, the detent is comprised of a shape-memory material.

In one embodiment, the plurality of flexible leaflets is comprised of a biological material. In certain embodiments, the biological material is porcine or bovine.

In one embodiment, at least a portion of the at least one valve clasper is positioned between the support frame and the covering.

In one embodiment, the support frame comprises at least one fastener member attached to the support frame to create an orifice between the fastener member and the support frame. In another embodiment, a portion of the at least one valve clasper is positioned in the orifice between the at least one fastener and the support frame.

In one embodiment, when the support frame is in a compact condition, the at least one valve clasper is movable along the axis along an inflow-outflow direction. In another embodiment, when the support frame is in an expanded condition, the at least one valve clasper is restricted in movement along the axis along an inflow-outflow direction.

In another embodiment, when the support frame is in an expanded condition, the at least one valve clasper cannot freely move along the axis along an inflow-outflow direction.

In one embodiment, the valve prosthesis is an aortic valve prosthesis, a pulmonary valve prosthesis, or a mitral valve prosthesis.

In another aspect, an implantation device comprised of a valve prosthesis as described above and a delivery device is provided. The delivery device, in one embodiment, is comprised of a control unit, an at least one track wire consisting of a proximal end attached to the control unit and a distal end for contact with the at least one valve clasper, and a first sheath for encasing at least a portion of the support frame of the valve prosthesis in its compact condition. The valve prosthesis comprises at least one valve clasper, wherein the at least one valve clasper comprises two leg members, two apex members and a u-shaped member. In this embodiment, each of the two leg members has a first and a second end, wherein the first end of each leg member is attached to the u-shaped member and the second end of each leg member is free. In another embodiment, the first end of each leg member is attached to the u-shaped member by an apex. In one embodiment, each of the apex members is curved and the second ends of each of the leg member are distal to the first ends of each of the leg members.

In one embodiment, the implantation device further comprises a valve prosthesis pusher wire having a proximal end fixed to the control unit and a distal end for contact with the valve prosthesis.

In another embodiment, the control unit is comprised of a pusher wire controller. In still another embodiment, the valve prosthesis pusher wire terminates in a member for engaging the valve prosthesis. In yet another embodiment, the member for engaging the valve prosthesis pusher wire contacts the proximal end of the valve prosthesis.

In one embodiment, the valve prosthesis engaging member is v-shaped or u-shaped.

In yet another embodiment, the at least one track wire is a hollow track wire, and a locking wire is disposed within the hollow track wire. In one embodiment, the locking wire at its distal end has a locking member to releasably secure the at least one valve clasper to the at least one track wire.

In another embodiment, the control unit is comprised of a track wire controller.

The implantation device, in yet another embodiment, comprises a second sheath for encasing the at least one valve clasper.

In one embodiment, the second sheath is positioned serially with and distal to the first sheath.

In one embodiment, the control unit further comprises a first sheath controller.

In another embodiment, the second sheath is movable by means of a second sheath controller disposed in the control unit, the second sheath controller comprised of a second sheath control cable that extends from the second sheath to the second sheath controller. In one embodiment, the second sheath controller is located at or near the proximal end of the delivery device.

In still another embodiment, the second sheath control cable is hollow.

In another embodiment, the proximal end of the at least one track wire is attached to a release switch in the track wire controller.

In yet another embodiment, the control unit further comprises a first sheath controller.

In still another embodiment, the control unit is configured for independent control of each of the at least one track wire and the valve prosthesis pusher wire. In another embodiment, the control unit is configured for independent control of each of the at least one track wire and the second sheath control cable.

In one embodiment, the length of the first sheath is at least the length of the distance from an access port to the heart, wherein the distance is measured through an arterial or venous path.

In one embodiment, the first sheath is straight or curved.

In one embodiment, the second sheath is straight or curved.

In another aspect, an implantation device comprised of a valve prosthesis, wherein the valve prosthesis comprises at least one valve clasper, wherein the at least one valve clasper comprises a u-shaped member is provided.

In this embodiment, each of the free ends of the u-shaped member is located proximal to the curved portion of the u-shaped member.

The delivery device, in one embodiment, is comprised of a control unit, an at least one track wire consisting of a proximal end attached to the control unit and a distal end for contact with a free end of the at least one valve clasper, a first sheath for encasing at least a portion of the at least one valve clasper, and a second sheath for encasing at least a portion of the valve prosthesis support frame in its compact condition. The second sheath is positioned serially and distally to the first sheath.

In one embodiment, the second sheath encases the support frame of the valve prosthesis and at least a portion of the at least one valve clasper. In another embodiment, the second sheath encases the support frame of the valve prosthesis and at least a portion of the curved region of the at least one valve clasper.

In yet another embodiment, the at least one track wire is a hollow track wire, and a locking wire is disposed within the hollow track wire. In one embodiment, the locking wire at its proximal end has a locking member to releasably secure the at least one valve clasper to the at least one track wire.

In another embodiment, the control unit is comprised of a track wire controller.

In another embodiment, the second sheath is movable by means of a second sheath controller disposed in the control unit, the second sheath controller comprised of a second sheath control cable that extends from the second sheath to the second sheath controller. In one embodiment, the second sheath controller is located at or near the proximal end of the delivery device.

In still another embodiment, the second sheath control cable is hollow.

In another embodiment, the proximal end of the at least one track wire is attached to a release switch in the track wire controller.

In yet another embodiment, the control unit further comprises a first sheath controller.

In one embodiment, the implantation device further comprises a valve prosthesis pusher wire having a proximal end fixed to the control unit and a distal end for contact with the valve prosthesis.

In another embodiment, the control unit is comprised of a pusher wire controller. In still another embodiment, the valve prosthesis pusher wire terminates in a member for engaging the valve prosthesis. In yet another embodiment, the member for engaging the valve prosthesis pusher wire contacts the proximal end of the valve prosthesis.

In one embodiment, the valve prosthesis engaging member is v-shaped or u-shaped.

In still another embodiment, the control unit is configured for independent control of each of the at least one track wire and the second sheath control cable.

In one embodiment, a clasper multiplex unit is provided. In another embodiment, the clasper multiplex unit comprises two or more u-shaped members and two or more apex members, wherein a first u-shaped member is permanently attached to a second u-shaped member via a first and second apex member and one clasper multiplex leg member. In yet another embodiment, the clasper multiplex unit comprises three u-shaped members, six apex members, and three clasper multiplex leg members. In another embodiment, the clasper multiplex unit comprises four u-shaped members, eight apex members, and four clasper multiplex leg members.

In still another embodiment, each of the one or more multiplex leg members comprise a hole approximately at its proximal end.

In one embodiment, one or more multiplex leg members comprises one or more barbs. In another embodiment, each of the one or more barbs is present on opposite sides of the one or more multiplex leg members. In yet another embodiment, each of a plurality of barbs is present serially on one side of the one or more multiplex leg members. In still another embodiment, each of the plurality of barbs is present on alternate sides of at least one multiplex leg member.

In one embodiment, a clasper multiplex unit is provided, wherein the clasper multiplex unit comprises two or more u-shaped members and two or more apex members, wherein a first u-shaped member is permanently attached to a second u-shaped member via a first and second apex member, and wherein the clasper multiplex unit does not comprise a multiplex leg member permanently fixed to the clasper multiplex unit. In another embodiment the two or more apex members each comprise a hole. In one embodiment, the clasper multiplex unit comprises three u-shaped members and six apex members. In another embodiment, the clasper multiplex unit comprises four u-shaped members and eight apex members.

In one embodiment, a mechanism for the reversible attachment of a clasper multiplex unit to the control unit of a valve implantation device is provided. In this embodiment, the valve implantation device comprises a hollow track wire, a lock and release element, a flexible tension element, and a clasper multiplex unit. In another embodiment, the flexible tension element comprises a distal loop end. In another embodiment, the lock and release element is encased at least partially within the hollow track wire and is attached at its proximal end to the control unit of the implantation device. In yet another embodiment, the flexible tension element is encased at least partially within the hollow track wire and is attached at its proximal end to the control unit of the implantation device. In one embodiment, the distal end of the flexible tension element extends distal to the distal end of the lock and release element.

In one embodiment, the flexible tension element is comprised of a monofilament, multifilament or braided multifilament structure. In another embodiment, the flexible tension element is a wire, thread or monofilament. In another embodiment the flexible tension element is comprised of catgut, silk or linen. In yet another embodiment, the flexible tension element is nylon or polypropylene. In yet another embodiment, the flexible tension element is comprised of a shape memory metal.

In one embodiment, a method for reversibly attaching a clasper multiplex unit to a control unit of a valve implantation device is provided. In another embodiment, the method comprises 1) threading a distal loop end of a flexible tension element through the hole of a clasper multiplex unit leg member; 2) moving a lock and release element distal through the distal loop end of the flexible tension element; and 3) moving a hollow track wire in a distal direction until the hollow track wire encases at least the distal loop end of the flexible tension element and a portion of the clasper multiple unit leg member.

In one embodiment, a method for releasing a clasper multiplex unit from a control unit of a valve implantation device is provided. In another embodiment, the method comprises, 1) moving a hollow track wire in a proximal direction to uncover the proximal end of a clasper multiple leg member; 2) moving a lock and release element in a proximal direction until the lock and release element is not positioned through a distal loop end of a flexible tension element; and 3) moving the hollow track wire, the lock and release element and the flexible tension element in a proximal direction until the flexible tension element is not positioned through a hole of the clasper multiplex unit leg member.

In one embodiment, a mechanism for reversibly attaching a valve implantation device to a clasper multiplex unit is provided. In this embodiment, the mechanism comprises a valve implantation device, wherein the implantation device comprises a lock and release element, a flexible tension element and a hollow track wire, a clasper multiplex unit, and a flexible leg member. In one embodiment, the flexible leg member is reversibly attached at its proximal end to a distal loop end of a flexible tension element, and the flexible leg member is reversibly or permanently attached at its distal end to a clasper multiplex unit or to a valve prosthesis support frame. In one embodiment, the proximal end of the flexible tension element is attached to a control unit of a valve implantation device. In one embodiment, the clasper multiplex unit comprises a plurality of multiplex unit leg members. In another embodiment, the clasper multiplex unit does not comprise a multiplex unit leg member.

In one embodiment, a method for reversibly attaching a clasper multiplex unit from a control unit of a valve implantation device is provided. In this embodiment, the method comprises, 1) interlocking the proximal end of a flexible leg to a distal loop end of a flexible tension element; and 2) moving a hollow track wire in a distal direction until the hollow track wire encases at least the proximal portion of the flexible leg.

In one embodiment, a method for releasing a clasper multiplex unit from a control unit of a valve implantation device is provided. In this embodiment, the method comprises, 1) moving a hollow track wire in a proximal direction so that the hollow track wire does not encase the proximal end of a flexible leg member; and 2) pulling the hollow track wire and a flexible tension element in a proximal direction, wherein the flexible leg member straightens such that the flexible leg member is no long interlocked with the flexible tension element.

In another aspect, a method for deploying a cardiac valve prosthesis is provided. The method comprises providing an implantation device as described above, wherein the valve prosthesis comprises at least one valve clasper, wherein the at least one valve clasper comprises a u-shaped member and two leg members; inserting the implantation device into a heart chamber of a patient; guiding the implantation device to a position such that the second sheath encasing the at least one valve clasper passes through and extends beyond a cardiac valve in the heart of the patient; manipulating the implantation device to expose the at least one valve clasper and to anchor the at least one valve clasper in a sinus of the cardiac valve; adjusting by means of the control unit the position of the valve prosthesis such that a distal edge of the valve prosthesis is disposed approximately adjacent to the at least one valve clasper; sliding the first sheath in a proximal direction to release the valve prosthesis from the first sheath, whereby the valve prosthesis expands to its expanded condition to sandwich tissue of the cardiac valve between the valve prosthesis support frame and the at least one valve clasper; and removing the delivery device and the introducer from the patient.

In one embodiment, sliding the first sheath in a proximal direction comprises pulling the first sheath controller in a proximal direction while the valve prosthesis is held stationary.

In one embodiment, the implantation device is inserted through an introducer which has been inserted in a heart left ventricle of the patient.

In yet another embodiment, the step of providing an implantation device comprises providing a implantation device wherein the at least one valve clasper is encased in a second sheath on said delivery device. In another embodiment, guiding the implantation device comprises guiding the implantation device to position the second sheath through and beyond the cardiac valve in the patient. In yet another embodiment, the second sheath is positioned in the left atrium of the heart.

In one embodiment, manipulating the implantation device to expose the at least one valve clasper comprises manipulating the implantation device to move the second sheath to expose the at least one clasper. In another embodiment, manipulating the implantation device to move the second sheath to expose the at least one clasper comprises pulling a second sheath controller in a proximal direction while the at least one valve clasper is held stationary.

In one embodiment, an imaging system is used to position the first and second sheaths of the delivery device prior to uncovering the at least one valve clasper.

In one embodiment, the method comprises deploying a valve prosthesis, wherein the valve prosthesis is an aortic valve prosthesis. In another embodiment, the method comprises inserting the delivery device through the patient's thoracoabdominal region and into the left ventricle at or near the apex.

In one embodiment, the method further comprises advancing the second sheath through the aortic annulus into the left atrium and positioning the first sheath near the aortic annulus; advancing the second sheath in a distal direction to uncover the at least one valve clasper, wherein the at least one valve clasper expands radially within the left atrium; pulling back on the second sheath controller until the u-shaped member of the at least one valve clasper contacts the aortic sinus; advancing the first sheath until the distal end of the first sheath is approximately adjacent to the proximal end of the second sheath or until the distal end of the first sheath contacts the aortic annulus; pulling back on the first sheath while the valve prosthesis remains stationary to uncover and deploy the valve prosthesis; moving the at least one track wire release switch in a proximal direction while holding the locking wire stationary to release the leg members of the at least one valve clasper from the at least one track wire; moving the pusher wire controller in a proximal direction to disengage the at least one pusher wire engager from the valve prosthesis; advancing the first sheath in a distal direction until the distal end of the first sheath abuts the proximal end of the second sheath; and pulling back on the delivery device to remove the delivery device from the patient.

In one embodiment, the method comprises deploying a valve prosthesis, wherein the valve prosthesis is a pulmonary valve prosthesis. In another embodiment, the method comprises inserting the delivery device through the patient's femoral vein and advancing the delivery device through the inferior vena cava and into the right atrium.

In one embodiment, the method further comprises advancing the second sheath through the tricuspid annulus into the right ventricle, advancing the second sheath through the pulmonary annulus and positioning the second sheath in the pulmonary artery; advancing the second sheath in a distal direction to uncover the at least one valve clasper, wherein the at least one valve clasper expands radially within the pulmonary artery; pulling back on the second sheath controller until the u-shaped member of the at least one valve clasper contacts the pulmonary sinus; advancing the first sheath until the distal end of the first sheath is approximately adjacent to the proximal end of the second sheath or until the distal end of the first sheath contacts the aortic annulus; pulling back on the first sheath while the valve prosthesis remains stationary to uncover and deploy the valve prosthesis; moving the at least one track wire release switch in a proximal direction while holding the locking wire stationary to release the leg members of the at least one valve clasper from the at least one track wire; moving the pusher wire controller in a proximal direction to disengage the at least one pusher wire engager from the valve prosthesis; advancing the first sheath in a distal direction until the distal end of the first sheath abuts the proximal end of the second sheath; and pulling back on the implantation device to remove the implantation device from the patient.

In one embodiment, the method comprises deploying a valve prosthesis, wherein the valve prosthesis is a mitral valve prosthesis. In another embodiment, the method comprises inserting the implantation device through the patient's femoral vein and advancing the implantation device through the inferior vena cava and into the right atrium.

In one embodiment, the method further comprises advancing the distal end of the implantation device through the tricuspid annulus into the right ventricle, performing a transeptal puncture; advancing the distal end of the implantation device through the left atrium and through the mitral annulus, positioning the second sheath in the left ventricle and positioning the first sheath in the left atrium; advancing the second sheath in a distal direction to uncover the at least one valve clasper, wherein the at least one valve clasper expands radially within the left ventricle; pulling back on the second sheath controller until the u-shaped member of the at least one valve clasper contacts the mitral sinus; advancing the first sheath until the distal end of the first sheath is approximately adjacent to the proximal end of the second sheath or until the distal end of the first sheath contacts the mitral annulus; pulling back on the first sheath while the valve prosthesis remains stationary to uncover and deploy the valve prosthesis; moving the at least one track wire release switch in a proximal direction while holding the locking wire stationary to release the leg members of the at least one valve clasper from the at least one track wire; moving the pusher wire controller in a proximal direction to disengage the at least one pusher wire engager from the valve prosthesis; advancing the first sheath in a distal direction until the distal end of the first sheath abuts the proximal end of the second sheath; and pulling back on the implantation device to remove the implantation device from the patient.

In yet another aspect, a device for delivery of a medical prosthesis into a patient is provided. The device comprises a tubular steering wire extending from a distal end of the device to a proximal end of the device, a control unit at the proximal end of the device, a first sheath comprising an open lumen, the first sheath disposed distally with respect to the control unit, at least one track wire having a proximal end attached to the control unit and a distal end for contact and control of a medical prosthesis, and a pusher wire having a proximal end fixed to said control unit and a distal end for controlled contact with the medical prosthesis.

In one embodiment, the control unit is comprised of a pusher wire controller and a track wire controller, wherein the pusher wire controller and the track wire controller are independently controllable.

In another embodiment, the proximal end of said at least one track wire is attached to a release switch in the track wire controller.

In yet another embodiment, the proximal end of the at least one pusher wire is attached to a movable control in the pusher wire controller.

In another aspect, a method for deploying a cardiac valve prosthesis is provided. The method comprises providing an implantation device as described above; inserting the implantation device into a heart chamber of a patient; guiding the implantation device to a position such that the second sheath encasing the valve prosthesis is positioned approximately within the native valve; manipulating the implantation device to expose the curved portion of the u-shaped member of the at least one valve clasper, expose the straight portions of the u-shaped member and at least a distal portion of the at least one track wire to allow the at least one valve clasper to expand radially into an engagement position; anchoring the at least one valve clasper in a sinus of the cardiac valve; sliding the second sheath in a distal direction to release at least a portion of the valve prosthesis support frame from the second sheath; and sliding the second sheath in a distal direction to release the entire valve prosthesis support frame from the second sheath, whereby the valve prosthesis expands to its expanded condition to sandwich tissue of the native cardiac valve between the valve prosthesis support frame and the at least one valve clasper; and removing the delivery device and the introducer from the patient.

In this embodiment, leaflets of the native cardiac valve are curved toward the distal end of the implantation device which has entered the heart chamber.

In one embodiment, manipulating the implantation device to expose the curved portion of the u-shaped member of the at least one valve clasper comprises moving the second sheath in a distal direction. In another embodiment, exposing the straight portion of the at least one valve clasper and at least a distal portion of the at least one track wire comprises moving the track wire control unit in a distal direction while holding the first sheath stationary.

In one embodiment, sliding the second sheath in a distal direction comprises pushing the second sheath controller cable in a distal direction while holding the implantation device stationary.

In one embodiment, inserting the implantation device into a heart chamber comprises inserting the implantation device into the femoral artery and advancing the implantation device through the aortic arch into the left atrium. In this embodiment, the cardiac valve prosthesis is a aortic valve prosthesis.

In one embodiment, inserting the implantation device into a heart chamber comprises inserting the implantation device through an introducer which has been inserted in a heart left ventricle of the patient and advancing the implantation device to the left ventricle. In this embodiment, the cardiac valve prosthesis is a mitral valve prosthesis.

In yet another aspect, an implantation device is provided which comprises a flexible framework comprising a plurality of prosthetic leaflets; a plurality of valve claspers movably attached to the flexible framework wherein the valve clasper comprises a clasper ear and two clasper shafts; a first sheath which encases the flexible framework in a compact state and which comprises a clasper pusher; a second sheath which encases the plurality of claspers in a compact state; a clasp pusher located in the second sheath and a valve stopper located in said first sheath; wherein the first sheath is located distal to the second sheath prior to deployment of the flexible framework in the annulus.

In still another aspect, a method for deploying a cardiac valve prosthesis is provided. The method comprises providing a cardiac implantation device as described above, inserting the implantation device into the femoral artery and guiding the implantation device through the femoral artery to the left ventricle of the heart until the first sheath is located within the annulus of the left ventricle and the second sheath is located in the left atrium; sliding the second sheath in a proximal direction to uncover the plurality of valve claspers such that the clasper ears extend radially within the left atrium; pushing the valve claspers distally until the clasper ears contact the floor of the aortic valve sinus; sliding the first sheath distally to uncover the flexible framework such that the flexible framework extends radially to form an expanded flexible framework and each native heart valve is sandwiched between the clasper ear and the expanded flexible framework.

In addition to the exemplary aspects and embodiments described above, further aspects and embodiments will become apparent by reference to the drawings and by study of the following descriptions.

BRIEF DESCRIPTION OF THE DRAWINGS

FIG. 5A is a transverse view of a valve clasper movably connected to a prosthetic valve support frame structure in its compact condition in situ, wherein an apex member connects a leg member and a u-shaped member. The valve clasper is in an engagement position.

FIG. 5B is a transverse view of a valve clasper movably connected to a prosthetic valve support frame structure in its compact condition in situ, wherein an apex member connects a leg member and a u-shaped member. The valve clasper is in a nested position.

FIG. 5C is a transverse view of a valve clasper movably connected to a prosthetic valve support frame structure in the expanded condition in situ, wherein an apex member connects a leg member and a u-shaped member.

FIG. 5D is a transverse view of a valve clasper movably connected to a prosthetic valve support frame structure having engagement fasteners and in its compact condition in situ. The valve clasper is in an engagement position.

FIG. 5E is a transverse view of a valve clasper movably connected to a prosthetic valve support frame structure having engagement fasteners and in its compact condition in situ. The valve clasper is in a nested position.

FIG. 5F is a transverse view of a valve clasper movably connected to a prosthetic valve support frame structure having engagement fasteners and in the expanded condition in situ.

FIGS. 10A-10C illustrate various embodiments for connecting track wires to valve claspers.

DETAILED DESCRIPTION

Figure 1A:
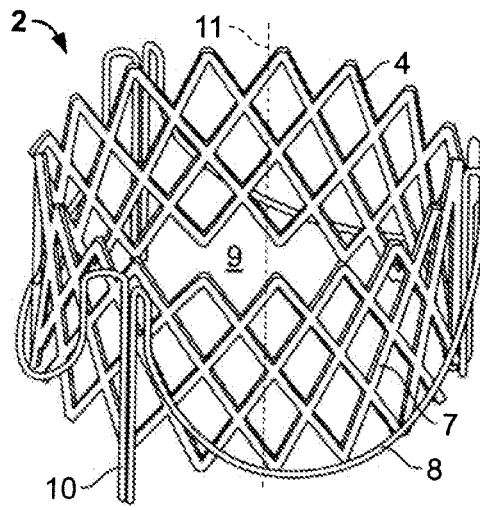
FIG. 1A is a perspective view of one embodiment of a valve prosthesis support frame with a plurality of claspers.

The present disclosure provides devices, systems and methods for valve replacement, preferably using a minimally invasive surgical technique. While the devices and methods will have application in a number of different vessels in various parts of the body, they are particularly well-suited for replacement of a malfunctioning cardiac valve, and in particular an aortic valve, a pulmonary valve or a mitral valve. The devices and methods are particularly advantageous in their ability to provide a more flexible prosthetic heart valve implantation device, ensure accurate and precise placement of the prosthetic heart valve with reduced reliance on imaging, and provide additional anchoring of the prosthetic valve, reducing the incidence of valve migration. Another advantage is the delivery and implantation of a sutureless valve prosthesis as described herein.

The present disclosure also provides improved devices and methods for implanting a prosthetic heart valve. In particular, improved minimally invasive methods and devices are provided for antegrade, percutaneous or femoral transcatheter implantation of expansible prosthetic heart valves within or adjacent a valved anatomic site within the heart. In particular, the improved prosthetic heart valve devices and methods of the present disclosure provide more flexibility in the valve replacement procedure, ensure accurate and precise placement of the prosthetic heart valve with reduced reliance on imaging, and provide additional anchoring of the prosthetic valve, reducing the incidence of valve migration or misalignment.

One method for deploying an aortic valve generally comprises inserting a valve delivery system between the ribs of the patient or subject into the apex of the left ventricle, then delivering the valve prosthesis to the site of the patient's diseased valve (transapical delivery). Another method of deploying the aortic valve generally comprises gaining access to the aorta through the femoral artery (femoral delivery).

Another method for deploying a pulmonary or a mitral valve generally comprises inserting a valve delivery system into the jugular vein, then guiding the system through the superior vena cava into the right atrium. The device can then be advanced into the right ventricle and to the pulmonary valve. Alternatively, the device can be advanced via transeptal puncture into the left atrium, then advanced to the mitral valve.

Yet another method for deploying a pulmonary or a mitral valve generally comprises inserting a valve delivery system into the femoral vein, then guiding the system through the superior vena cava into the right atrium, and advancing the device to the pulmonary or mitral valve as described above.

The valve delivery system or implantation device is of sufficient size and length to pass through a first opening in a patient's body (e.g., an aorta or a femoral artery or vein access point), through a patient's aorta, femoral artery or vein. The implantation device may alternatively enter through a transthoracic port which provides access through the patient's thoracoabdominal (e.g., intercostal) region and into the left ventricle at or near the apex. The transthoracic port according to various exemplary embodiments is one of an introducer, trocar, or cannular, as is generally known in the art.

At least one delivery sheath or catheter is advanced along a guidewire through and past the aortic, mitral or pulmonary valve. These methods are described herein below, with reference to the prosthetic valve and delivery device to be described. A skilled artisan, however, will appreciate that other methods of deploying the prosthetic valve described herein can be used.

The access port includes one or more hemostasis valves or seals. The hemostasis valve or seal is adapted to provide a blood tight seal against blood loss or leakage during the procedure, and can be used at the apex, at the aorta, or in both locations. The port is configured to allow passage of the implantation device, catheter, or any tools or devices to be delivered to the target site using the implantation device, while at the same time providing a blood tight seal against blood loss or leakage. Such methods are well known to those having ordinary skill in the art.

The devices and methods described herein may be used with subjects including humans and other mammals, including but not limited to rats, rabbits, pigs, dogs, sheep and horses.

A number of embodiments of the present invention will below be described with reference to the attached drawings. It should be understood that the various elements of any one particular embodiment may be utilized in one or more of the other embodiments, and thus combinations thereof are within the scope of the appended claims.

I. Prosthetic Valves

In a first aspect, and with initial reference to FIG. 1A, a valve prosthesis 2, which in a preferred embodiment is a prosthetic heart valve, is provided. The valve prosthesis is configured to be placed in a native diseased valve of a subject, such as a native stenotic aortic, pulmonary or mitral valve, using a minimally-invasive approach such as a beating heart transapical procedure, or a retrograde transaortic procedure. Such procedures are well known to persons having ordinary skill in the art.

The sutureless prosthetic heart valve comprises a self-expanding support frame, prosthetic valve leaflets (not shown in FIG. 1A) and one or more valve claspers. The valve claspers may be positioned serially or concentrically with the support frame. Both the support frame and the valve claspers can be made from a shape memory material such that they can be compressed to a radius which allows delivery through, for example, arteries and veins, then expanded as needed for deployment and placement of the valve in the appropriate position.

The valve claspers are movably connected to the support frame such that the valve claspers may be moved from a proximal or distal position from the support frame to a concentric position with the support frame. During delivery of the valve prosthesis, it is advantageous to have the valve claspers positioned serially from the support frame. This allows the user to minimize the radius of the device which must be advanced through, for example, arteries and veins. The distance from which the valve claspers may be serially displaced from the support frame is highly variable, such that the valve claspers may be adjacent to the support frame, or potentially inches or feet away from the support frame during the delivery procedure. In some embodiments, no part of the valve claspers are physically fixed to the support frame, such as by welding or otherwise adhering.

By "movably connected" (alternatively, "movably attached") it is understood that while two structural elements may be in physical contact at any given time, they are not irreversibly connected or attached, such as by welding or through an adhesive. For example, after deployment of the prosthetic valve as described herein, while the valve claspers are in physical contact with the prosthetic valve support frame, the valve claspers are able to move longitudinally with respect to the support frame. Also, portions of the valve clasper can move radially from the support frame. Regardless, the valve claspers remain movably connected to the support frame.

As a result, when the support frame is in a compact or non-expanded condition, the valve claspers can freely move along the longitudinal axis in either a proximal or distal direction. In some embodiments, the valve claspers are movably connected to the support frame in a manner that prevents the entire valve clasper from being radially displaced from the support frame, however, portions of the valve clasper can be radially displaced from the support frame as needed. When the support frame is deployed or expanded within the native heart valve, the valve claspers become sandwiched between the support frame and the native valve tissue, becoming at least partially, and may be fully immobilized. The valve claspers also function to hold the deployed prosthetic valve in place within the native valve.

As shown in FIG. 1A, which is representative, the valve prosthesis comprises a support frame (e.g., a stent frame) 4 which comprises an outer surface 7 and defines a central orifice 9 about an axis (the longitudinal axis denoted by dashed line 11 in FIG. 1A) along an inflow-outflow direction. The support frame is radially expandable between a compact or compressed condition and an expanded or deployed condition.

The support frame can be a lattice design which can have different shapes, including but not limited to, diamond and oval shape. A support frame may have additional features, such as a plurality of flex-links 18 as shown in support frame 16 depicted in FIG. 1C. Design of the support frame with the plurality of flex links allows expansion of a portion of the valve support frame as illustrated in FIG. 1D.

The support frame can be self-expanding. In some embodiments, the self-expanding support frame can be comprised of a shape-memory metal which can change shape at a designated temperature or temperature range. Alternatively, the self-expanding frames can include those having a spring-bias. The material from which the support frame is fabricated allows the support frame to automatically expand to its functional size and shape when deployed but also allows the support frame to be radially compressed to a smaller profile for delivery through the patient's vasculature. Examples of suitable materials for self-expanding frames include, but are not limited to, medical grade stainless steel, titanium, tantalum, platinum alloys, niobium alloys, cobalt alloys, alginate, or combinations thereof. Examples of shape-memory materials include shape memory plastics, polymers, and thermoplastic materials which are inert in the body. Shape memory alloys having superelastic properties generally made from ratios of nickel and titanium, commonly known as Nitinol, are preferred materials.

Figure 1B:
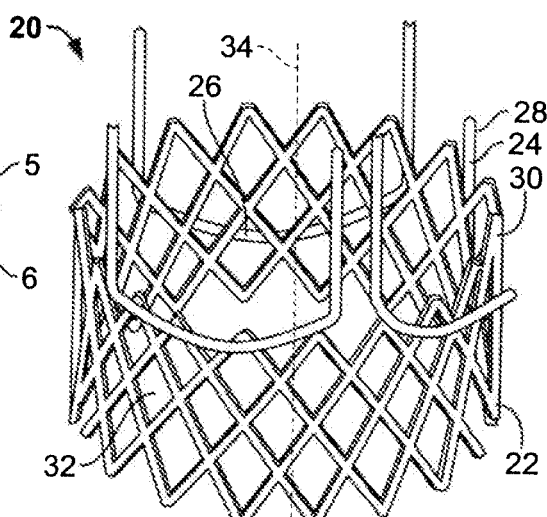
FIG. 1B is a perspective view of one embodiment of a valve prosthesis support frame with a plurality of valve claspers.
Figure 1C:
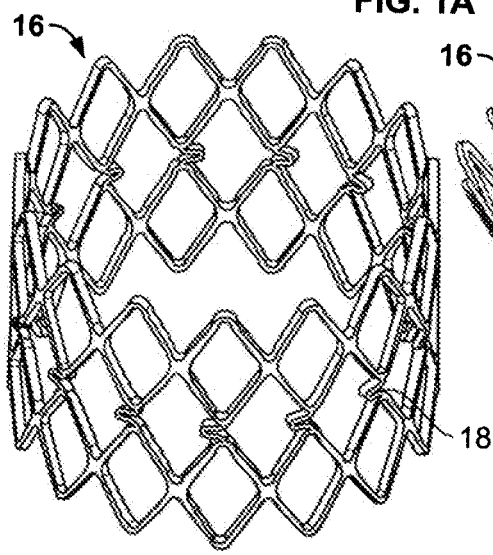
FIG. 1C is a perspective view of one embodiment of a valve prosthesis support frame.
Figure 1D:
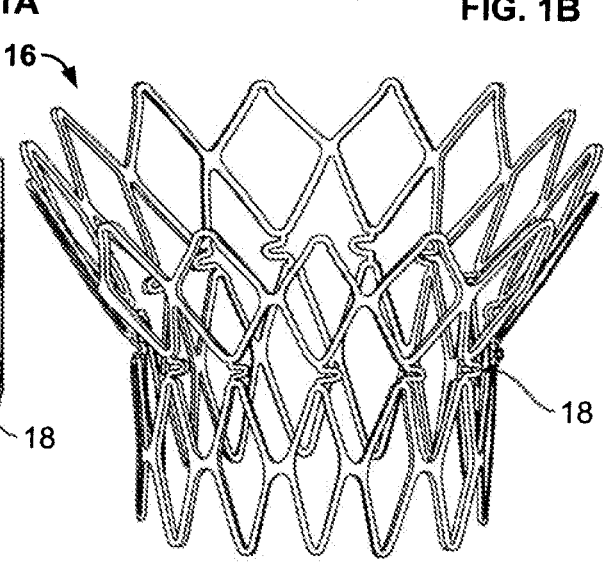
FIG. 1D is a perspective view of one embodiment of a valve prosthesis support frame in a partially expanded condition.
Figure 1E:
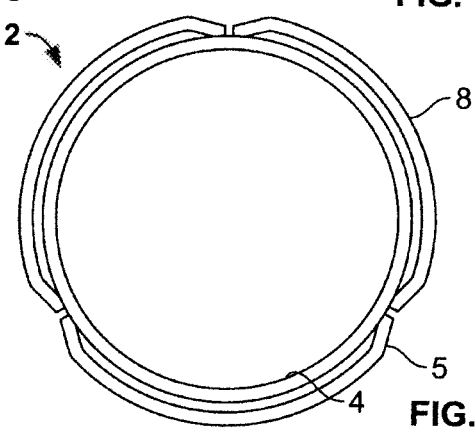
FIG. 1E is a top view of one embodiment of a valve prosthesis support frame with a plurality of valve claspers.

An alternative embodiment of the support frame is illustrated in FIGS. 1C-1D. As shown, support frame 16 has a plurality of flexible links 18. The presence and arrangement of flexible links 18 allows the portion of the support frame on one side of the flexible links to expand or compress independently of the portion on the other side of the flexible links, as depicted in FIG. 1 D. The functional significance of this structural feature is described in further detail below.

In an alternative embodiment, the support frame is not self-expanding, and may be expanded, for example, using a balloon catheter as is well known in the art.

In an exemplary embodiment, the valve prosthesis further comprises at least one valve clasper, such as valve clasper 6 which is illustrated in FIG. 1A. Valve claspers may alternatively be referred to as sinus locators, valve positioners, or valve hangers. In some embodiments, valve claspers are comprised of a shape-memory metal. In further embodiments, the shape memory alloy is Nitinol.

In an exemplary embodiment, the at least one valve clasper 6 is movably connected to the valve support frame 4. In another embodiment, the at least one valve clasper 6 is movably connected to the valve support frame 4 when the valve support frame 4 is in a compact condition prior to delivery and deployment. In yet another embodiment, the at least one valve clasper 6 is not fixed to the valve support frame 4. It is understood that each valve clasper of a valve prosthesis described herein is separate from the valve support frame. Thus, although a least a portion of the valve clasper, e.g., the leg member, may be in contact with or otherwise reversibly attached or connected to the valve support frame, no part of the valve clasper is fixed, e.g., welded or otherwise irreversibly adhered, to the valve support frame. Alternatively stated, the valve clasper, which may be in contract with or otherwise reversibly attached to the valve support frame, is not irreversibly fixed to the valve support frame.

The at least one valve clasper is comprised, in one embodiment, of a u-shaped member 8 and two leg members, such as leg member 10 which is representative. In some embodiments, each of two leg members 10 of the valve clasper is positioned approximately parallel to the longitudinal axis of the support frame and is attached to u-shaped member 8 by an apex 5. In some embodiments, each of the two leg members of the valve clasper has a first and second end, wherein each of the first ends of the two leg members are joined to the u-shaped member 8. An apex 5 is present between each leg and the u-shaped member. As used herein, an apex, e.g., apex 5, is defined as a vertex formed by the joining of u-shaped member 8 and one leg member 10. In one embodiment, the vertex is curved. In another embodiment, the vertex is curved such that two leg members 10 are approximately parallel to each other. In some embodiments, the second ends of the two leg members are free ends.

Figure 2A:
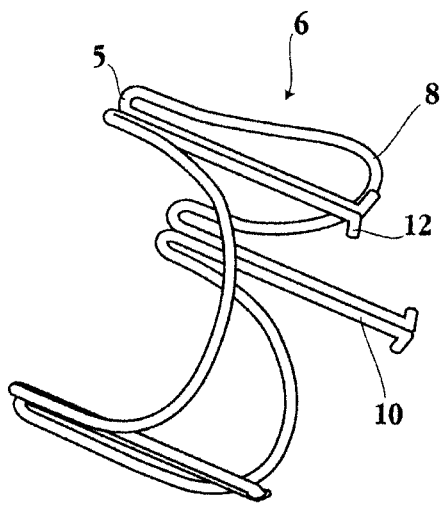
FIGS. 2A and 2B illustrate a perspective view of a plurality of valve claspers with detents.

In additional embodiments, the second terminus or end of one or more of the leg members terminates in a detent 12 (also referred to as a foot or barb), as shown in FIG. 2A. Detent 12 may be made of a shape memory alloy such as nitinol. For some applications, the detents are oriented parallel to a longitudinal axis of the valve prosthesis, while for other applications, the detents are oriented to form an angle with respect to the longitudinal axis. For example, the detents may be approximately parallel to the longitudinal axis of the valve prosthesis support frame in the compact position and/or when the valve prosthesis is encased in a sheath. Alternatively, the detents may form an angle with respect to the longitudinal axis of the valve prosthesis or a leg member when the valve prosthesis is in an expanded condition. In other embodiments, the detents can have varying lengths. In some embodiments, the leg members may have, for example, a zig-zag or coiled shape after deployment of the valve prosthesis. The detents help to secure the valve claspers to the valve support frame after the valve prosthesis is deployed in the native valve.

In some embodiments, the support frame has a length L and the leg members are at least L in length. In other embodiments, the leg members are equal to or less than length L.

It will be appreciated by those with skill in the art that the shape of the member joining the two leg members is not limited to being a u-shape. The u-shaped member may have other shapes including, but not limited to, rectangle, square, diamond, triangle, oval, circle, or a combination of these shapes. The u-shaped member may be of any shape that allows it to engage and/or rest against the floor of the native valve sinus or adjacent to the commissure of the native valve leaflets.

The at least one valve clasper is movable along the longitudinal axis of the support frame. When the valve clasper is off-set from the support frame, e.g., when the u-shaped member of the valve clasper is in a position distal to the proximal end of the support frame and/or does not approximately fully overlap with the support frame, this position is referred to as the engagement position. In this position, u-shaped member 8 of a valve clasper may extend radially from a leg member and the longitudinal axis of support frame 4 in its compact condition.

In situ, when the valve clasper is in the nesting position, clasper apex 5 is approximately adjacent to the distal end of support frame 4. Alternatively, the valve clasper is in its nesting position when at least a portion of the u-shaped member is in contact or adjacent to the floor of a native sinus or the commissures of the native leaflets of the valve. In some embodiments, when a leg member, such as leg member 10, has a length L which is approximately equal to the length L of the valve prosthesis support frame, and a valve clasper, such as valve clasper 6, is in a position such that the leg members approximately completely overlap with the valve prosthesis support frame 4, this position is referred to as the nesting position.

In a second aspect, as illustrated in FIG. 1B, a valve prosthesis 20 comprises valve support frame 22 and a central orifice 32. Support frame 22 is radially expandable between a compact condition and an expanded condition. Support frame 22 has an outer or external surface 30 and defines a central orifice 32 about an axis (the longitudinal axis denoted by dashed line 34 in FIG. 1B). The longitudinal axis corresponds to the inflow-outflow axis. In some embodiments, the valve prosthesis further comprises a plurality of prosthetic valve leaflets (not shown in FIG. 1B).

In this embodiment, valve prosthesis 20 further comprises at least one valve clasper 24. At least one valve clasper 24 comprises a u-shaped member 26. The u-shaped member 26 has a curved portion at its proximal end connected to two straight portions, e.g., 28, each ending in a free end, as seen in FIG. 1B.

Figure 2B:
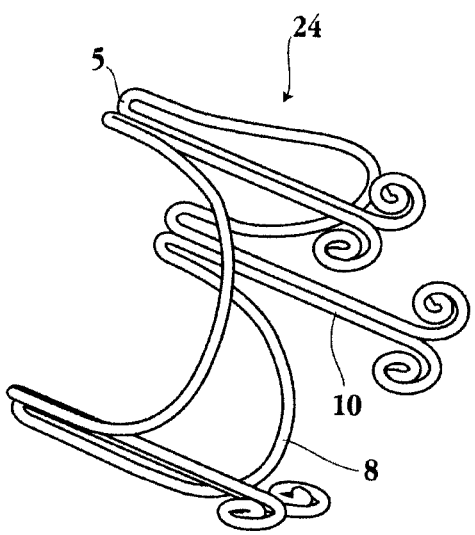

In some embodiments, the straight portion of valve clasper 24 remains straight following deployment of valve prosthesis 20. In an alternative embodiment, at least part of the straight portion of the at least one valve clasper 24, which may be made of a shape memory material, may have, for example, a zig-zag or coiled shape after deployment of valve prosthesis 20 as shown in FIG. 2B for clasper 6.

The at least one valve clasper 24 is movably connected to support frame 22 and movable along the longitudinal axis of support frame 22. When valve clasper 24 is off-set from the support frame, e.g., when the free ends of valve clasper 24 are in a position proximal to the proximal end of support frame 22 and/or when valve clasper 24 does not fully overlap with the support frame, this position is referred to as the engagement position. In this position, at least one u-shaped member 26 of valve clasper 24 may extend radially from the longitudinal axis of support frame 22 in its compact condition.

In situ, when valve clasper 24 is in the nesting position, at least a portion of at least one u-shaped member 26 is in contact with or adjacent to the floor of a native sinus or adjacent to the native valve commissure.

In some embodiments, the plurality of valve claspers 6 or 24 movably connected to support frame 4 or 22, respectively, can be two, three, four, five, or more valve claspers, to accommodate different valve replacement procedure or according to the anatomical structure of the native valve that is to be replaced. In a particular embodiment, the number of valve claspers in the valve prosthesis is three.

In one embodiment, the plurality of valve claspers 6 movably connected to support frame 4 can be joined to generate a single valve clasper comprising multiple u-shaped members 8 and multiple leg members 10.

The valve prostheses 2 and 20, as described herein can further comprise a plurality of prosthetic valve leaflets having surfaces defining a reversibly sealable opening for unidirectional flow of a liquid through the prosthetic valve. The prosthetic valve can include three valve leaflets for a tri-leaflet configuration. As appreciated, mono-leaflet, bileaflet, and/or multi-leaflet configurations are also possible. For example, the valve leaflets can be coupled to the valve frame so as to span and control fluid flow through the lumen of the prosthetic valve.

Figure 3A:
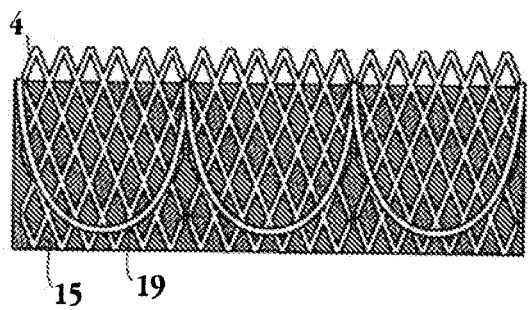
FIG. 3A illustrates a valve prosthesis support frame in a flat form with a plurality of valve claspers and a covering.

In some embodiments, the leaflets comprise synthetic material, engineered biological tissue, biological valvular leaflet tissue, pericardial tissue, cross-linked pericardial tissue, or combinations thereof. In other embodiments, the pericardial tissue is selected from but not limited to the group consisting of bovine, equine, porcine, ovine, human tissue, or combinations thereof. Prosthetic valve leaflets may be sewed onto valve support frame 4 or 22 along a leaflet suture line, e.g. suture line 19 as shown in FIG. 3A, which is a rolled-out view of a support frame. In other embodiments, valve leaflets are fixed onto support frame 4 or 22 by other comparable methods understood by those with ordinary skill in the art.

In some embodiments, the support frame of valve prosthesis 2 or 20 is at least partially covered by a covering. This is depicted in FIG. 3A for a support frame 4 of valve prosthesis 2, wherein the support frame is covered by a covering (graft covering) 15. Any suitable lightweight, strong, fluid impervious, biocompatible material may be utilized. The covering may be attached in any suitable manner and by any suitable means. For example, the covering may be reversibly attached or permanently attached to the support frame. The covering may be positioned on the external and/or internal surface of the valve prosthesis support frame. The covering may be attached to the frame utilizing sutures, staples, chemical/heat bonding and/or adhesive. In some embodiments, the covering is a fabric. In further embodiments, the fabric is comprised of, for example, a material identified by a tradename selected from Nylon®, Dacron®, or Teflon®, or is expanded polytetrafluoroethylene (ePTFE), and/or other materials.

In one embodiment, the covering can further include a sealing material. The sealing material can be selected from the general class of materials that include polysaccharides, proteins, and biocompatible gels. Specific examples of these polymeric materials can include, but are not limited to, those derived from poly(ethylene oxide) (PEO), poly(ethylene glycol) (PEG), poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers. Examples of the polysaccharide include those derived from alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan. Examples of proteins include those derived from gelatin, collagen, elastin, zein, and albumin, whether produced from natural or recombinant sources. The materials can be bioactive agents, including those that modulate thrombosis, those that encourage cellular ingrowth, through-growth, and endothelialization, those that resist infection, and those that reduce calcification. The covering may be on the inside and/or outside surface of the support frame, and may be disposed to partially cover the support frame or to fully cover the support frame.

In one embodiment, at least a portion of at least one leg member 10 of valve clasper 6 is positioned between support frame 4 and the covering on the surface of support frame 4. In this embodiment, the covering can function at least in part to movably connect valve clasper 6 to support frame 4. In one embodiment, the at least one leg member 10 fixed at a first end to the at least one u-shaped member 8, are movable parallel to longitudinal axis 11, wherein at least a portion or substantially of the at least one leg member 10 can be positioned between the covering and support frame 4.

In one embodiment, the curved portion of the u-shaped member 26 of valve clasper 24 and/or a part of straight portion 28 is positioned between support frame 22 and the covering on the surface of the support frame. In this embodiment, the covering can function at least in part to movably connect valve clasper 24 to support frame 22. In one embodiment, the two straight portions of the valve clasper 24 is movable parallel to longitudinal axis 32, wherein at least a portion or substantially of the valve clasper is positioned between the covering and support frame.

In one embodiment, support frame 4 or 22 may be coated with a material which promotes and/or supports tissue growth in the region in which the valve prosthesis is deployed. Alternatively, the material which promotes and/or supports tissue growth may be imbedded or incorporated in the covering.

Figure 3B:
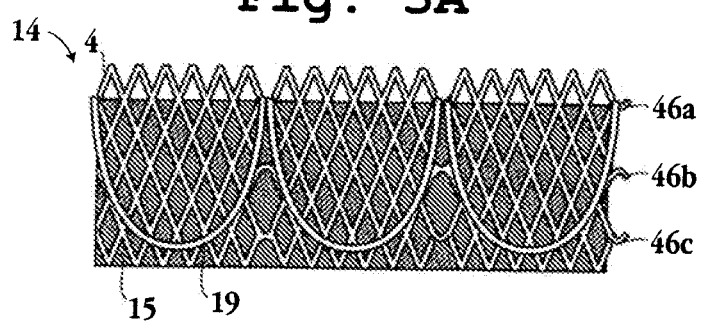
FIG. 3B illustrates a valve prosthesis support frame in a flat form with a plurality of valve claspers, engagement fasteners and a covering.

In an alternative embodiment, shown in FIG. 3B, a support frame 14 further comprises a plurality of engagement fasteners, such as fastener 46. The engagement fasteners can be directly fixed on the support frame or can be manufactured as part of the support frame. Each set of engagement fasteners are formed by several engagement fasteners that are arranged linearly along the longitudinal axis of the support frame. Each engagement fastener may be a half circle shape, with the open side facing opposite directions in alternating engagement fasteners within each set of engagement fasteners. The leg members of the valve claspers are inserted through the openings formed by each set of engagement fasteners.

FIGS. 3A and 3B also illustrate an embodiment wherein the support frame is covered with a covering 15.

Figure 4A:
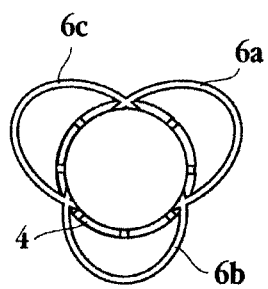
FIGS. 4A-4D illustrate a top view of a valve prosthesis support frame with movably connected claspers in which the support frame is in a compact (FIGS. 4A and 4C) or an expanded (FIGS. 4B and 4D) condition.
Figure 4C:
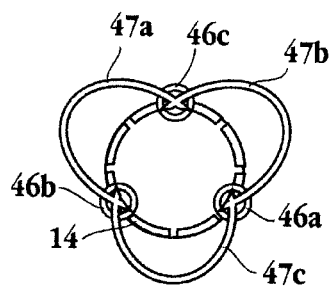
Figure 4E:
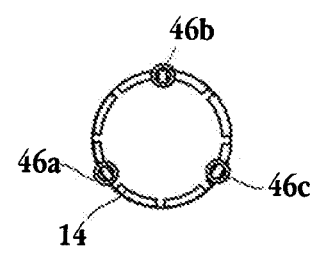
FIGS. 4E and 4F illustrate a top view of a valve prosthesis support frame with engagement fasteners in a compact (FIG. 4E) or expanded (FIG. 4F) condition.
Figure 4B:
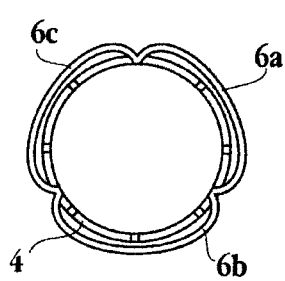
Figure 4D:
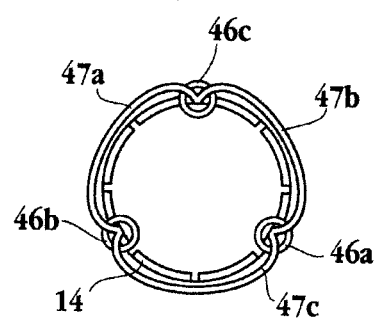
Figure 4F:
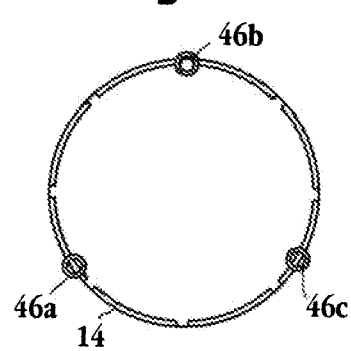

During valve delivery, the support frame of prosthetic valve is initially in a compact condition. In the embodiment where the valve clasper(s), which is/are also compact (not radially extending from the support frame), is/are movable between an engagement position and a nesting position, the valve clasper(s) during valve delivery is/are in an engagement position where the valve clasper(s) is/are positioned distally or proximally from the support frame. Once the valve prosthesis is at or near a desired in vivo position where a replacement valve is needed, the valve claspers, such as valve claspers 6a, 6b, 6c in FIG. 4A, are moved to an open or expanded condition, for contact with and seating into a sinus of a native heart valve. Support frame 4 as shown in FIGS. 4A and 4B is then moved to an expanded condition. A plurality of valve claspers 6a, 6b, 6c movably connected to the support frame in the compact condition, are shown in FIG. 4A as viewed from the top. FIG. 4B shows the plurality of valve claspers with support frame 4 in its expanded condition. FIG. 4C shows a support frame 14 having engagement fasteners 46a, 4Gb, 46c wherein the support frame 14 is in a compact condition and the u-shaped members of valve claspers 47a, 47b, 47c are in an open or expanded condition for contact with and seating into a sinus of a native heart valve. FIG. 4D shows the plurality of valve claspers with support frame 14 in its expanded condition. FIGS. 4E and 4F show support frame 14 having engagement fasteners 46a, 46b, 46c, wherein support frame 14 is in a compact condition (FIG. 4E) and an expanded condition (FIG. 4F).

FIG. 5A illustrates a valve clasper 6 movably attached to support frame 4 relative to a native heart valve leaflet 30. When the support frame is in its compact condition, valve clasper 6 is movable from an engagement position (FIG. 5A) to a nesting position (FIG. 5B), where valve clasper 6 is in a nested or concentric arrangement with the support frame, and wherein u-shaped member 8 approximately contacts the sinus (e.g., aortic, mitral or pulmonary sinus) of the native heart leaflet 30 (see FIG. 5B). A prosthetic leaflet 36 is attached to support frame 4 and extends into the orifice of the prosthetic valve, to provide in conjunction with one or more additional prosthetic leaflets (not shown), a one-way valve in the orifice. As seen in FIG. 5C, after support frame 4 is radially enlarged to an expanded condition, at least a portion of native valve leaflet 30 is sandwiched between u-shaped member 8 and support frame 4. Also shown in FIGS. 5A-5C is covering 15, which in some embodiments, may function in part to hold the leg member adjacent to the support frame.

FIGS. 5D-5F show support frame 14 with engagement fasteners 46a, 46b, 46c, wherein the valve clasper is above the native valve sinus and in an engagement position (FIG. 5D), the valve clasper has moved toward the valve sinus to allow u-shaped member 11 to contact the native valve sinus (FIG. 5E) and support frame 14 has expanded radially so that at least a portion of native valve leaflet 30 is sandwiched between u-shaped member 11 and support frame 14 (FIG. 5F).

Figure 5G:
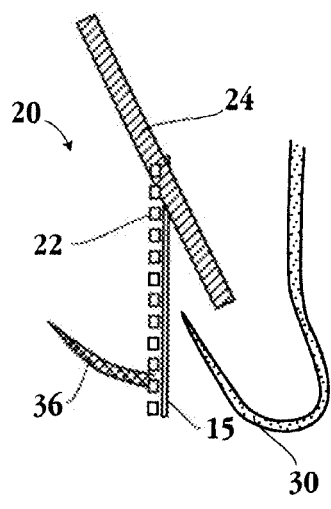
FIG. 5G is a transverse view of one embodiment of a valve clasper movably connected to a prosthetic valve support frame structure in its compact condition in situ. The valve clasper is in an engagement position.
Figure 5H:
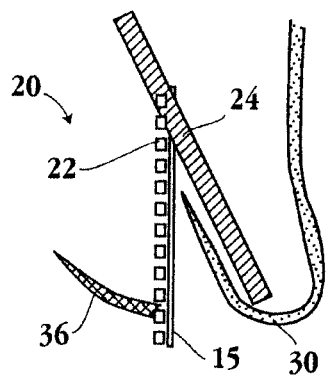
FIG. 5H is a transverse view of one embodiment of a valve clasper movably connected to a prosthetic valve support frame structure in its expanded condition in situ. The valve clasper is in a nested position.
Figure 5I:
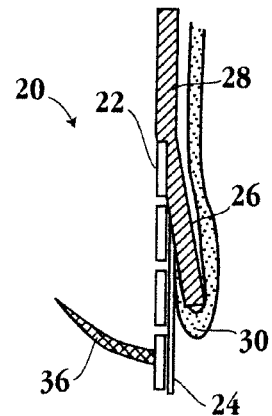
FIG. 5I is a transverse view of one embodiment of a valve clasper movably connected to a prosthetic valve support frame structure in its compact condition in situ.

In another embodiment, shown in FIGS. 5G-5I, valve clasper 24 is movably connected to support frame 22. In FIG. 5G, valve clasper 24, in an engagement position, is above the native valve and is radially expanded from support frame 22. As described above, when support frame 22 is in its compact condition, valve clasper 24 is movable from an engagement position (FIG. 5G) to a nesting position (FIG. 5H), where valve clasper 24 is in a nested or concentric arrangement with the support frame, and wherein u-shaped member 26 approximately contacts the sinus of native heart leaflet 30. As shown in FIG. 5I, support frame 22 is then radially enlarged to an expanded condition so that at least a portion of native valve leaflet 30 is sandwiched between valve clasper 24 and support frame 22. Also shown in FIGS. 5G-5I is support frame covering 15, which in some embodiments, may function in part to properly position the valve clasper relative to the support frame.

Figure 5J:
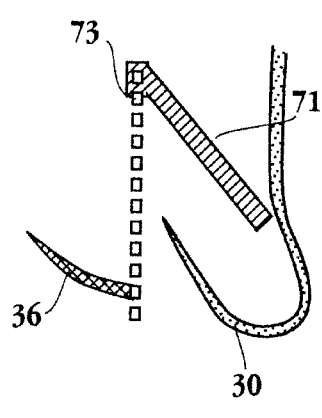
FIG. 5J is a transverse view of one embodiment of a valve clasper movably connected to a prosthetic valve support frame structure in its compact condition in situ. The valve clasper is in an engagement position.
Figure 5K:
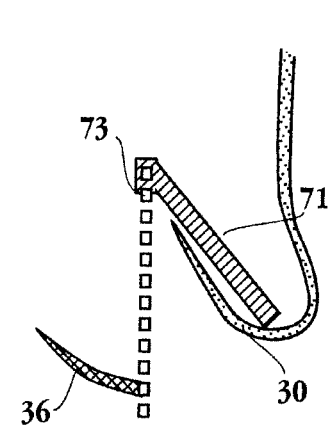
FIG. 5K is a transverse view of one embodiment of a valve clasper movably connected to a prosthetic valve support frame structure in its expanded condition in situ. The valve clasper is in a nested position.
Figure 5L:
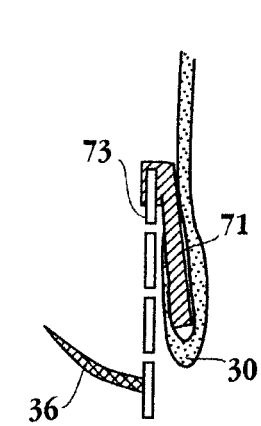
FIG. 5L is a transverse view of one embodiment of a valve clasper movably connected to a prosthetic valve support frame structure in its compact condition in situ.

In an alternative embodiment, valve clasper 71 is fixed (e.g., adhered to or welded to) a support frame 73 of a valve prosthesis. FIG. 5J is a transverse view showing the valve prosthesis with fixed clasper 71 in an engagement position above the native valve. In FIG. 5K, the valve prosthesis is moved to a nesting position, while in FIG. 5L, support frame 73 is expanded radially to an expanded condition, and valve clasper 71 is sandwiched between the native valve leaflet and support frame 73.

Figure 6A:
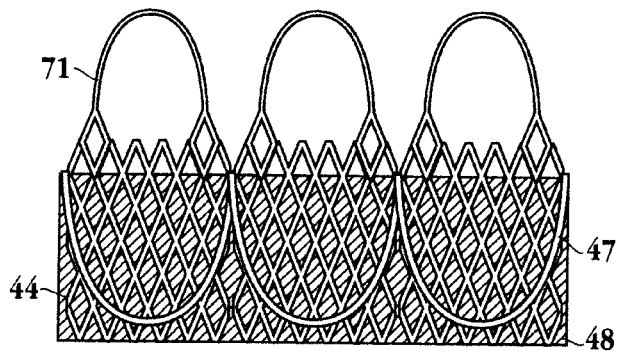
FIG. 6A illustrates a valve prosthesis support frame in a flat form with a plurality of valve claspers fixed to the support frame, a plurality of prosthetic leaflet suture lines and a covering.
Figure 6B:
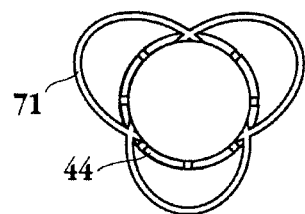
FIG. 6B illustrates the top view of a valve prosthesis support frame with a plurality of valve claspers in which the plurality of valve claspers are fixed to the support frame and the valve prosthesis support frame is in its compact condition.
Figure 6C:
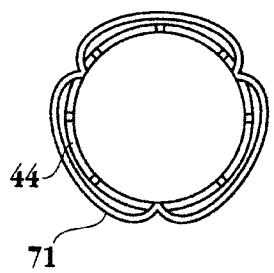
FIG. 6C shows the top view of a valve prosthesis support frame with a plurality of valve claspers in which the plurality of valve claspers are fixed to the support frame and the valve prosthesis support frame is in its expanded condition.

The alternative embodiment, wherein the plurality of valve claspers, such as valve clasper 71 which is representative, are fixed to the support frame 44 of the valve prosthesis, is shown in FIGS. 6A-6C. In this embodiment, each valve clasper is directly fixed to the support frame, for example, by welding. In other embodiments, the valve claspers are manufactured as part of support frame 44. The valve prosthesis, shown in FIG. 6A in a rolled out view, also shows a line 47 at which prosthetic heart valves are secured to the support frame, and an optional covering 48 on the support frame.

FIG. 6B is a top view of valve support frame 44 with valve clasper 71 wherein valve clasper 71 is permanently fixed to the support frame and wherein support frame 44 is in a compact condition. FIG. 6C shows the same valve support frame with clasper in which the support frame is in an expanded condition.

Figure 7A:
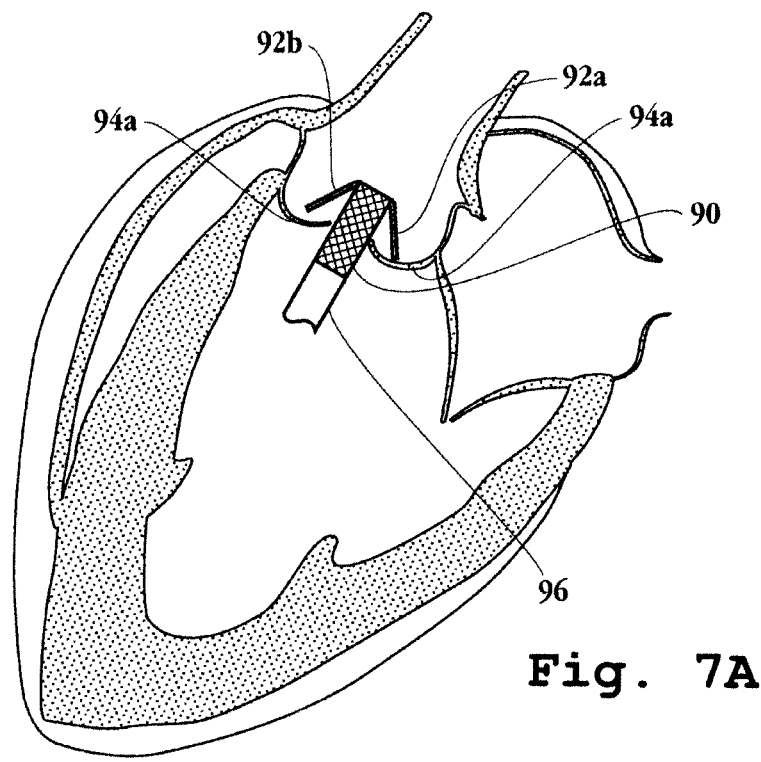
FIG. 7A showed a valve prosthesis with a sheath in situ wherein the support frame is in a compact condition and the valve claspers are in a nested position.
Figure 7B:
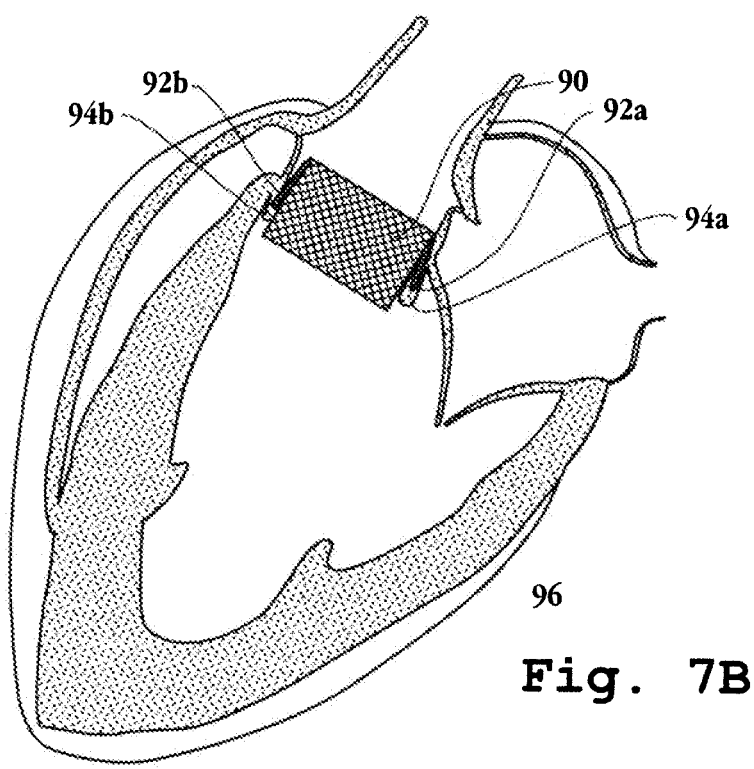
FIG. 7B illustrates a prosthetic valve with movably connected claspers deployed in a native cardiac valve.

FIGS. 7A and 7B illustrate a sutureless valve prosthesis with movably connected claspers in situ. In FIG. 7A, support frame 90 is in a compact condition and encased by sheath 96, and valve claspers 92 are in a nested position prior to radial expansion of the support frame within the native valve. Native valve leaflets are shown as 94a. A portion of the implantation device is shown as 96. The engaging portion of the valve clasper, e.g., the u-shaped member or curved portion, has contacted, or engaged, the native valve sinus. FIG. 7B shows the same valve in which the support frame is in its expanded condition, after valve delivery and deployment and after removal of a valve delivery device. Native heart valve leaflets 94b are sandwiched between the valve claspers and the support frame to facilitate anchoring of the valve prosthesis in the heart annulus. It is understood that the positioning of the support frame in which native heart valve leaflets 94b are sandwiched between valve claspers of a valve prosthesis and the prosthesis support frame is applicable to all coronary valves (i.e., aortic, pulmonary, tricuspid and mitral). It is understood that in some embodiments, the number of valve claspers will equal of the number of native leaflets 94a within the native valve being treated.

The valve prostheses as described herein may be used in various aspects of implantation devices described herein or in any method or device known by one with ordinary skill in the art to implant a valve prosthesis into a subject.

II. Implantation Devices for Delivery of a Prosthetic Aortic. Pulmonary or Mitral Valve In a third aspect, an implantation device for delivery of a valve prosthesis is provided. In a general embodiment, the implantation device is comprised of a valve prosthesis, such as valve prosthesis 2 described above, and a delivery device, now to be described.

In one embodiment of a implantation device and illustrated in FIGS. 8A-8H and FIGS. 9A-9Q, implantation device 100 is designed, for example, for apical (antegrade) delivery of an aortic heart valve prosthesis, percutaneous delivery of a pulmonary valve prosthesis through the superior vena cava, or delivery of a mitral valve prosthesis or pulmonary valve prosthesis through the inferior vena cava. These minimally invasive procedures are readily understood by a person with ordinary skill in the art.

In one embodiment of an implantation device and illustrated in FIGS. 8A-8H and FIGS. 9A-9Q, implantation device 100 is designed for apical delivery of an aortic heart valve prosthesis. Implantation device 100 includes a control unit, generally indicated in FIG. 8A by 250, and in one embodiment comprises several separate and independent controllers, described below.

Delivery device 100 comprises a first sheath 120 which fully or partially encases a prosthetic valve support frame, e.g., support frame 102, in a compact condition and a second sheath 130 which is located distal to first sheath 120 and encases at least one valve clasper, e.g., valve clasper 106. In one embodiment, delivery device 100 further comprises a track wire controller 200 (alternatively called a track cable controller) which is located proximal to first sheath 120. In another embodiment, delivery device 100 further comprises at least one track wire 150 (alternatively called a track cable) which extends distally from track wire controller 200 and may contact the proximal ends of the valve clasper leg members. In one embodiment, track wire controller 200 comprises at least one release switch 210 which is attached to the proximal end of the at least one track wire. In some embodiments, delivery device 100 does not have a second sheath. The delivery device is designed with a hollow center to allow insertion of a guidewire 110 along which the delivery device may be advanced for delivery of the valve prosthesis.

First sheath 120 is cylindrical in shape and is hollow. The first sheath may be straight or curved. The length and flexibility of the first sheath will vary according to the delivery method as would easily be understood by a skilled artisan. For example, delivery of the valve prosthesis through the femoral artery requires a flexible sheath which is long enough to extend from the point of entry to the native valve in need of treatment. Second sheath 130 is hollow and is mostly cylindrical in shape. The distal portion of second sheath 130 may have different shapes, such as a curved cone, or a pointed tip. In one embodiment, the distal end of second sheath 130 has an opening through with a guidewire may pass.

Figure 9I:
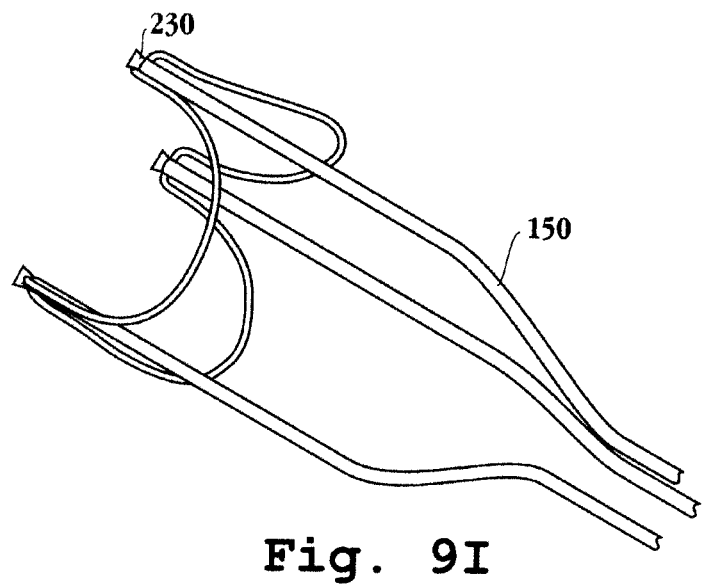
FIG. 9A-9Q provides more detailed views of one embodiment of an implantation device including cross-sectional views showing the placement of the various implantation device components within the implantation device.
Figure 9J:
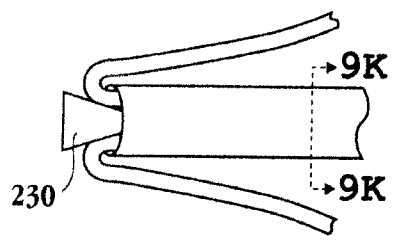
Figure 9K:
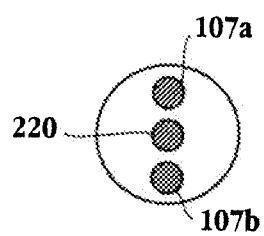
Figure 9L:
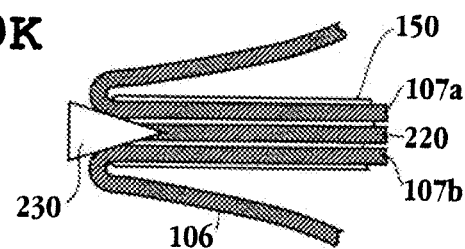

In one embodiment, the at least one track wire 150 is in contact with at least one valve clasper 106 such that the distal end of the at least one track wire 150 contacts the free end of a leg member 107 of valve clasper 106 (see FIGS. 9J-9L). In one embodiment, track wire 150 is hollow to permit, for example, insertion of one or more other cables or wires. In one exemplary embodiment, hollow track wire 150 encases a locking wire 220, seen best in FIG. 9J-9L, that extends from the approximately proximal end of the control unit to the approximately distal end of a track wire 150. In another embodiment, the locking wire is fixed at its proximal end to a locking wire support 190 (FIG. 9M). In still another embodiment, the locking wire comprises a locking member 230 at its distal end (FIG. 9L).

As shown in detail in FIGS. 9I-9L, in some embodiments, track wire 150 encases two of leg members, for example 107a and 107b in FIGS. 9K-9L, of two different, independent valve claspers 106 and locking wire 220. It will be appreciated by a person with skill in the art that this arrangement of leg members and a locking wire having a locking member results in a friction fit of the components within the track wire, thus securing leg members of two different valve claspers within a hollow track wire as long as the locking member of the locking wire is adjacent to two leg members at approximately the distal end of the track wire.

One having ordinary skill in the art can envision a variety of mechanisms whereby each of the track wires, such as track wire 150, are fixed to the control unit, track wire controller 200 and/or release switch 210. For example, the proximal ends of each of track wire 150 may be welded or glued to the various components of the control unit. Alternatively, the proximal ends of track wire 150 may each be wound around or threaded through the various components to allow greater flexibility with respect to the lengths of track wire 150.

In some embodiments, the valve prosthesis support frame is at least partially covered by a covering and a track wire is disposed between the support frame and the covering, to movably secure the track wire to one or more valve claspers and the support frame.

Figure 8A:
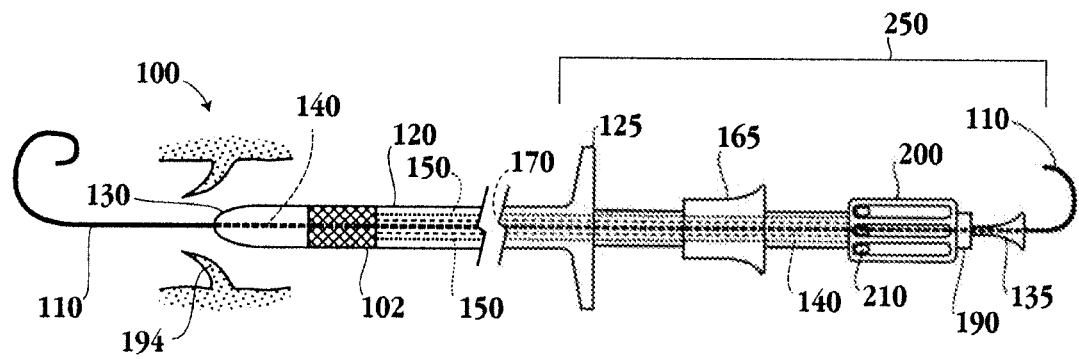
FIGS. 8A-8H are schematic illustrations of one embodiment of an implantation device and a method for implanting a valve prosthesis in a native valve of a heart.

In one embodiment, the delivery device further comprises a valve prosthesis pusher wire 170 (alternatively called a pusher cable) having a proximal end fixed to the control unit and a distal end for contact with the proximal end of valve prosthesis 102. The details of various embodiments of the pusher wire are presented in FIGS. 9M-9Q. The implantation device may comprise one, two, three, four or more valve prosthesis pusher wires. In another embodiment, the control unit of the implantation device further comprises a pusher wire controller 165 (alternatively called a pusher cable controller). In one embodiment, illustrated in FIG. 9M, the approximately proximal end of the valve prosthesis pusher wire 170 is fixed to pusher wire controller 165. The pusher wire extends from the approximately proximal end of the valve prosthesis proximally to the pusher wire controller. The valve prosthesis pusher wire may be hollow or solid and may be made of wire, plastic or other suitable materials. In another embodiment, the implantation device comprises a pusher wire support member which extends longitudinally and distally from the pusher wire controller. The pusher wire support member may vary in length and functions to allow the user to apply pressure in a distal direction to the proximal end of the valve prosthesis, using the pusher wire controller. In one embodiment, the pusher wire support member is cylindrical in shape with a longitudinal axis parallel to that of the first sheath. In another embodiment, the pusher wire support member is hollow. In yet another embodiment, at least one pusher wire is located on the external side of the pusher wire support member. In an alternative embodiment, the at least one pusher wire is located on the internal surface of the pusher wire support member. In a further embodiment, at least a portion of valve prosthesis pusher wire 170 is secured along its length to the pusher wire support member. This embodiment is shown in FIGS. 8F-8H. The pusher wire support is fixed at its proximal end to pusher wire controller 165.

In some embodiments, the distal end of valve prosthesis pusher wire 170 terminates in a pusher wire engager 175, for reversibly engaging the proximal end of the valve prosthesis. A skilled artisan will readily understand that the valve prosthesis engaging member may comprise a variety of configurations, for example, those illustrated in FIGS. 9O-9O, and may comprise, for example, one, two, three or more prongs.

One can envision the variety of mechanisms whereby each of pusher wires are fixed to, for example, the control unit or pusher wire controller 165. For example, the proximal ends of each of pusher wires may be welded or glued to the various components of the control unit. Alternatively, the proximal ends of pusher wires may each be wound around or threaded through the various components to allow greater flexibility with respect to the lengths of pusher wires.

In one embodiment, the implantation device comprises a second sheath 130 and a second sheath control cable 140 (central control cable) attached at its distal end to the second sheath. In the embodiment shown in FIG. 8F, second sheath 130 can take the form of a nose cone and is disposed distal to the first sheath. Embodiments where a second sheath is concentric with the first sheath are contemplated. The distal end of second sheath control cable 140 may be attached to the proximal or distal end of second sheath 130 or at a position between the proximal and distal ends of second sheath 130. In yet another embodiment, the proximal end of second sheath control cable 140 is fixed to a second sheath controller 135. In another embodiment, the second sheath encases each of the plurality of valve claspers, e.g., valve claspers 106, in a compact condition. The second sheath controller functions to allow the user to move the second sheath in a proximal or distal direction independent of parts of the delivery device which are not fixed to the second sheath.

The control unit allows the user to independently control various elements of the implantation device as described herein and shown in FIGS. 8A-8H. The control unit comprises a track wire control unit 200 to provide for independent control by a user of track wire 150. The one or more track wires in the device is attached at its proximal end to the track wire control unit. The distal end of at least one track wire 150 can form a contact with a leg member of valve clasper 106. Track wire control unit 200 comprises at least one release switch, such as release switch 210, and the at least one track wire is fixed at approximately its proximal end to the at least one release switch. In another embodiment, implantation device 100 comprises two track wires, each attached at its proximal end to a release switch, such as track wire 150 fixed at its proximal end to release switch 210. In yet another embodiment, implantation device 100 comprises three track wires, each attached at its proximal end to a release switch. In still another embodiment, implantation device 100 comprises four, five or more track wires, each attached at its proximal end to the same or different release switches. Each of the plurality of track wires 150 can form a contact at its distal end with one of the valve claspers 106 in the prosthetic valve, as will be described more fully below.

As noted above, at least prior to implantation, the implantation device comprises a first sheath, such as first sheath 120, that encases a valve prosthesis in its compact condition. In one embodiment, control unit 250 of implantation device 100 may further comprise a first sheath controller 125, that in the exemplary embodiment shown in FIGS. 8A-8H, is fixed to first sheath 120. In this embodiment, first sheath controller 125 has two members fixed to opposite sides of the approximately proximal end of the first sheath 120. It is understood that the first sheath controller 125 may have many shapes and one or more members which allow a user to control movement of the first sheath in the proximal or distal direction. The first sheath controller may comprise one, two, three or more members fixed to the first sheath 120. It will also be appreciated that the first sheath controller can also be positioned proximal to the first sheath, for control of the sheath by a user's hands positioned at a proximal end of the implantation device.

Valve prosthesis support frame 102 encased in a compact condition within first sheath 120 may be positioned anywhere along the longitudinal axis of first sheath 120. In one embodiment, valve prosthesis support frame 102 is positioned at and fully encased within the approximately distal end of first sheath 120, as illustrated in FIG. 9A.

In one embodiment, second sheath control cable 140 is hollow. In another embodiment, a guidewire 110 can be fed through the hollow second sheath control cable.

The control unit of the implantation device may comprise a single structural unit or multiple independent structural units. One embodiment of the control unit is illustrated in FIG. 8A. In this embodiment, control unit 250 comprises second sheath controller 135, locking wire support 190, track wire controller 200 with at least one release switch 210, pusher wire controller 165 and first sheath controller 125, each of which can be controlled independently of the others.

There are multiple alternative embodiments for means of reversibly attaching the distal end of a track wire 150 to the proximal free end of a valve clasper 106. These include locking mechanisms shown in FIGS. 10B and 10C and are well known in the art.

FIGS. 8A-8F also show the configuration of delivery device 100 as it would be used in the positioning and deployment of a valve prosthesis within a native cardiac valve structure. FIG. 8A is delivery device 100 as it is configured prior to inserting the device into the patient. The valve prosthesis is packed within the delivery device in a compact condition such that the support frame is packed within the first sheath and the valve clasper(s) are packed within the second sheath which is distal to the first sheath. As is normal practice, the guidewire is first introduced into the patient, e.g., into the femoral artery or into the left ventricle through a transapical procedure, and advanced to the appropriate heart chamber, past or beyond the native cardiac valve in need of repair.

Figure 8B:
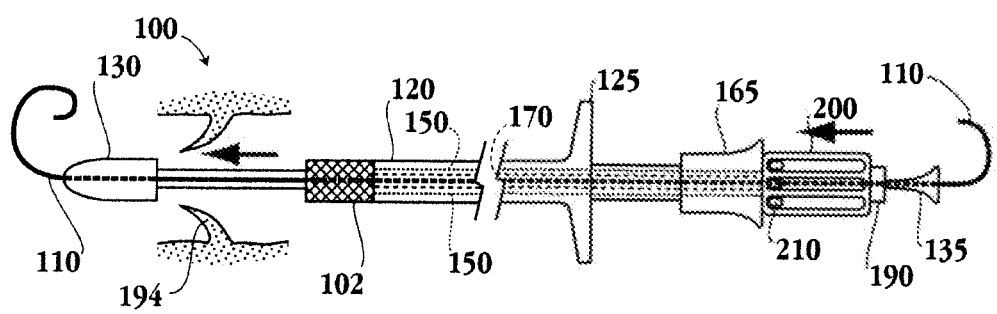

FIG. 8B shows that both the second sheath and encased claspers are moved in a in a distal direction, usually past the native valve in need of repair. The second sheath controller 135 can be used to move the second sheath, while track wire controller 200 can be used to move the claspers in concert with the second sheath. It is appreciated that in some embodiments, the delivery device may not comprise a second sheath.

Figure 8C:
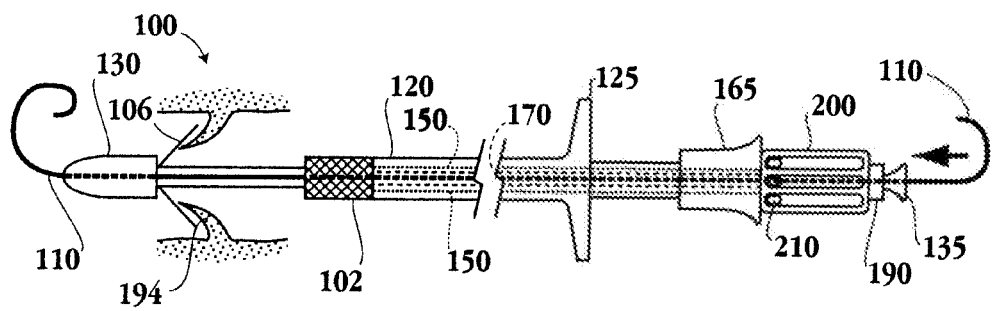

FIG. 8C shows the release of the valve claspers from the second sheath by moving the second sheath in a distal direction while holding the valve claspers stationary. It is notable that the orientation of the valve claspers as such that when they are moved in a proximal direction toward the native valve, they will "catch" on the sinus of the valve between the native leaflet 194 and the valve annulus. For this reason, it is understood that delivery device 100 is useful in delivering and deploying a valve prosthesis in a native valve wherever the device can be advance through a native valve in which the native leaflets 194 are curved away from the delivery device. For example, device 100 is useful for implanting an aortic valve through a transapical approach, or implanting a mitral valve when the device has entered the left atrium from the right atrium by way of a transapical puncture. Such methods will be discussed more fully below.

Figure 8D:
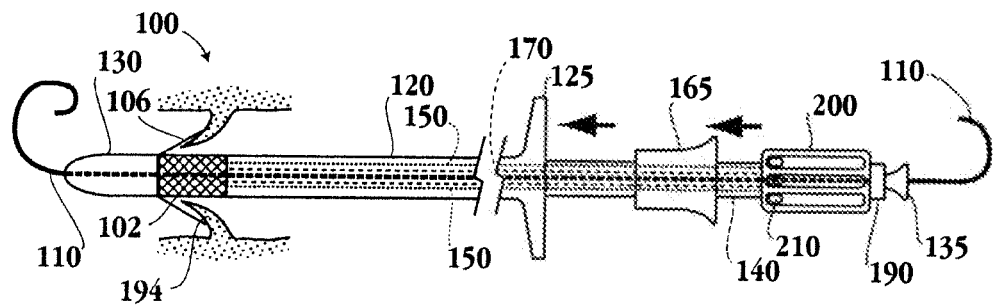

FIG. 8D shows the delivery device in which the first sheath with encased valve support frame has been pushed in a distal direction until the distal end of the valve support frame is about adjacent to the apex of the valve claspers. The length L of the valve support frame and the length L of the valve clasper leg members are such that when the distal end of the support frame abuts the apex of the valve clasper, the valve frame with leaflets 194 are in a position ready for deployment. At any time during the proximal and distal manipulations of the delivery device, the user may also rotate the device as needed for positioning the valve claspers.

Figure 8E:
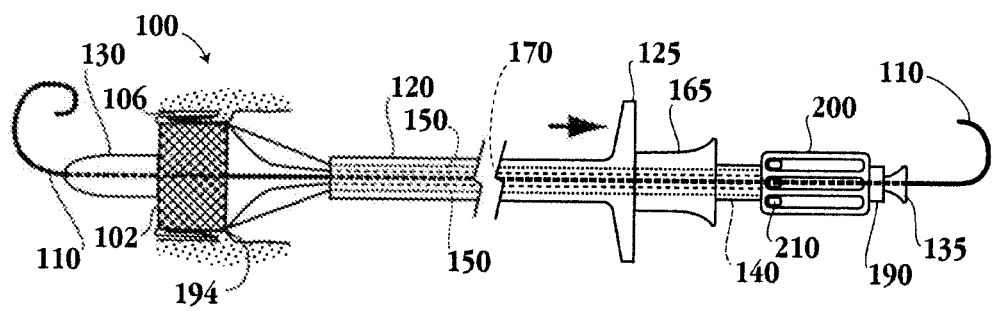
Figure 8F:
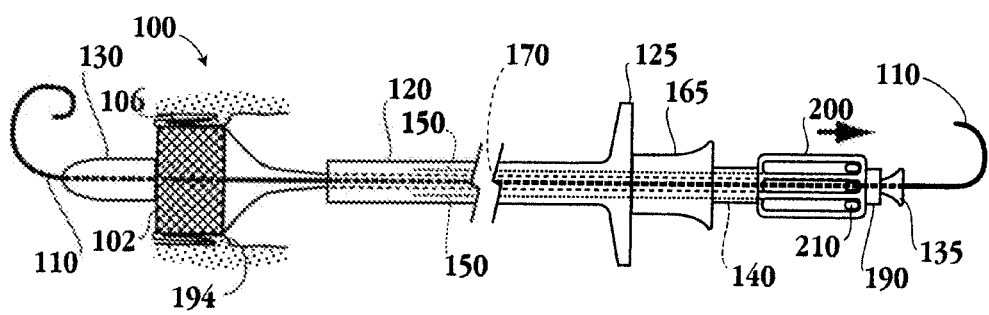
Figure 8G:
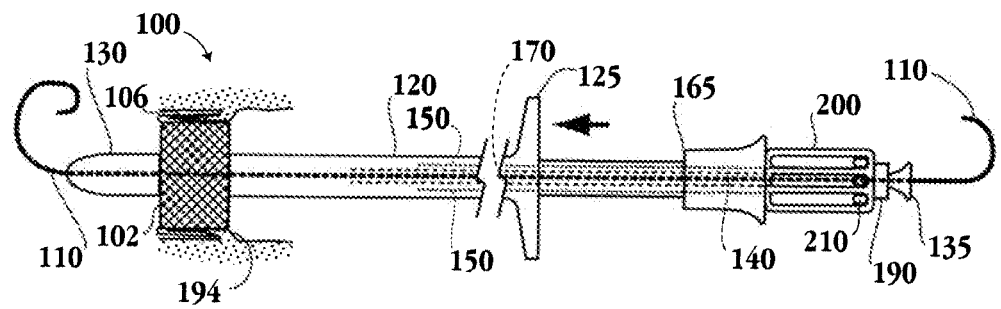
Figure 8H:
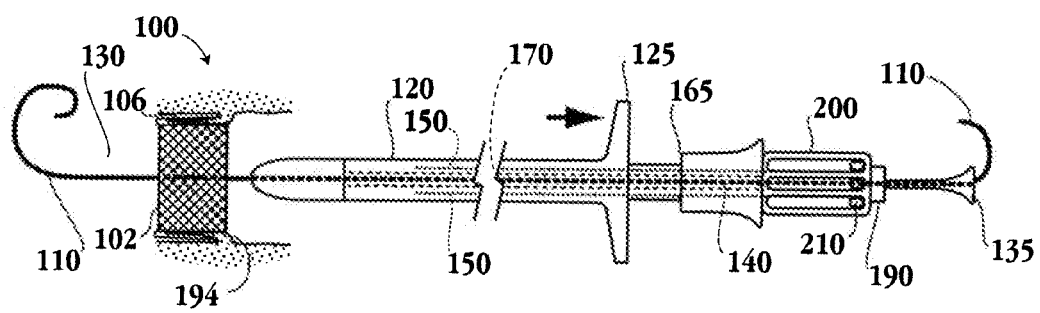

FIG. 8E shows the valve prosthesis support frame in an expanded condition. The first sheath was pulled in a proximal direction to uncover the support frame, while the valve pushers and track wires at least partially functioned to hold the valve support frame stationary. Here it shows that the first sheath was pulled in a proximal direction by pulling on the first sheath controller.

FIG. 8F shows that the release switches in the track wire controller have been pulled back in a proximal direction while other parts of the control unit were held steady. Pulling the release switches in a proximal direction pulls the track wires in a proximal direction, while the locking wires and locking members are stationary, thus releasing frictional force which held the leg members of the valve claspers within the track wires. At this point, the pusher wires can still be engaged with the valve support frame, as shown in FIG. 8F.

FIG. 8G shows that the pusher wire controller has been pulled in a proximal direction, thereby pulling the pusher wires proximally and they no longer are in contact with the valve support frame.

FIG. 8G also shows that the first sheath has been pushed in a distal direction until it abuts the proximal edge of the second sheath. This is an optional step which may function to protect the surrounding tissue from possible damaging contact with the proximal edge of the second sheath as the delivery device is removed from the body of the patient.

FIG. 8H shows that the second and first sheaths have been moved in a proximal direction by pulling back on the second sheath controller. One can appreciate that there are many ways in which the user may pull back on the individual components of the delivery device and the components of the delivery device control unit as the delivery device removed from the patient.

FIGS. 9B-9H provide cross-sectional views of delivery device 100 along various positions indicated in FIG. 9A. FIGS. 9I-9L show detailed views of track member 150 and locking wire 107.

Figure 31A:
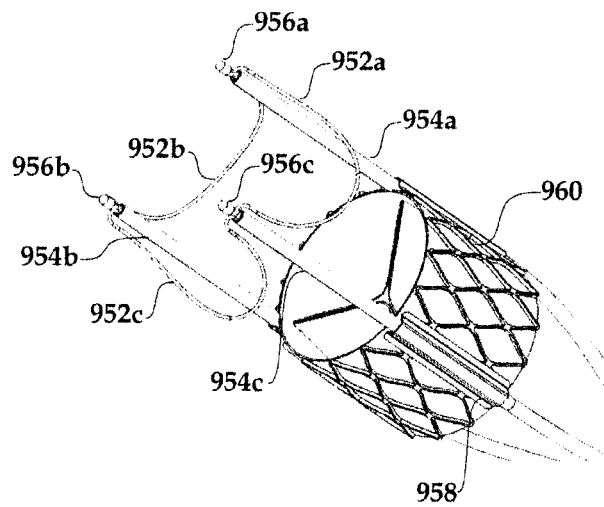
FIGS. 31A-31D illustrates a method for deploying and disconnecting from a prosthetic valve.

FIGS. 31A-31D illustrate delivery of a prosthetic valve wherein a locking wire and locking member is used to manipulate proximal and distal movements of the valve claspers. FIG. 31A represents the positioning of prosthetic support frame 960, claspers 952a,b,c, hollow track wire 954a,b,c, and locking member 956a,b,c prior to delivery and deployment of the prosthetic valve. The claspers are positioned distal to the valve support frame. Though not shown, support frame 960 is in a compacted form within a sheath as described above. Claspers 952a,b,c, may also be compacted within a separate sheath. Also shown is the optional presence of leg covering depicted by 958. The leg covering can be made from, for example, a flexible fabric as discussed in more detail below. This embodiment may have three leg coverings to cover each pair of leg members which are packed within hollow track wires 954a,b,c.

Figure 31B:
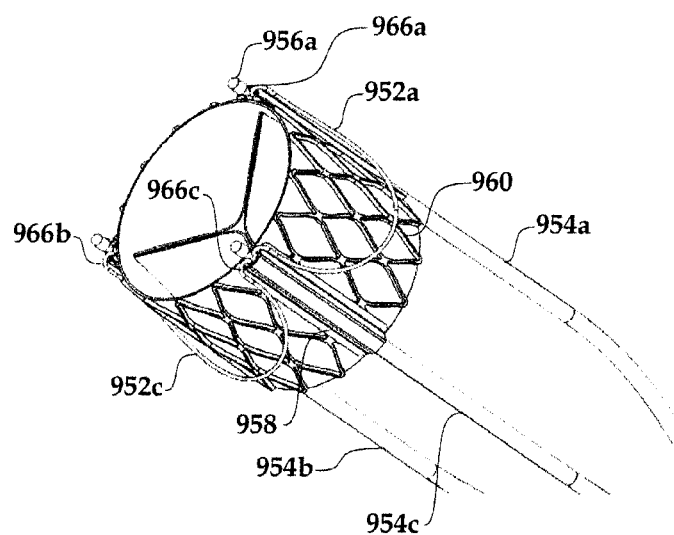
Figure 31C:
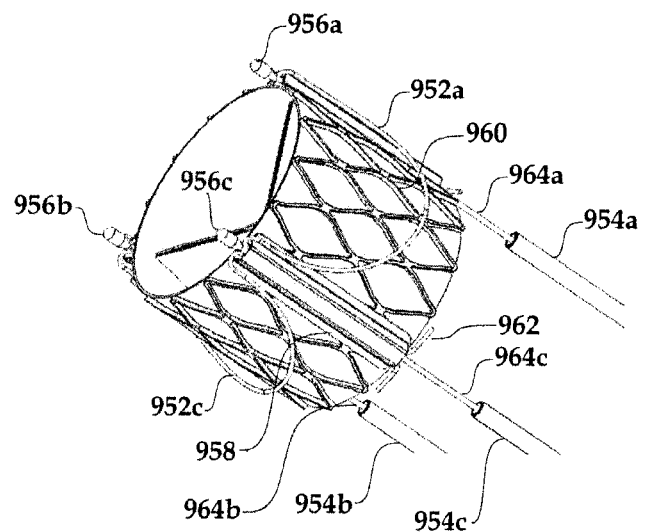
Figure 31D:
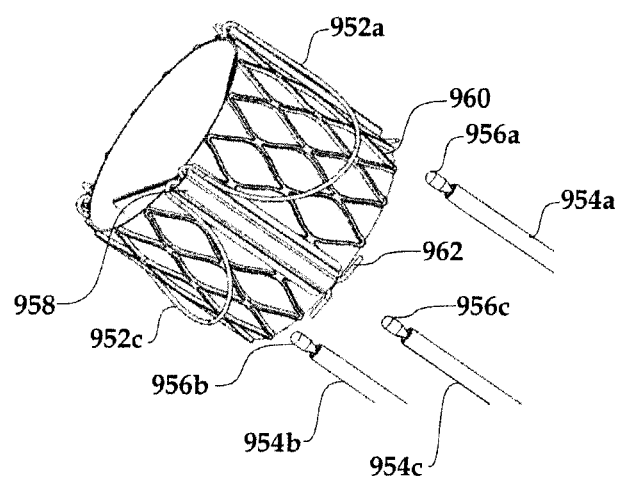

After claspers 952a,b,c, are properly positioned within the native valve sinus, for example, at the floor of the native valve sinus, support frame 960 with prosthetic leaflets is pushed in a distal direction to abut clasper apices 966a,b,c, as shown in FIG. 31B. The device provides the skilled practitioner with flexibility with respect to positioning the claspers and support frame prior to deployment. In some cases, the claspers may be positioned over the edge of the native leaflet. After deployment and expansion of support frame 960, track wires 954a,b,c are pulled in a proximal direction to uncover the free ends of leg members and each of the detents (one of which is depicted in FIGS. 31C-31D as 962), which may be made of a shape memory material, reshapes to protrude from the longitudinal axis. These detents function to create a more stable connection between the claspers and the deployed valve support frame.

As shown in FIG. 31D, locking wires (FIG. 31C, 964a, b,c) which terminate in locking members 956a,b,c, respectively, are then pulled in a proximal direction to disconnect from the deployed prosthetic valve.

Possible alternative embodiments for reversibly connecting a track wire to a valve clasper are shown in FIGS. 10A-10C, 17H-17J, 19A-19E, 20A-20C, 21A-21C and 22A-22D and are appreciated by those with skill in the art.

Figure 11A:
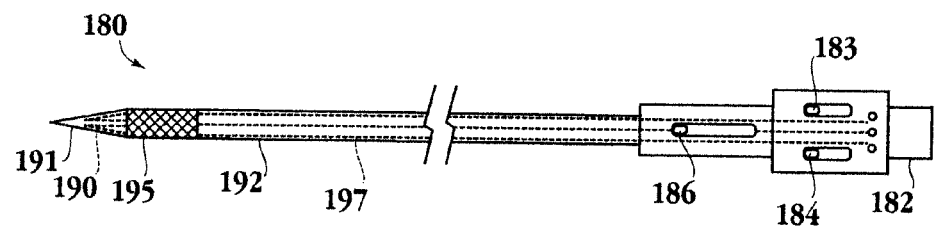
FIGS. 11A-11B illustrate one embodiment of a valve prosthesis implantation device with control unit, wherein the valve prosthesis is both in a compact condition (FIG. 11A) and an expanded condition (FIG. 11B).
Figure 11B:
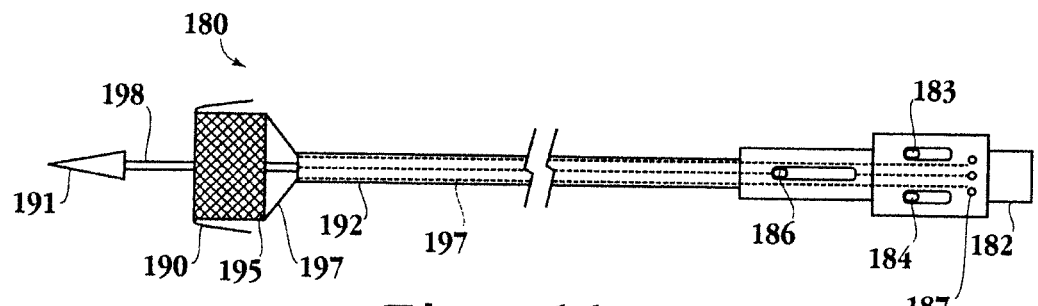
Figure 11C:
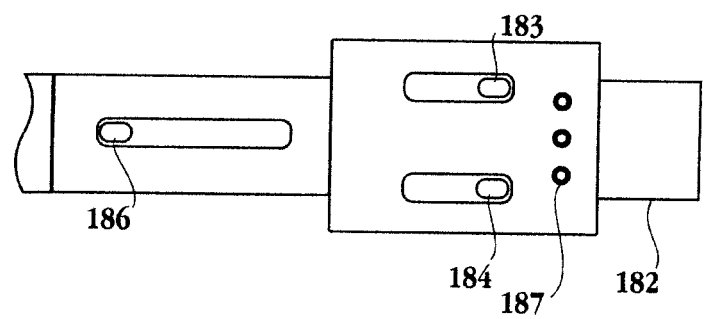
FIG. 11C illustrates one embodiment of an implantation device control unit.
Figure 11C:
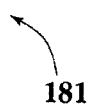

An alternative embodiment of the implantation device is an implantation device 180 for delivery of a prosthetic cardiac valve, as shown in FIGS. 11A-11C. In one embodiment, a control unit 181 comprises a clasper position controller 182 which may control rotational movement of valve claspers 190 to position the valve claspers within the native valve sinus. In another embodiment, control unit 181 further comprises a second sheath controller switch 183 (Step 1 Switch) which controls movement of a second sheath 191 (nose cone), a first sheath controller switch 184 (Step 2 Switch) which controls movement of a first sheath 192, and a valve release switch 186 (Step 3 Switch) which moves first sheath 192 to uncover the prosthetic valve 193. The first sheath encases a valve prosthesis support frame 195 and at least one track wire 197. A second sheath control cable 198 is also shown. Prior to deployment of the valve prosthesis, the delivery device is configured as shown in FIG. 11A. After radial expansion of valve prosthesis support frame 195, but prior to removal of the delivery device from the patient, the delivery device is configured in situ as shown in FIG. 11B.

In another embodiment, control unit 181 further comprises at least one release switch 187. Control unit 181 is shown in greater detail in FIG. 11C.

III. A First Implantation Device for Retrograde Delivery of an Aortic Valve Prosthesis In a fourth aspect, an implantation device 300 for delivery of an aortic valve prosthesis through the femoral artery is provided. Implantation device 300 can comprise the valve prosthesis as shown in FIG. 1B and described above, wherein each valve clasper comprises a u-shaped member.

Figure 12A:
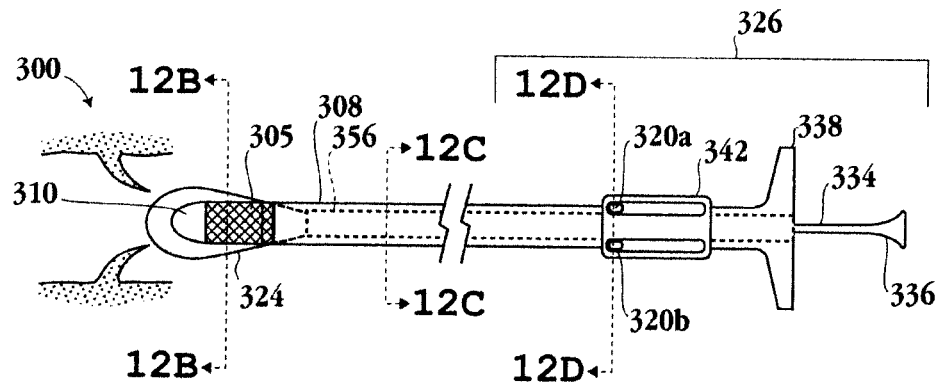
FIG. 12A illustrates one embodiment of a valve prosthesis implantation device.
Figure 12B:
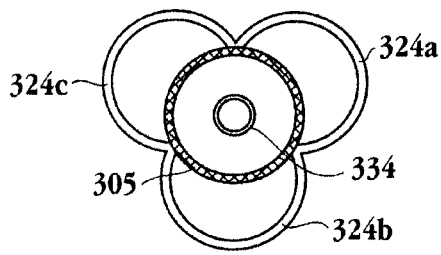
FIGS. 12B-12D provide cross-sectional views of one embodiment of a valve prosthesis implantation device.

In one embodiment of a delivery device and illustrated in FIG. 12A, implantation device 300 can be used for femoral delivery of an aortic heart valve prosthesis. In an alternative embodiment, implantation device 300 may provide for apical delivery of a mitral valve.

Implantation device 300 includes a control unit, generally indicated in FIG. 12A by 326, and in one embodiment, comprises several separate and independent controllers, described below. Control unit 326 also includes a track wire controller 342, at least one track wire 344, and a first sheath 308. The implantation device shown in FIG. 12A has three track wires.

In one embodiment, first sheath 308 at least partially encases valve clasper 324 and track wires 344. A first sheath controller 338 is fixed to the proximal end of first sheath 308. First sheath controller 338 can facilitate both proximal and distal (longitudinal) movement of the first sheath, and, optionally, rotational movement of the track wires and attached claspers to allow for proper positioning of the claspers relative to the native valve leaflets.

Figure 12C:
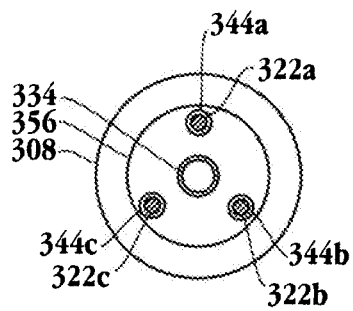
Figure 12D:
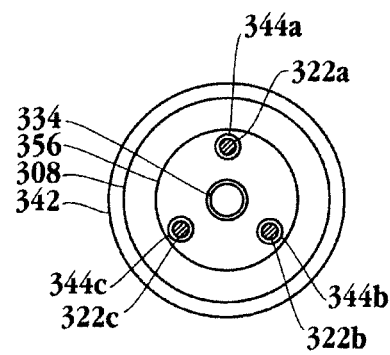

The control unit allows the user to independently control various elements of the implantation device as described herein and shown in FIG. 12A. The control unit comprises a track wire controller 342 to provide for independent control by a user of track wire 344a. The one or more track wires in device 300 is attached at its proximal end to the track wire controller. The distal end of at least one track wire, such as 344a, can form a contact with a free end of valve clasper 324. Track wire controller 342 comprises at least one release switch 320, such as release switch 320a, and the at least one track wire, such as track wire 344a, is fixed at approximately its proximal end to the at least one release switch, such as release switch 320a. In another embodiment, implantation device 300 comprises two track wires 344a and 344b, each attached at its proximal end to a release switch, such as track wire 344b fixed at its proximal end to release switch 320*b*. In yet another embodiment, implantation device 300 comprises three track wires, each attached at its proximal end to a release switch. In still another embodiment, implantation device 300 comprises four, five or more track wires, each attached at its proximal end to the same or different release switches. Each of the plurality of track wires can form a contact at its distal end with at least one of the valve claspers in the prosthetic valve, as will be described more fully below. Each of the plurality of track wires may encase one or more straight portions of a clasper leg member and/or a locking wire as depicted in FIGS. 12C-12D as 322*a,b,c*.

Implantation device 300 may further comprise a track wire support 356 which may encase the plurality of track wires 344.

Figure 13A:
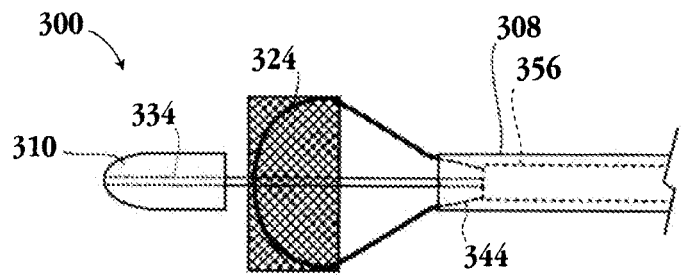
FIGS. 13A-13D provide detailed view of one embodiment of an implantation device.
Figure 13B:
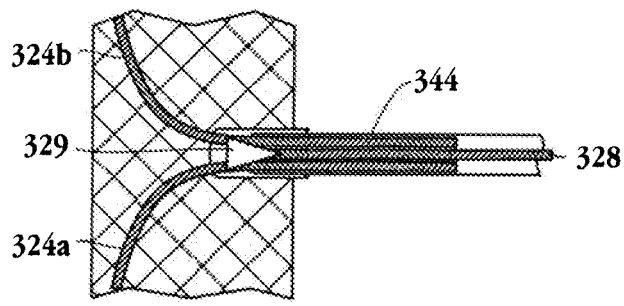
Figure 13C:
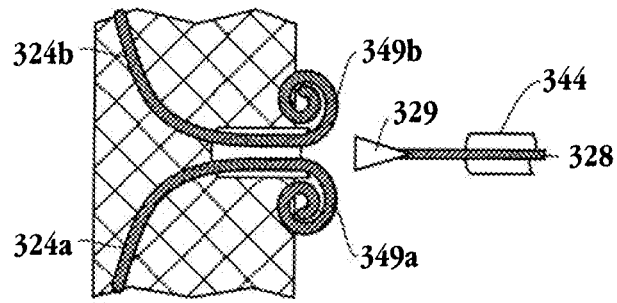
Figure 13D:
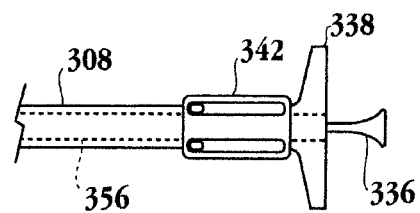

In another embodiment, the at least one track wire is in contact with the at least one valve clasper such that the distal end of the at least one track wire contacts the valve clasper (see FIG. 13B). The valve clasper of implantation device 300 comprises a u-shaped member having a curved portion and two straight portions. Each of the straight portions terminate in one free end. As shown in FIG. 13B, track wire 344 encases the straight portion and free end of two individual valve claspers 324*a,b*. In an embodiment, the track wire is hollow to permit, for example, insertion of one or more other cables or wires. In one exemplary embodiment, a hollow track wire encases a locking wire 328, as shown in FIGS. 13B and 13C, that extends from the approximately proximal end of the control unit to the approximately distal end of a track wire 344. In another embodiment, the locking wire is fixed at its proximal end to a locking wire support. In still another embodiment, the locking wire comprises a locking member 329 at its distal end (FIGS. 13B and 13C).

As shown in detail in FIG. 13B, in some embodiments, track wire 344 encases a locking wire and two straight portions of two different, independent, adjacent valve claspers, such as valve clasper 324. It will be appreciated by a person with skill in the art that this arrangement of valve claspers and a locking wire having a locking member results in a friction fit of the components within the track wire, thus securing the straight portions of two different valve claspers within a hollow track wire as long as the locking wire with the locking member is approximately adjacent to two leg members at the distal end of the track wire. Movement of the track wire independent of the locking wire, such that the track wire is moved proximally in relation to the locking wire, results in loss of the friction fit, allowing the valve claspers to be released from the hollow track wire.

One having ordinary skill in the art can envision a variety of mechanisms whereby each of the track wires, such as track wire 344*a*, are fixed to the control unit, track wire controller 342 and/or release switch 320. For example, the proximal ends of each of track wire 344 may be welded or glued to the various components of the control unit. Alternatively, the proximal ends of track wire 344 may each be wound around or threaded through the various components to allow greater flexibility with respect to the lengths of track wire 344.

In some embodiments, a valve prosthesis support frame, such as valve prosthesis support frame 305, is at least partially covered by a covering and the valve clasper is movably fixed to the valve prosthesis support frame by threading the free ends of valve clasper 324 through the covering. In this configuration, the curved portion of the valve clasper is external to support frame covering.

Implantation device 300 further comprises a second sheath, such as second sheath 310, which encases a valve prosthesis support frame in its compact condition. Implantation device 300 still further comprises a second sheath control cable 334 which is fixed at its distal end to a portion of the internal surface of the distal end of second sheath 310. In yet another embodiment, the approximately proximal end of second sheath control cable 334 is fixed to a second sheath controller 336. The second sheath controller facilitates the user in moving the second sheath control cable, and thereby the second sheath, in a proximal or distal direction. This movement may or may not be done independently of other parts of the implantation device.

In one embodiment, second sheath control cable 334 is hollow. In yet another embodiment, a guidewire can be fed through the hollow second sheath control cable.

In another embodiment, the second sheath at least partially encases the curved portion of each of valve claspers 324 in a compact condition prior to deployment of the valve prosthesis.

FIG. 13C shows the embodiment wherein the free ends of the valve claspers terminate in a detent 349*a,b*, which can be made of a shape memory material. In this drawing, after release of the valve claspers 324*a,b* from the track wires, the detents coil. This reshaping of the detents provide a structural component which can function to enhance securing of the claspers of the deployed valve prosthesis to the support frame.

Figure 14A:
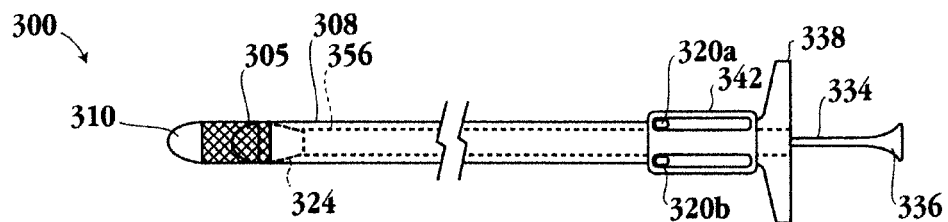
FIGS. 14A-14D illustrate manipulation steps for one embodiment of an implantation device.

FIGS. 14A and 29B-29H show manipulations of implantation device 300 as it is used to deliver and deploy a valve prosthesis in the patient. FIG. 14A shows the implantation device prior to insertion into the patient. Second sheath 310 is then advanced through, for example, the femoral artery to the aortic valve until the second sheath, which encases valve prosthesis support frame 305 in a compact condition, is positioned within the native valve. This initial positioning of the support frame may be done using an imaging system as is understood by the skilled artisan.

Figure 14B:
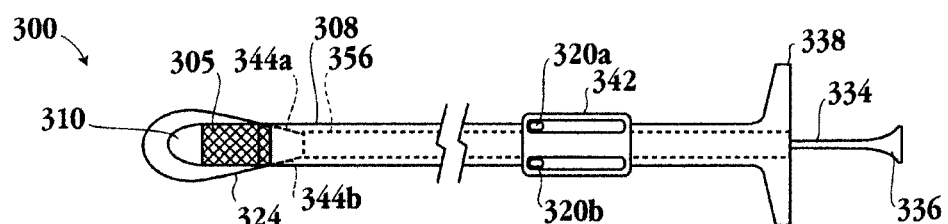

FIG. 14B illustrates the implantation device wherein the u-shaped members of the valve claspers have been released from the second sheath and the track wires have been pushed in a distal direction. The track wires can be pushed in a distal direction by moving the track wire controller in a distal direction. Notably, in this embodiment, a covering covers the valve prosthesis support frame and the straight members of each valve clasper have been threaded through the proximal end of the covering such that the curved portion of the valve clasper which will engage the native valve sinus, is positioned external to the support frame covering. Accordingly, as the track wires are pushed in a distal direction, the valve claspers remain movably attached to the distal end of the valve prosthesis support frame, however, the distal end of each valve clasper can radially extend from the compact support frame.

Figure 14C:
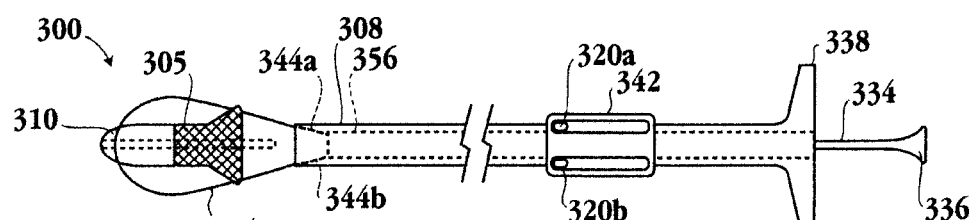

FIG. 14C shows that second sheath 310 is pushed in a distal direction to only partially uncover the valve prosthesis support frame. The partial uncovering is an optional step which may function to minimize undesired movement of the support frame out of the targeted position. Alternatively, the second sheath may be pushed in a distal direction to fully undercover the valve prosthesis support frame. The second sheath can be moved distally by pushing second sheath controller 336 distally.

Figure 14D:
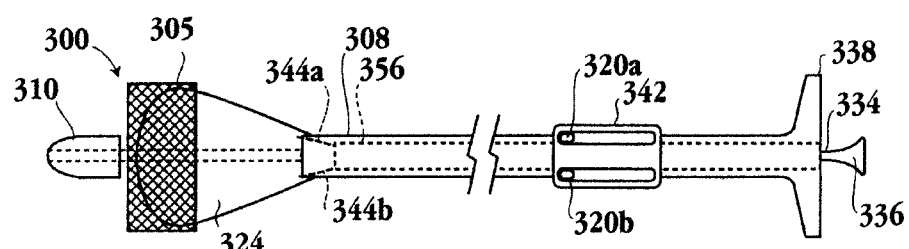

FIG. 14D shows that second sheath 310 has been pushed in a distal direction to fully uncover the valve prosthesis support frame, allowing the support frame to fully expand to its expanded condition. At this time, the valve claspers are positioned concentric to the support frame, and the native valve leaflets are disposed between the valve claspers and the support frame, thereby further anchoring the valve prosthesis within the native valve.

IV. A Second Implantation Device for Femoral Delivery

Figure 15A:
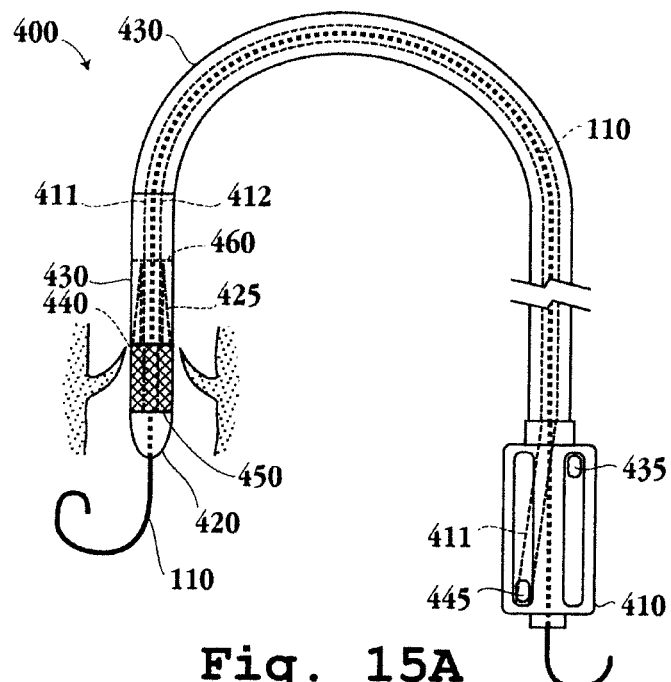
FIGS. 15A-15C illustrate manipulation steps for one embodiment of an implantation device.
Figure 15B:
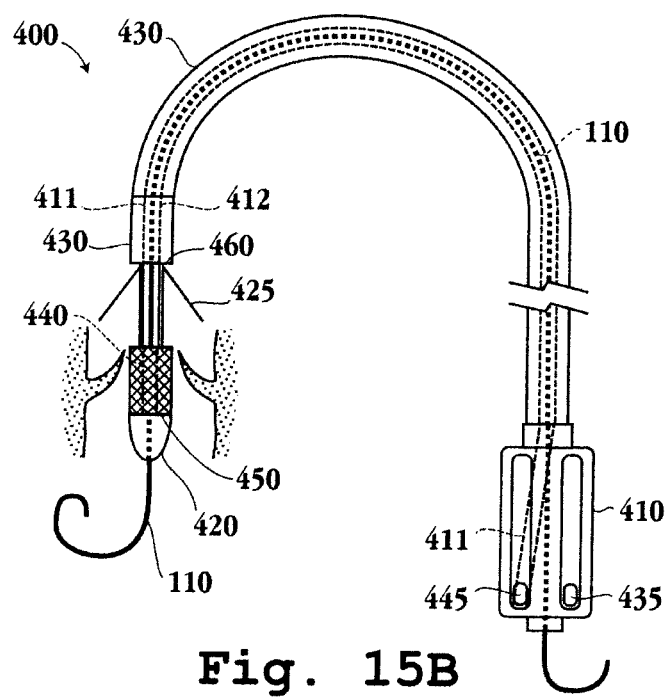
Figure 15C:
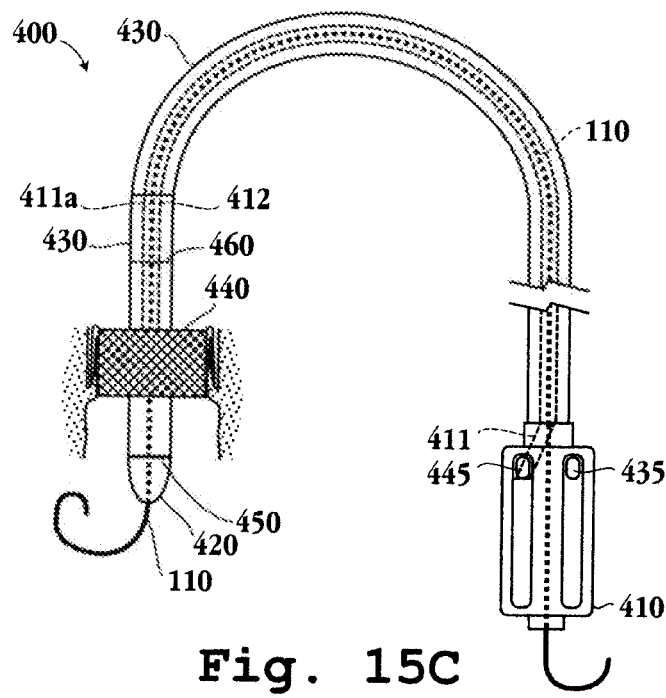

In a fifth aspect, and with reference to FIG. 15A, an implantation device 400 comprising a valve prosthesis support frame 440 with at least one clasper 425 which is movably connected to the valve prosthesis, and a delivery device comprising a control unit 410, a first sheath 410 encasing the valve prosthesis support frame 440 in a compact condition, a second sheath 430 encasing the valve claspers in a compact condition, a first sheath control cable 411 fixed to a first sheath control switch 445, and a second sheath control cable 412 fixed to a second sheath control switch 435, is provided. Embodiments of a valve prosthesis with valve claspers is described above. Methods for using the implantation device for femoral delivery of an aortic valve prosthesis is illustrated in FIGS. 15A-15C and discussed in more detail below.

The control units for the above-described delivery devices function at least in part to facilitate independent control of the various components of the implantation device, including track wires, pusher wires, and/or first and second sheaths. Persons having ordinary skill in the art understand that each of the various components (e.g., first sheath, second sheath, track wires, locking wires, pusher wires) which may be moved proximally or distally along the longitudinal axis of the implantation device, can be attached directly or indirectly to the control unit of the implantation device. The above described embodiments provide examples of how the control unit elements are moved by pushing or pulling a portion of the control unit in a distal or proximal direction, respectively. Such pushing and pulling is accomplished by using, for example, a switch connected to a wire, or pushing or pulling a handle which may be part of, for example, a sheath.

In an alternative embodiment, the control unit may comprise one or more dial portions wherein individual movable components of the implantation device (e.g., first sheath, second sheath, track wires, locking wires, pusher wires) may be moved proximally or distally by rotating a dial. In this embodiment, separate sections of the control unit may be connected or coupled such each section includes complementary threads for an adjacent section such as to allow for threaded engagement of the two sections. Accordingly, clockwise or counterclockwise rotation of one threaded section will produce distal or proximal longitudinal movement of that section relative to an adjacent threaded section. It is understood that a single implantation device control unit may comprise both rotational control elements such as the threaded sections, and control elements such as switches and handles that are moved along the longitudinal axis.

V. Alternative Valve Embodiments

Figure 16A:
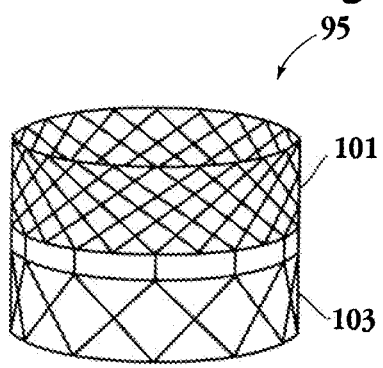
FIGS. 16A-16C illustrate an alternative embodiment for a valve prosthesis support frame.
Figure 16B:
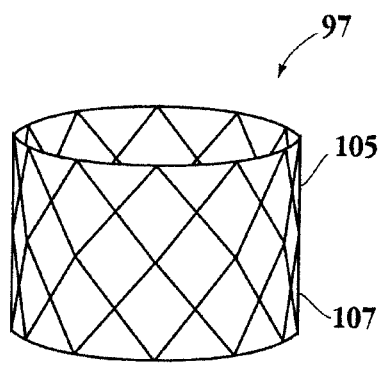
Figure 16C:
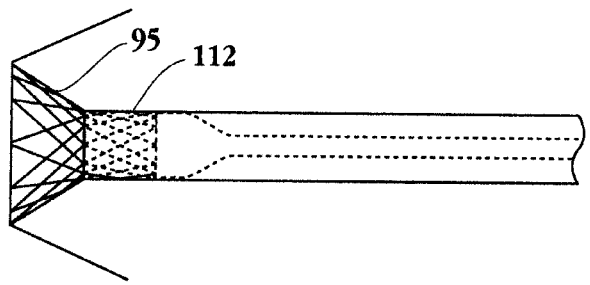

In an alternative embodiment of the valve prosthesis support frames as they may be used with the implantation devices disclosed herein, FIG. 16A depicts a valve prosthesis support frame which can be manufactured in separate units to make a single support frame 95 comprising a distal portion 101 and a proximal portion 103 wherein distal portion 101 can expand independently of proximal portion 103 (see FIG. 16A). Alternatively, as shown in FIG. 16B, a single support frame 97 is manufactured as a single unit in such a way that a distal portion 105 can expand independently of a proximal portion 107. Accordingly, as shown in FIG. 16C, a first sheath 112 is moved in a proximal direction to expose only a portion of valve prosthesis 95 prior to exposing and expanding the full valve prosthesis support frame. Similarly, a first sheath can be moved in a proximal direction to expose only a portion of valve prosthesis 97 prior to exposing and expanding the full valve prosthesis support frame.

It is understood that a prosthetic valve having support frame 16 as illustrated in FIGS. 1C-1D may serve as an exemplary embodiment of a support frame which can partially expand upon uncovering of only a portion of the support frame.

VI. Alternative Valve Clasper Embodiments

Figure 17A:
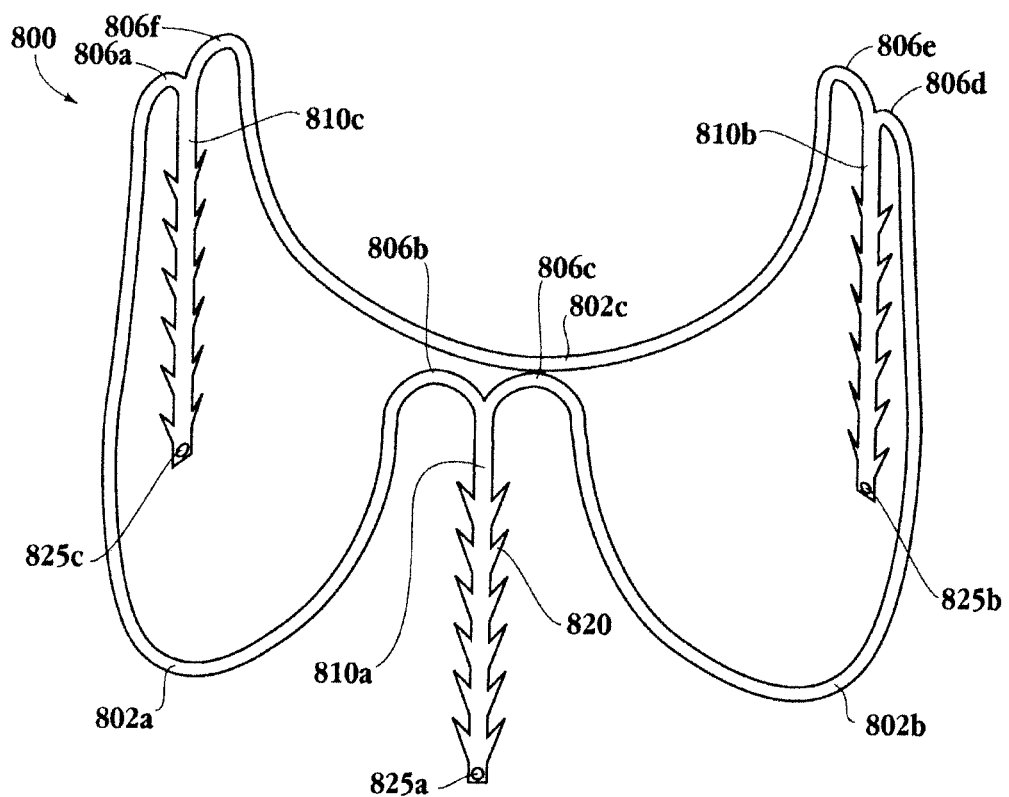
FIGS. 17A-17B illustrate alternative embodiments for clasper multiplex units.
Figure 17B:
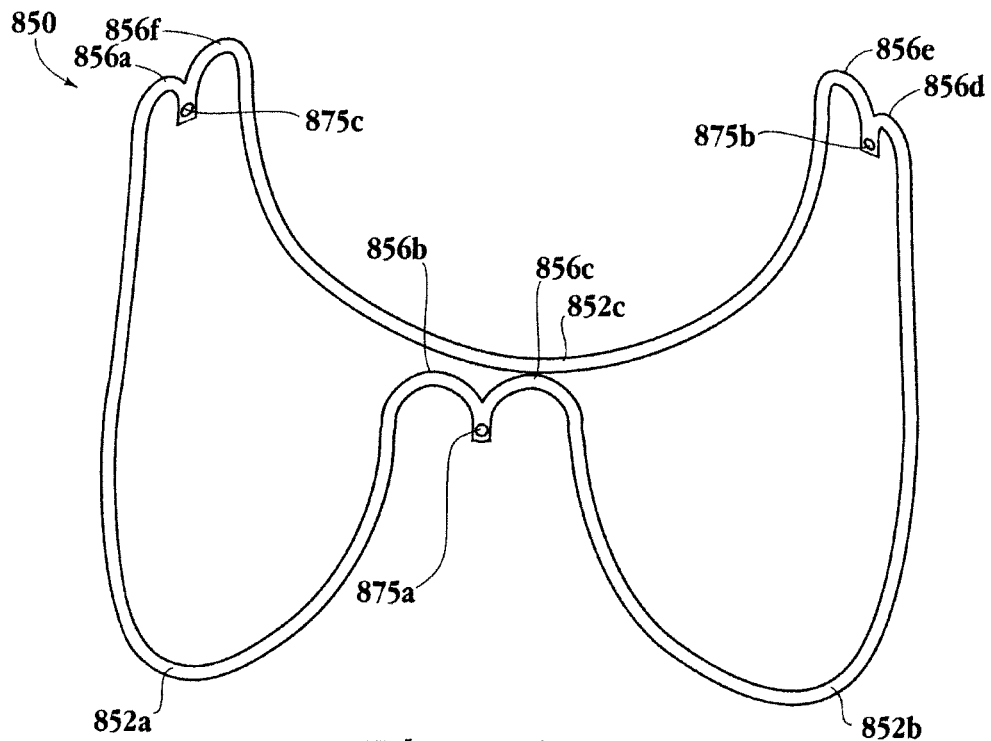

An alternative embodiment of the valve claspers is illustrated in FIGS. 17A-B. In these embodiments, each of a plurality of valve claspers is fixed to another to form a clasper multiplex unit 800. Clasper multiplex unit 800 further comprises a plurality of leg members. It is understood that there may be two, three, four or more u-shaped members attached to two, three, four or more leg members to form the clasper multiplex unit having a plurality of valve claspers. As an example, and illustrated in FIG. 17 A, u-shaped members 802a and 802b are each attached to leg member 810a, through apex 806b and 806c, respectively. Similarly, u-shaped members 802b and 802c are each attached to leg member 810b, through apex 806d and 806e, respectively. In some embodiments, the proximal end of each leg member 810a,b,c can have a hole, as illustrated in FIG. 17A, 825a,b,c. In other embodiments, there is not a hole through the proximal end of each leg member.

Figure 17C:
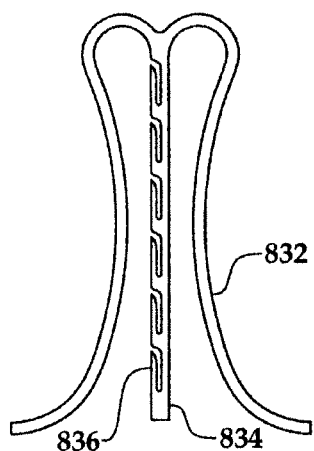
FIGS. 17C-17G illustrate alternative embodiments for the leg members of clasper multiplex units.
Figure 17D:
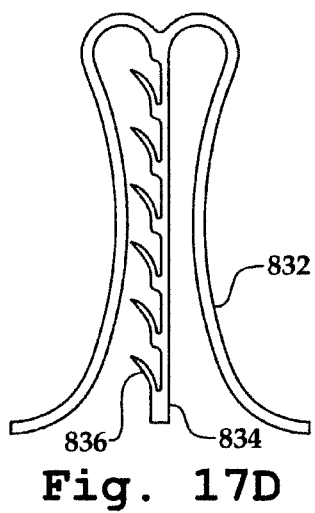
Figure 17E:
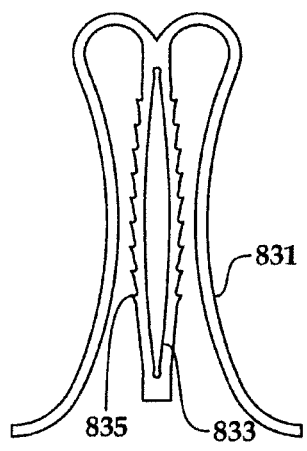
Figure 17F:
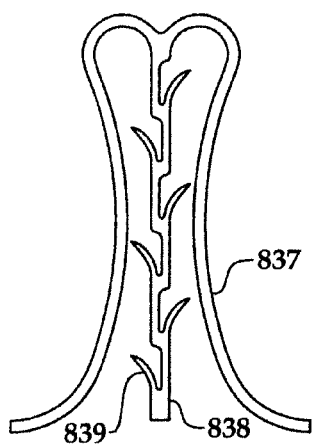
Figure 17G:
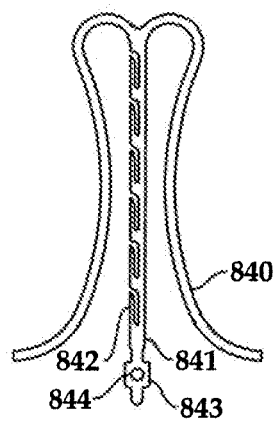
Figure 17H:
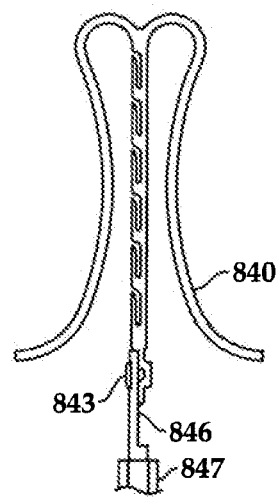
FIGS. 17H-17M illustrate alternative embodiments for attachment and release clasper multiplex unit leg members.

FIG. 17A shows an embodiment wherein leg members 810a,b,c are designed to have a plurality of barbs, such as barbs 820. These barbs may function to facilitate stabilization of the valve prosthesis after deployment within the native valve. In other words, upon deployment of the prosthetic valve, the barbs protrude such that at least one barb pierces the support frame covering and/or the leg covering if present. In a preferred embodiment, the support frame covering is attached (e.g., sewed) to the support frame. The leg covering, if present, is attached (e.g., sewed) to the support frame covering. Accordingly, if the barbs of the valve claspers pierce the support frame covering and/or the leg member covering, this will result in anchoring the valve clasper structure to the support frame structure. Alternatively, the barbs may become embedded within the support frame covering and/or the leg member covering to facilitate anchoring of the valve clasper to the support frame structure. It is understood that such anchoring elements may have any of a number of different shapes. These anchoring elements may or may not be made of a shape memory metal. The term, barb, may encompass any structural element which protrudes from the clasper and which may function to facilitate anchoring of the valve prosthesis within the native valve of the patient. It is understood by the ordinary artisan that the pattern of barbs on a leg member can be varied. For example, a series of barbs may be present along a line on one side of a leg member 834 as shown in FIG. 17C. A portion of the clasper u-shaped member is depicted as 832. Protrusion of barbs 836 upon deployment of the prosthetic valve is shown in FIG. 17D. In one embodiment, one or more leg members, with or without barbs 835 is designed to have an opening 833 as depicted in FIG. 17E. A portion of the clasper u-shaped member is depicted as 831. The size and shape of this opening may vary and is designed to make the clasper more durable. The spacing between each barb may be uniform or varied. Alternatively, as shown in FIG. 17F, each of a series of barbs 839 on a leg member 838 may be located on alternating sides of the leg member. A portion of the clasper u-shaped member is depicted as 837. The barbs may be staggered relative to one another. FIG. 17G shows optional features including a hole 844 and protrusions 843, the size and shape of each which may vary according to the required functions. In FIGS. 17G-17H, the leg member and barbs are depicted by 841 and 842, respectively and a portion of the clasper u-shaped member is shown as 840.

In another embodiment, a clasper multiplex unit 850, as shown in FIG. 17B, comprises a plurality of u-shaped members, e.g. 852a,b,c, which are attached or fixed to each other via apices 856a-f. Clasper multiplex unit 850 does not comprise leg members. In some embodiments, the clasper multiplex unit may comprise holes as shown in FIG. 17B as 875a,b,c. Each hole may provide a point of attachment for a removable leg member. In some embodiments, clasper multiplex unit 850 does not have these holes.

Figure 17I:
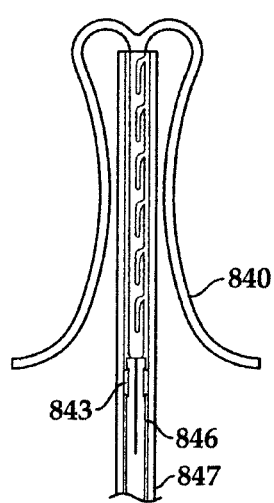
Figure 17J:
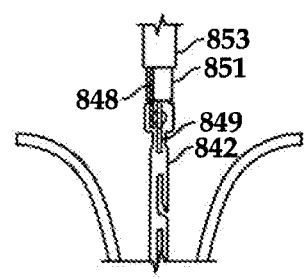
Figure 17K:
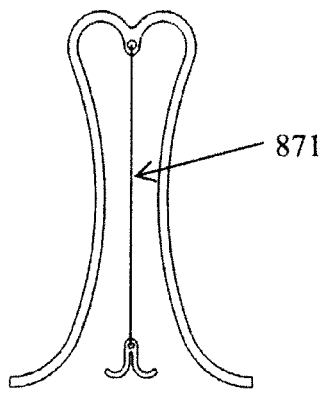
Figure 17L:
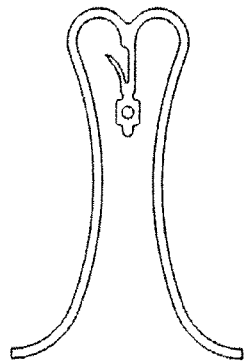
Figure 17M:
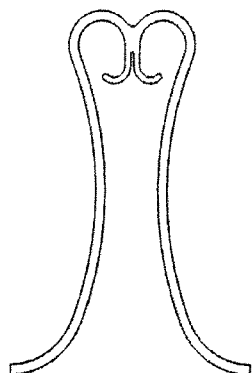

FIGS. 17K-17M provide alternative embodiments with respect to the leg members of clasper multiplex units. In each of these examples, the leg members of the clasper multiplex unit are short so as to provide increased flexibility to the functional features of the claspers. FIG. 17K illustrates a leg member connected to a flexible wire or other similar durable filament structure 871.

The clasper multiplex units and components thereof as described above and illustrated in FIGS. 17A-17M may be comprised of a shape memory metal, such as Nitinol. The u-shaped members may be capable of radial expansion away from the central axis of the unit.

Figure 18A:
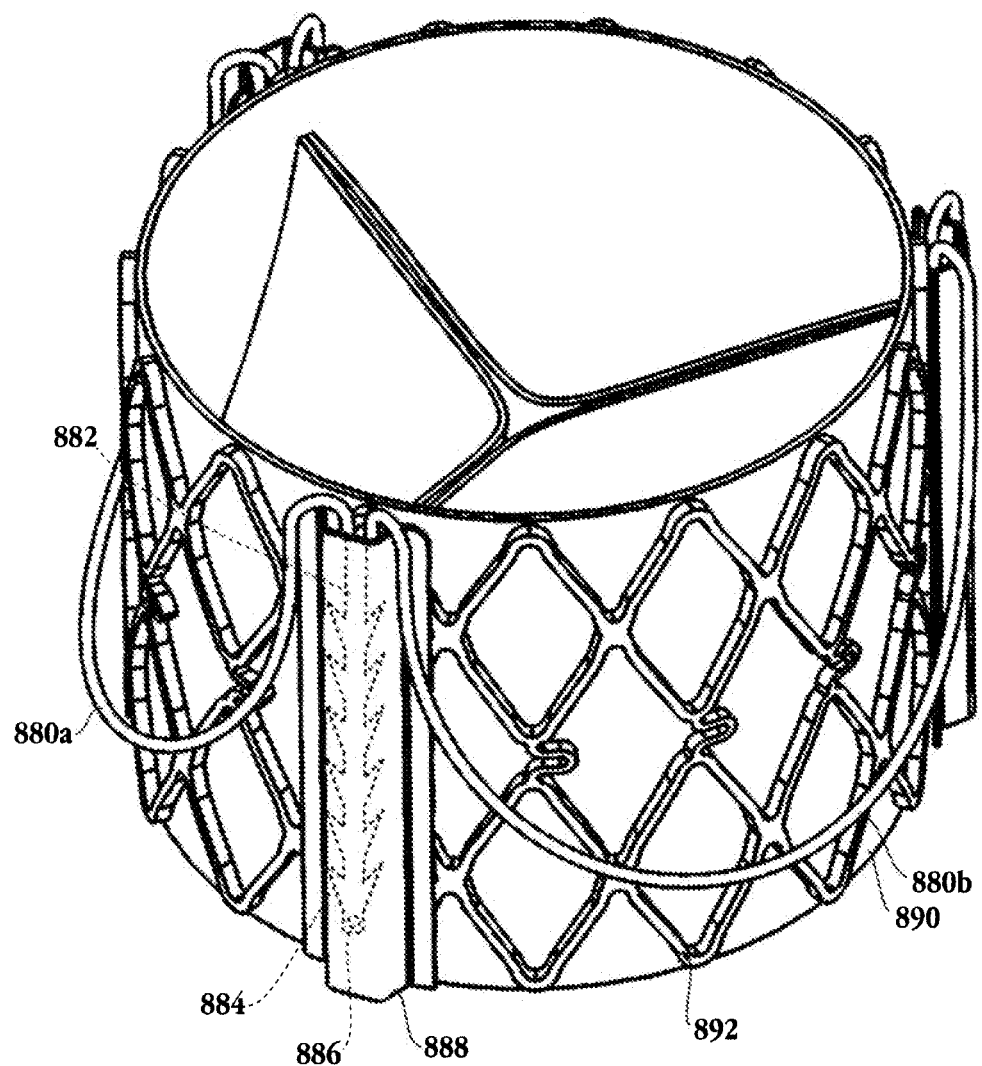
FIGS. 18A-18B illustrate alternative embodiments for a clasper multiplex unit.
Figure 18B:
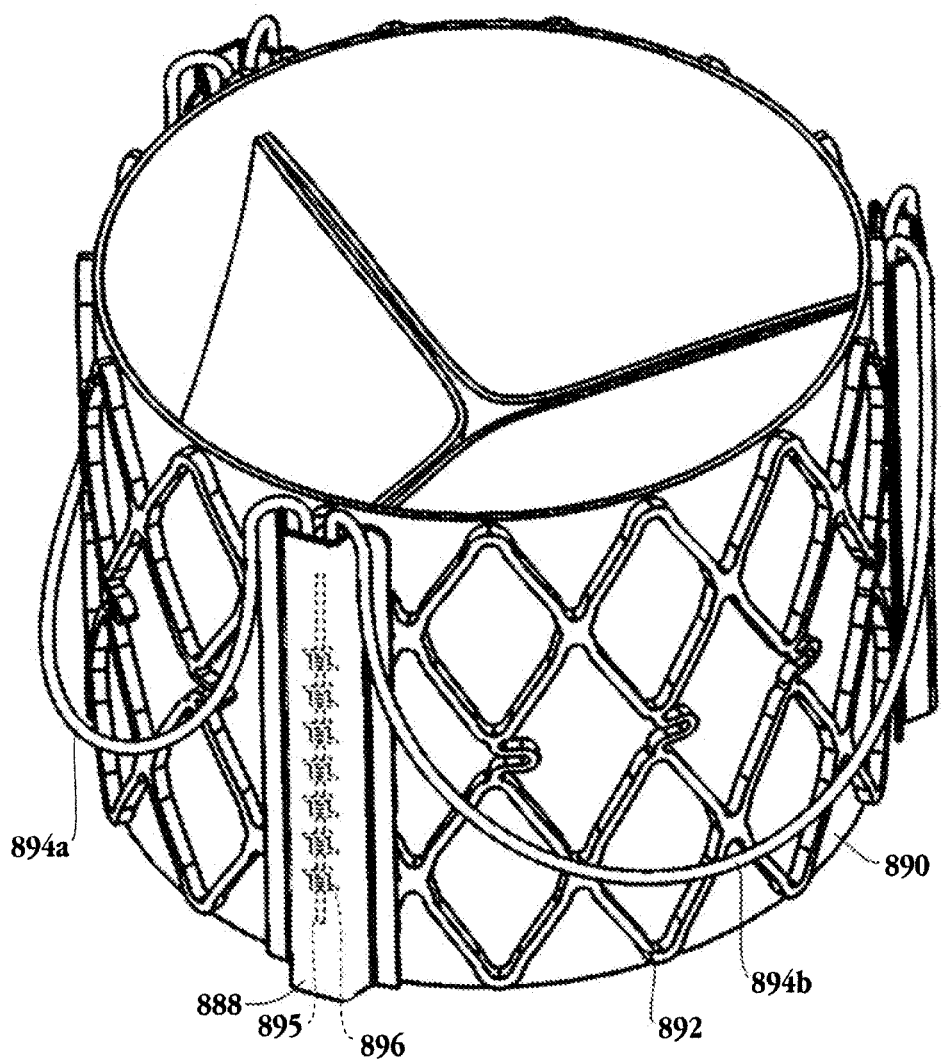
Figure 18C:
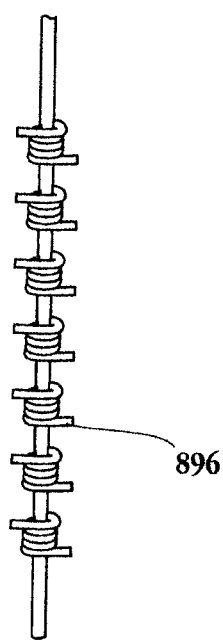
FIG. 18C illustrates an alternative embodiment for a clasper multiplex unit leg member.

FIGS. 18A-18B illustrate how a clasper multiplex unit may be positioned relative to a valve support frame. The clasper multiplex unit is not permanently fixed to valve support frame 892. The clasper multiplex unit is movably connected to the valve support frame such that the clasper multiplex unit may move in a proximal and/or distal direction along the longitudinal axis of the valve support frame. FIGS. 18A-18B also show the valve prosthesis with a covering 890 on the internal face of valve support frame 892. In some embodiments, the covering may be on the external face of the valve support frame.

FIGS. 18A-18B show an alternative embodiment wherein the valve prosthesis further comprises a leg covering 888. FIG. 18A shows a leg member 882 which has a plurality of barbs, e.g., barbs 884. FIG. 18B shows a leg member 895 having a different style of barb as depicted by 896. It is understood that leg covering 888 may or may not be present. The leg covering is preferably made of a flexible material, such that each of the barbs may easily pierce the leg covering upon deployment of the prosthetic valve. As with the prosthetic valve frame, any suitable lightweight, durable, flexible, fluid impervious, and/or biocompatible material may be utilized for the leg covering. The leg covering may be attached to the frame utilizing sutures, staples, chemical/heat bonding and/or adhesive. In some embodiments, the covering is a fabric. In further embodiments, the fabric is comprised of, for example, a material identified by a tradename selected from Nylon®, Dacron®, or Teflon®, or is expanded polytetrafluoroethylene (ePTFE), and/or other materials.

Delivery of a prosthetic heart valve as using the embodiments illustrated in FIGS. 18A-18B wherein the implantation device utilizes multiplex claspers as shown in FIGS. 18A-18B, may require alternative methods for connecting and disconnecting the multiplex claspers to and from the implantation device (e.g., track wires). While a person having ordinary skill in the art could envision several methods of connection and disconnection, alternative embodiments are provided in FIGS. 17H-17J. For example, as shown in FIG. 17H-17I, protrusions 843 may insert into an opening in a wire 846 as a means for connecting the leg member of multiplex clasper 840. This connection is stabilized when encased in a hollow track wire such as track wire 847 (FIG. 17I). FIG. 17J illustrates yet another structure for connecting and disconnecting the leg member of a multiplex clasper to the appropriate element of the implantation device. FIG. 17J shows that a flexible tension element 848 is fed through a hole at the proximal end of the multiplex clasper leg member and wrapped around the distal end of a lock and release element 849. Flexible tension element 848 is pulled in a proximal direction to secure the leg member to the appropriate element of the implantation device (a wire 851 encased by a track wire 853 in FIG. 17J).

VII. Alternative Clasper Release Mechanisms

FIGS. 19-22 illustrate alternative embodiments for the reversible attachment of the implantation device to valve claspers. FIGS. 19-20 show the use of a flexible tension element which runs along the longitudinal length of a lock and release element to provide a means of reversibly attaching a clasper multiplex unit to a valve implantation device. As shown in FIG. 19A, prior to connecting the valve implantation device to the leg members of a clasper multiplex unit, flexible tension element 902 extends along and beyond lock and release element 904. Flexible tension element 902 and lock and release element 904 are at least partially encased within a hollow track wire 906. In this example, the tension and lock and release elements are attached to the proximal end of a leg member 908 of a multiplex clasper unit. FIG. 19B shows the proximal end of lock and release element 904 and tension element 902, which may be attached to the implantation device control unit by any means which would allow independent control of each of the two elements.

Figure 19A:
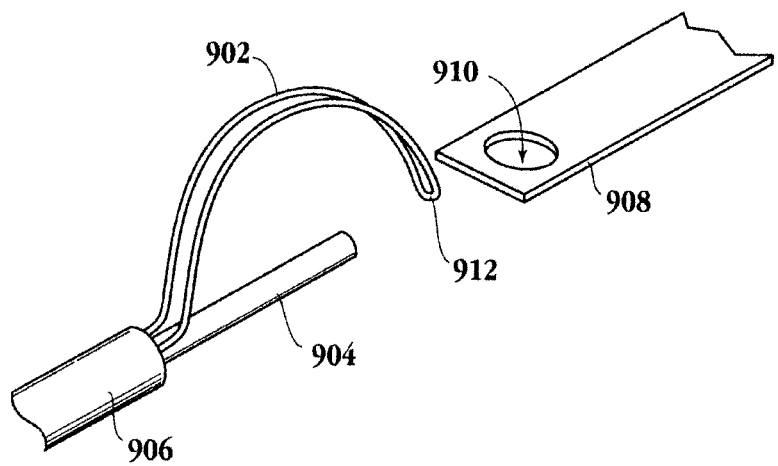
FIGS. 19A-19E illustrate an alternative embodiment for reversible attachment of a valve implantation device to a leg member of a clasper multiplex unit.
Figure 19B:
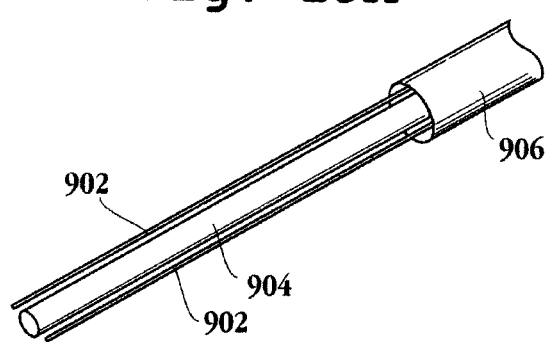
Figure 19C:
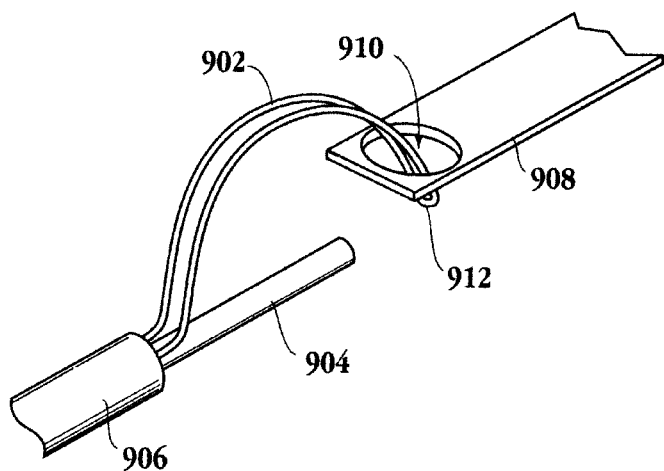
Figure 19D:
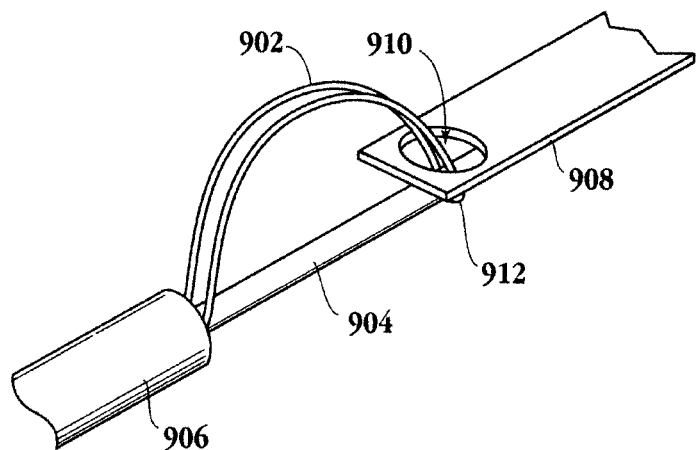
Figure 19E:
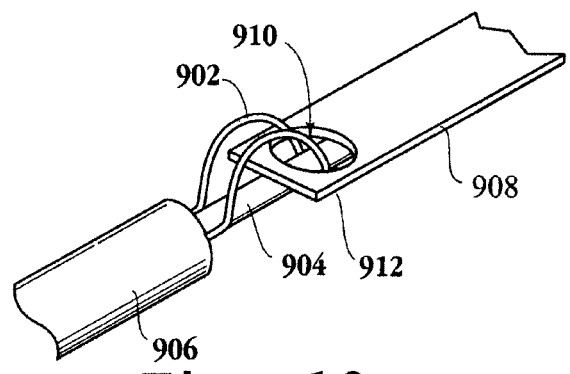

A method which may be used to attach the clasper multiplex unit to the control unit of a valve implantation device is depicted in FIGS. 19C-D. The attachment is performed prior to packing the valve prosthesis into the implantation device. A loop 912 formed at the distal end of flexible tension element 902 is fed through a hole 910 at the free end of a leg member 908 of a clasper multiplex unit. Lock and release element 904 is then moved in a distal direction independently of the flexible tension element until the distal end of the flexible tension element is pushed through loop 912 (FIG. 19D). Flexible tension element 902 can be pulled in a proximal direction in order to tighten and secure the connection between leg member 908 and the implantation device. Hollow track wire 906 is then moved distally to cover the majority of flexible tension element 902 and lock and release element 902, such that the distal end of track wire 906 is approximately adjacent to the proximal end of leg member 908 (see FIG. 19E).

Figure 20A:
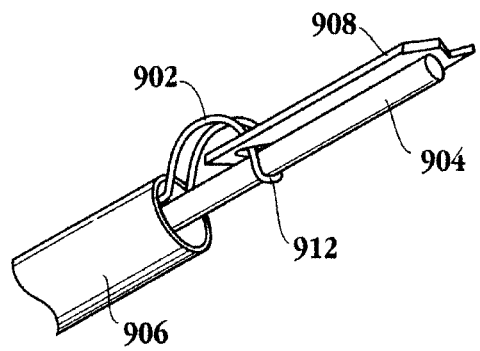
FIGS. 20A-20C illustrate an alternative embodiment for release of a valve delivery device from a leg member of a clasper multiplex unit.
Figure 20B:
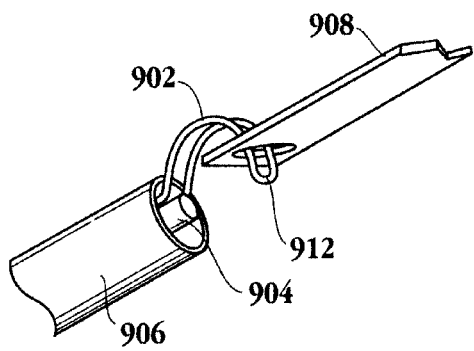
Figure 20C:
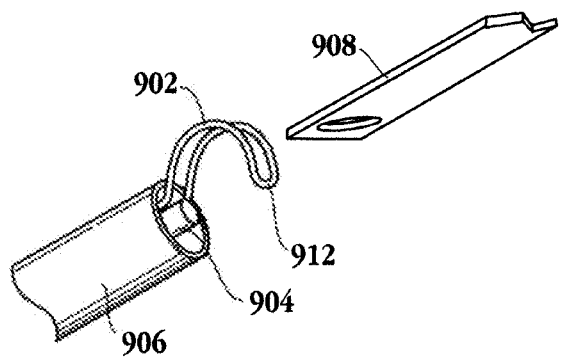

Release of a clasper multiplex unit leg member is illustrated in FIGS. 20A-C. As seen in FIG. 20A-B, lock and release element 904 is moved in a proximal direction independently of flexible tension element 902. FIG. 20C shows how track wire 906, flexible tension element 902 and lock and release element 904, are moved together in a proximal direction. Due to the flexibility of the flexible tension element, flexible tension element 902 is easily removed from hole 910 of leg member 908.

Figure 21A:
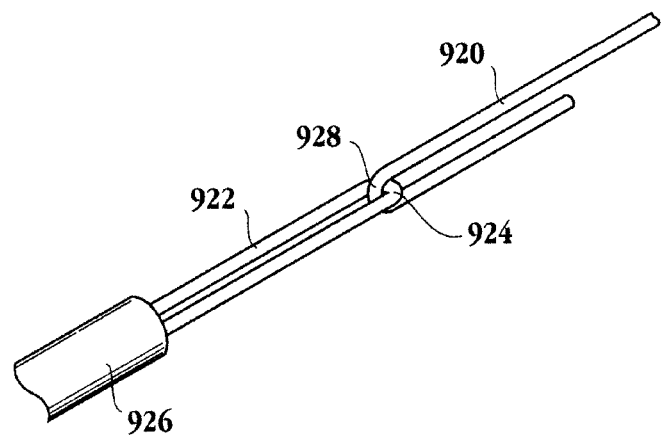
FIGS. 21A-21C illustrate an alternative embodiment for reversible attachment of a valve delivery device to a leg member of a clasper multiplex unit.
Figure 21B:
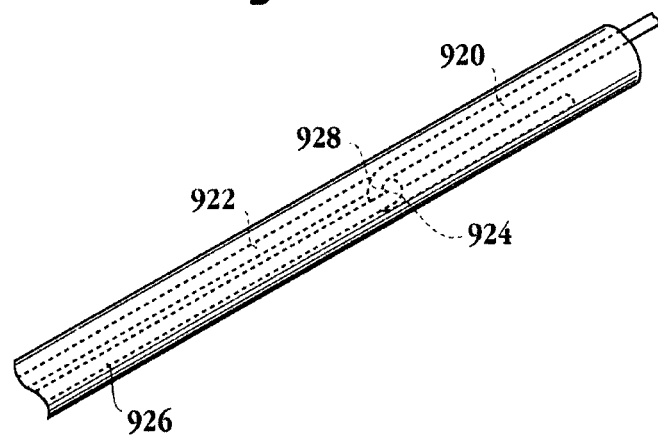
Figure 21C:
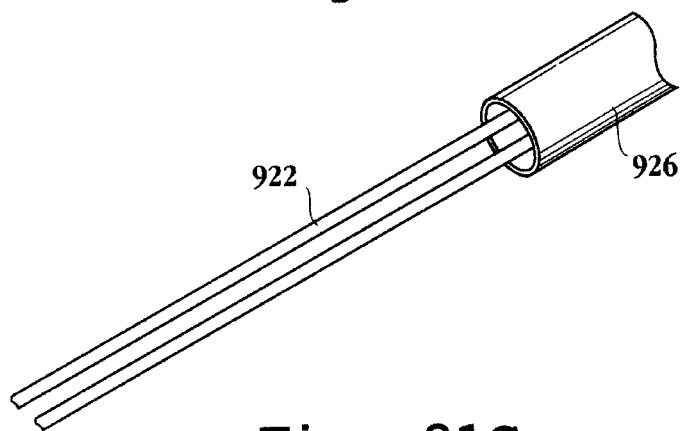

Yet another structure whereby a valve implantation device is attached to leg members of a clasper multiplex unit is illustrated in FIGS. 21-22. FIG. 21A-C shows how a flexible leg could be interlocked with a tension element. In this embodiment, the tension element may or may not be made of a flexible material. As shown in FIG. 21A, flexible leg 920, comprises an apex member 928 which interlocks with tension element 922 at tension element apex member 924. Flexible leg 920 and tension element 922 are reversibly connected via this interlock prior to delivery, when the valve prosthesis is packed into the implantation device. After interlocking the flexible leg and the tension element, a hollow track wire, e.g., track wire 926, is moved distally to cover the interlocked portion as well as the distal portion of the flexible leg as shown in FIG. 21B. The track wire prevents the flexible leg from radially expanding prior to and during delivery of the valve prosthesis. FIG. 21C presents a depiction of the proximal end of this attach-and-release embodiment. It is understood that tension element 922 and track wire 926 are attached at their proximal ends to a point near the proximal end of the valve implantation device or to the valve implantation device control unit is such a manner as to allow independent longitudinal movement of the tension element and the track wire.

Figure 22A:
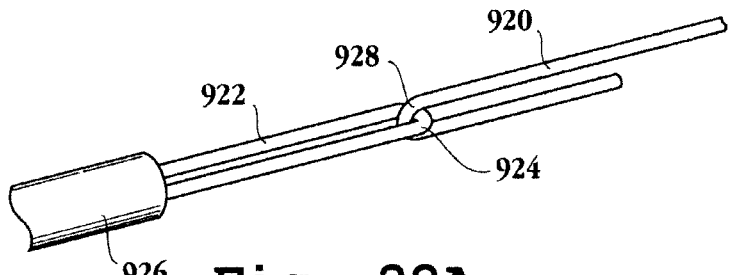
FIGS. 22A-22D illustrate an alternative embodiment for release of a valve delivery device from a leg member of a clasper multiplex unit.
Figure 22B:
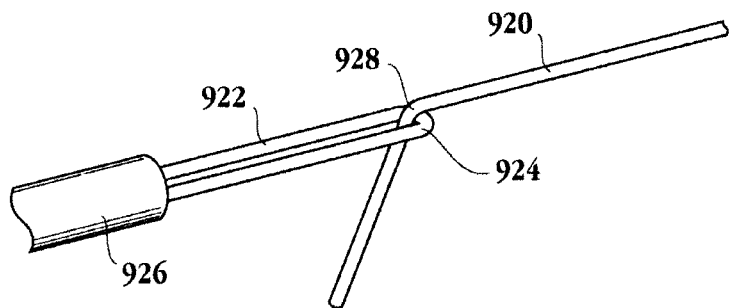
Figure 22C:
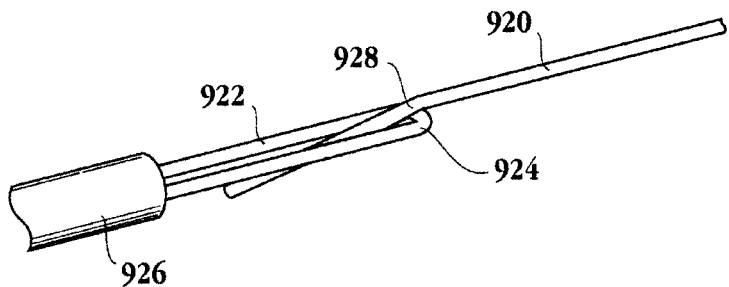
Figure 22D:
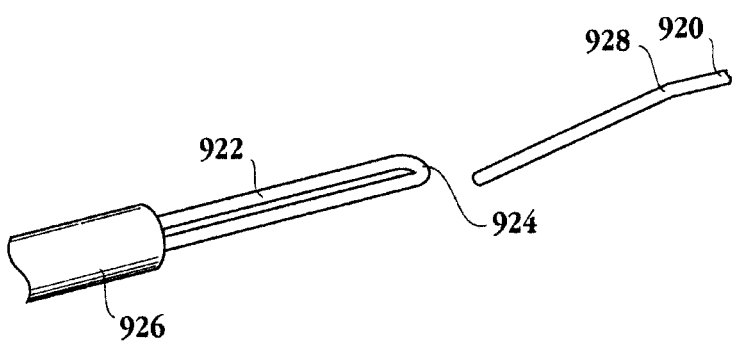

FIGS. 22A-C show how flexible leg 920 is released from tension element 922. First, the track wire may be pulled back in a proximal direction to uncover the proximal end of the flexible leg (see FIG. 22A). Due to the flexible nature of flexible leg 920, pulling tension element 922 in a proximal direction causes flexible leg 920 to straighten at its apex 928, as shown in FIGS. 22B-22C. The user may then pull track wire 926 and tension element 922 in a proximal direction to allow release of flexible leg 920.

The flexible tension element may be, for example, a monofilament, multifilament or braided multifilament structure. Examples may include wires, threads or monofilaments such as that used in surgical sutures. Monofilaments can be made from natural sources such as catgut, silk or linen, or they may be synthetic. Monofilament nonabsorbable sutures may be made from, for example, nylon or polypropylene. The flexible tension element can be comprised of a shape memory material. Persons of ordinary skill in the art will be able to choose appropriate materials for flexible tension elements based on characteristics such as tensile strength, knot strength, elasticity, memory or stiffness and tissue reactivity.

In one embodiment, the flexible leg as described above and shown in FIGS. 21-22, may function as the clasper leg, wherein, for example, flexible leg 920 would be attached to hole 875 of clasper multiplex unit 850 (see FIG. 17B). In another embodiment, the flexible leg may function to attach a clasper leg to the tension element of the valve implantation device. For example, flexible leg 920 in FIG. 21A, could be interlocked at its proximal end with tension element 922, and attached at its distal end to the proximal end of clasper leg 810 of clasper multiplex unit 800 (see FIG. 17A). In yet another embodiment, the flexible leg may be attached at its distal end directly to the valve support frame, for example, at a commissure post on the frame.

VIII. Method for Deploying an Aortic Valve Prosthesis

In a sixth aspect, a method for delivering the valve prosthesis described herein in a compressed form or compact condition to the heart using implantation device, such as implantation device 100, is provided.

Figure 23:
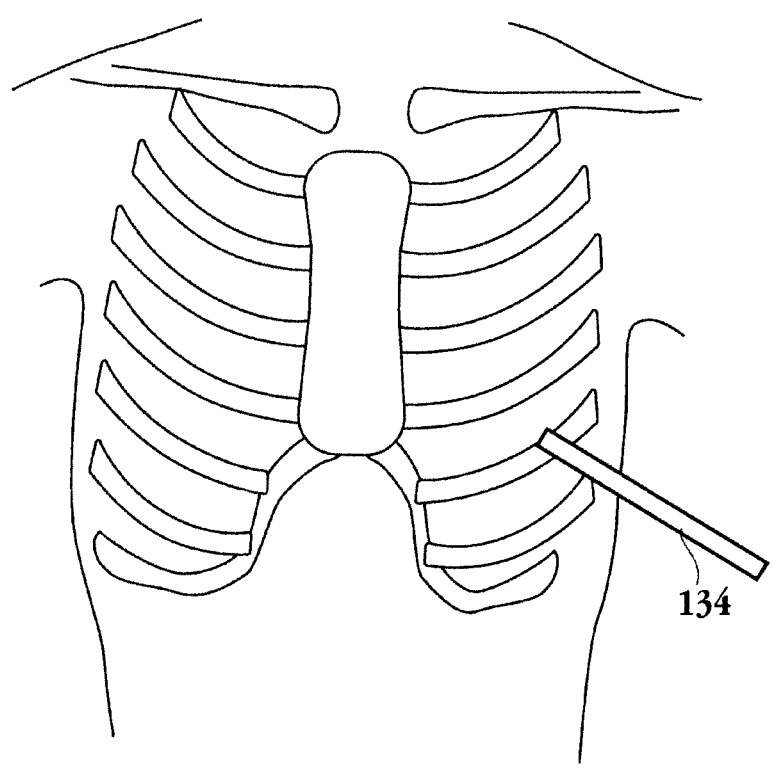
FIG. 23 illustrates an introducer inserted in the thoracoabdominal region.

FIGS. 24A-24H show one procedure for delivering a valve prosthesis to the aortic valve, positioning and deploying the valve prosthesis. One of skill in the art will readily understand the application of the delivery method and device manipulations as they apply to, for example, implantation device 100. FIGS. 24A-24H are cross-sectional views through the left side of a patient's heart showing the acts performed in delivering the support structure using a transapical approach. It should be noted that such figures as provided herein are schematic in nature and thus do not necessarily depict a precise representation of the delivery process. For example, the patient's ribcage is not shown for illustrative purposes and the size of the sheaths used with the delivery systems have been altered somewhat in order to better illustrate the procedure. One of ordinary skill in the art, however, will readily understand the range and types of sheaths and catheters that can be used to implement the depicted procedure. FIG. 23 shows insertion of an introducer 134 into the patient.

Figure 24A:
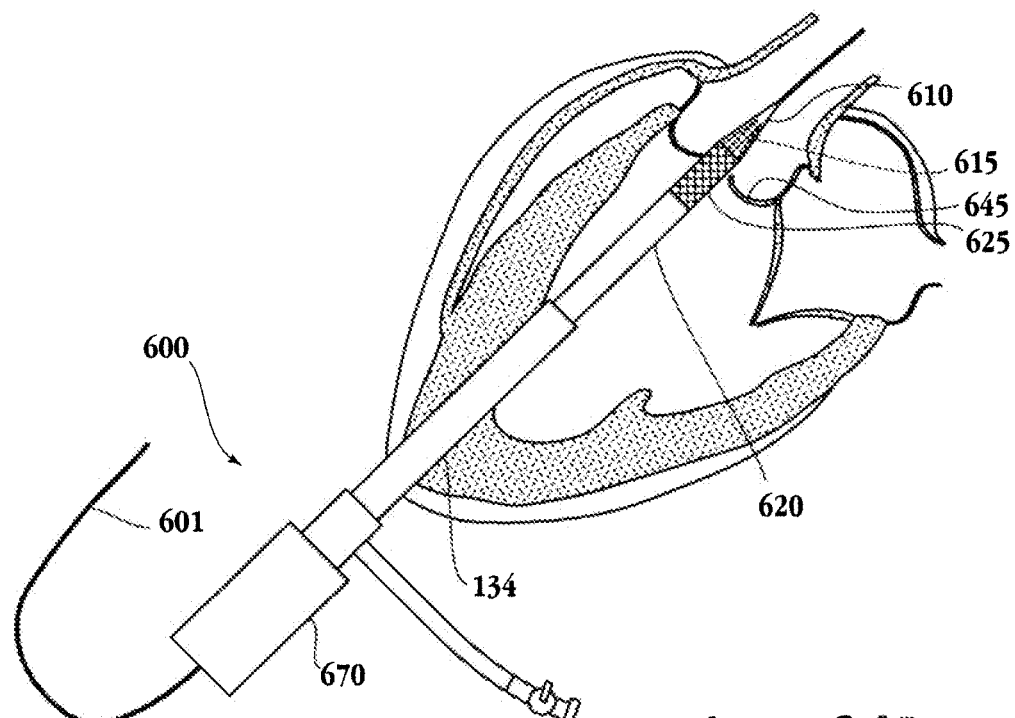
FIGS. 24A-24H are schematic illustrations of a transapical procedure for aortic valve replacement.
Figure 24B:
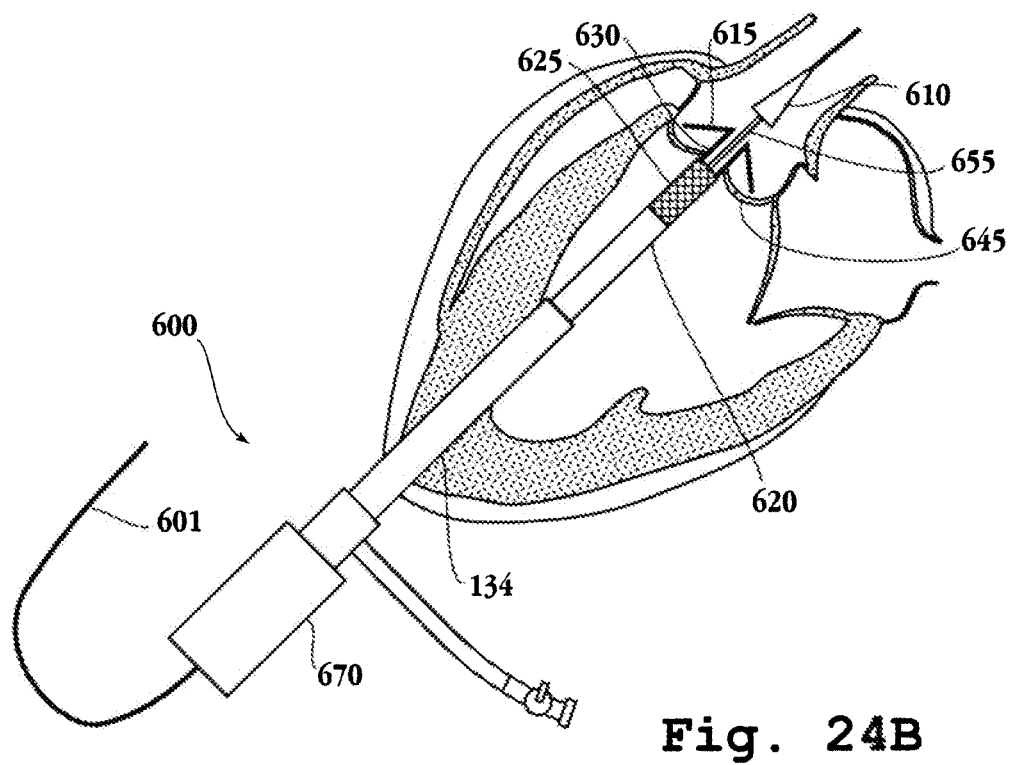

FIGS. 24A-24H illustrate transapical implantation of an aortic valve using an implantation device 600. Implantation device 600 shares many features with implantation device 100. Implantation device 600 is advanced along the guide-wire until second sheath (nose cone) 610 is position past (distal to) the native heart valve. A second sheath controller switch within a control unit 670 is used to move second sheath 610 (nose cone) distally, to allow u-shaped members 615 of the prosthetic valve claspers to extend radially, as shown in FIG. 24B. The method as described below and illustrated in FIGS. 24A-24H can be used with delivery device 100 and valve prosthesis 2 described above.

A first sheath controller switch in control box 670 is used to move first sheath 620 in a distal direction and partially through the native heart valve, as shown in FIG. 24A. First sheath 620 encases support frame 625 of the valve prosthesis in a compact condition. As first sheath 620 is moved distally toward the native heart valve, the valve claspers remain stationary. A native valve leaflet is shown by 645.

FIG. 24B shows that second sheath 610 is pushed in a distal direction to uncover valve claspers 615. Second sheath 610 can be moved in a distal direction by pushing distally a second sheath control cable 655 that is attached at its distal end to the second sheath and at its proximal end to the control unit. Once uncovered, the valve claspers extend radially above the native valve.

Figure 24C:
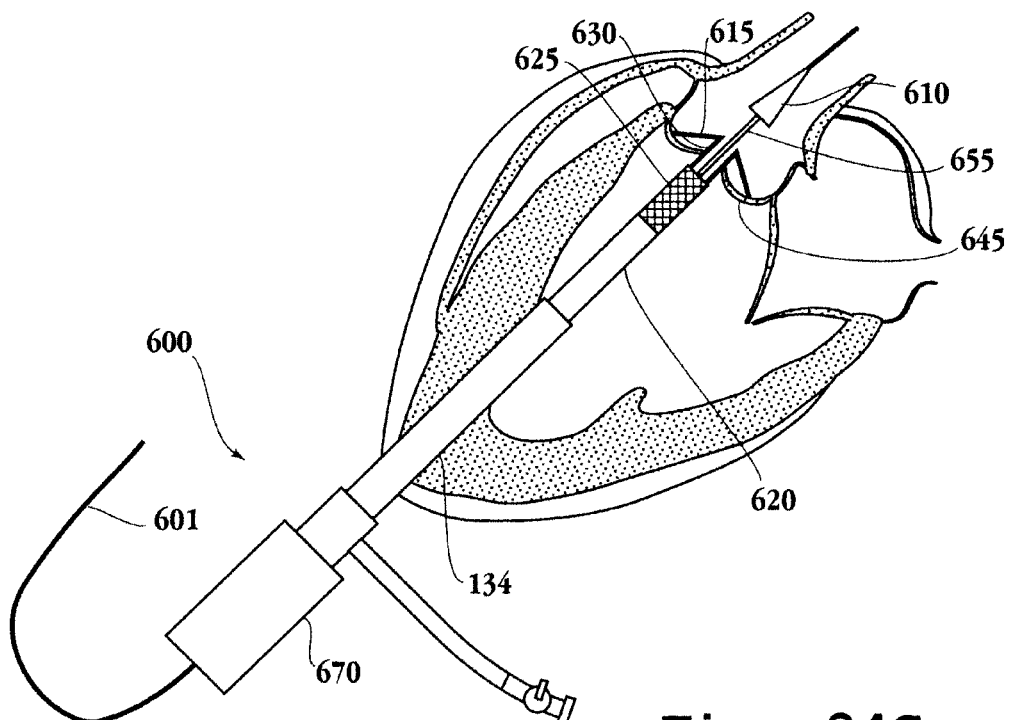

FIG. 24C shows that the control unit has been manipulated to pull the valve claspers in a proximal direction until the u-shaped members of valve claspers contact or otherwise engage the native valve, such as abutting the floor of the native valve sinus or the base of the native valve leaflets. The valve claspers are moved proximally by pulling the track wires in a proximal direction as described above.

Figure 24D:
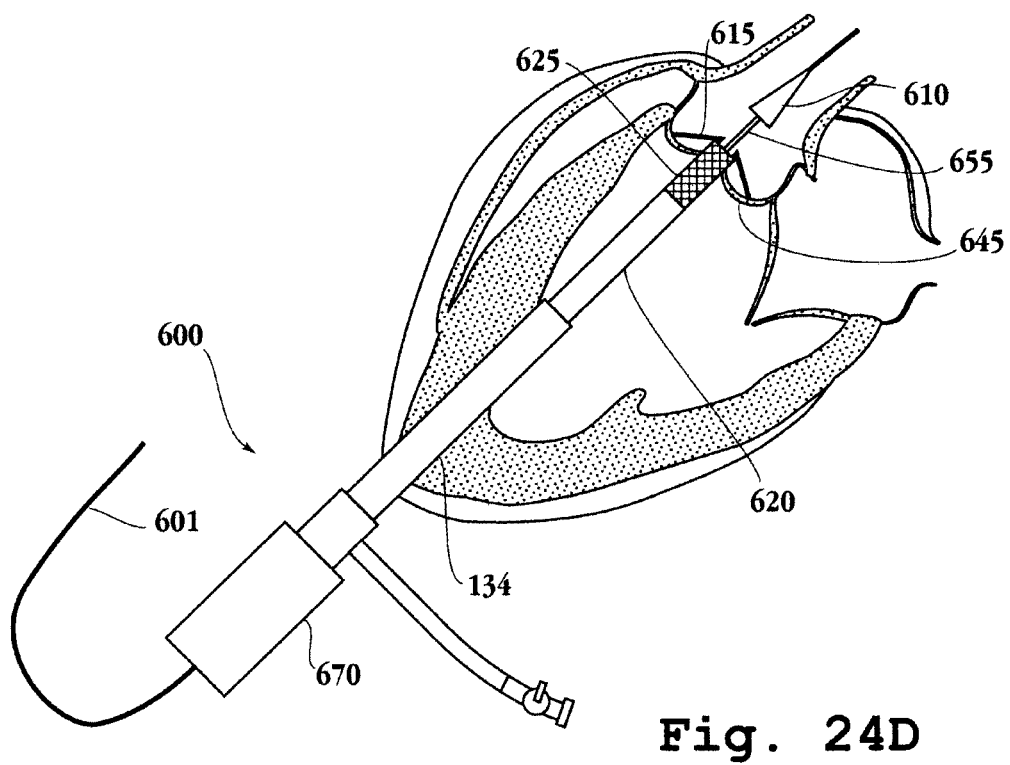

FIG. 24D shows that first sheath 620 has been advanced until the distal edge of the first sheath, and therefore the distal edge of support frame 625 abuts the apex of the valve claspers. Accordingly, the support frame is now in the proper position within the native valve for expansion of the support frame and implantation of the valve prosthesis. It is understood that prior to expansion of the support frame, the implantation device can still be manipulated to make minor adjustments of the valve prosthesis in terms of distal, proximal and rotational positioning.

Figure 24E:
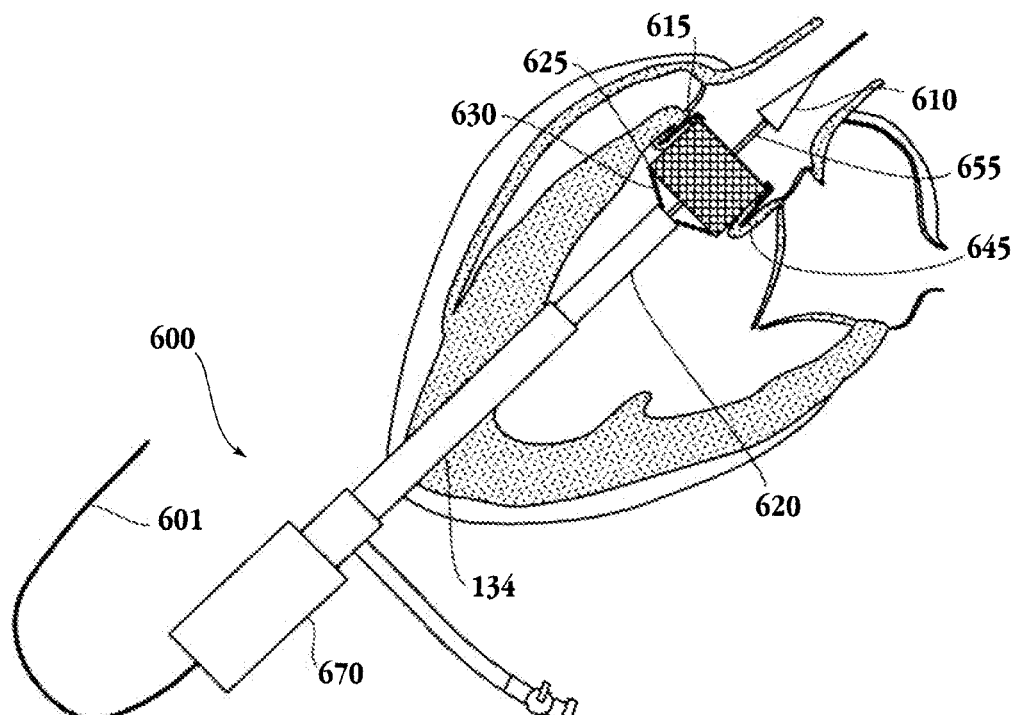

FIG. 24E shows that first sheath 620 has been pulled back in a proximal direction while holding the support frame stationary in order to uncover support frame 625 allowing support frame 625 to expand radially along the track wires which extend from leg members of the valve claspers and allow the valve claspers to clasp onto leaflets, such as leaflet 645, of the native valve, as shown in FIG. 24E. As can be seen, native valve leaflets, e.g. 645, are sandwiched between valve clasper 615 and support frame 625. Track wires, e.g., track wire 630, are still in contact with the valve claspers. Track wires help to guide the correct radial position (commissure to commissure) of the valve prosthesis when it expands or deploys.

Figure 24F:
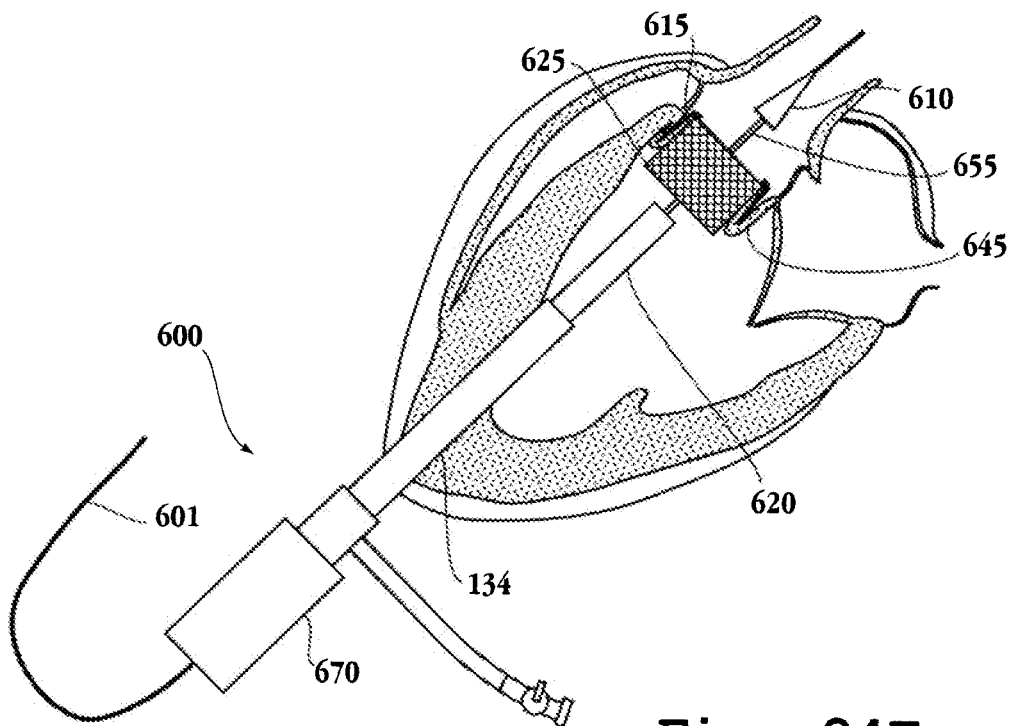

FIG. 24F shows that the track wires have been pulled back in a proximal direction to release the valve claspers after ensuring that the valve prosthesis is properly placed. The track wires may be detached from the leg members of the valve claspers by pushing or pulling back on release switches.

Figure 24G:
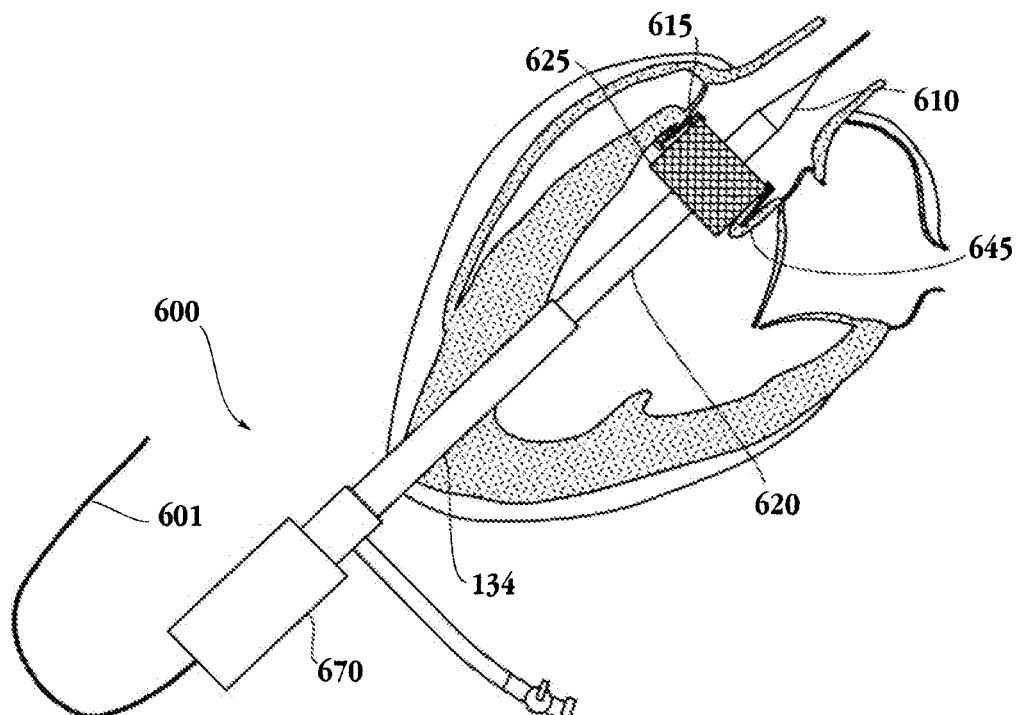

FIG. 24G shows that first sheath 620 has been pushed in a distal direction to abut the proximal edge of second sheath 610. This step is option and functions to protect surrounding tissue from possible damage by the proximal edge of the second sheath as the delivery device is removed from the patient. The implantation device is pulled in a proximal direction along the guidewire to remove the device from the patient, leaving the deployed valve prosthesis in place.

Figure 24H:
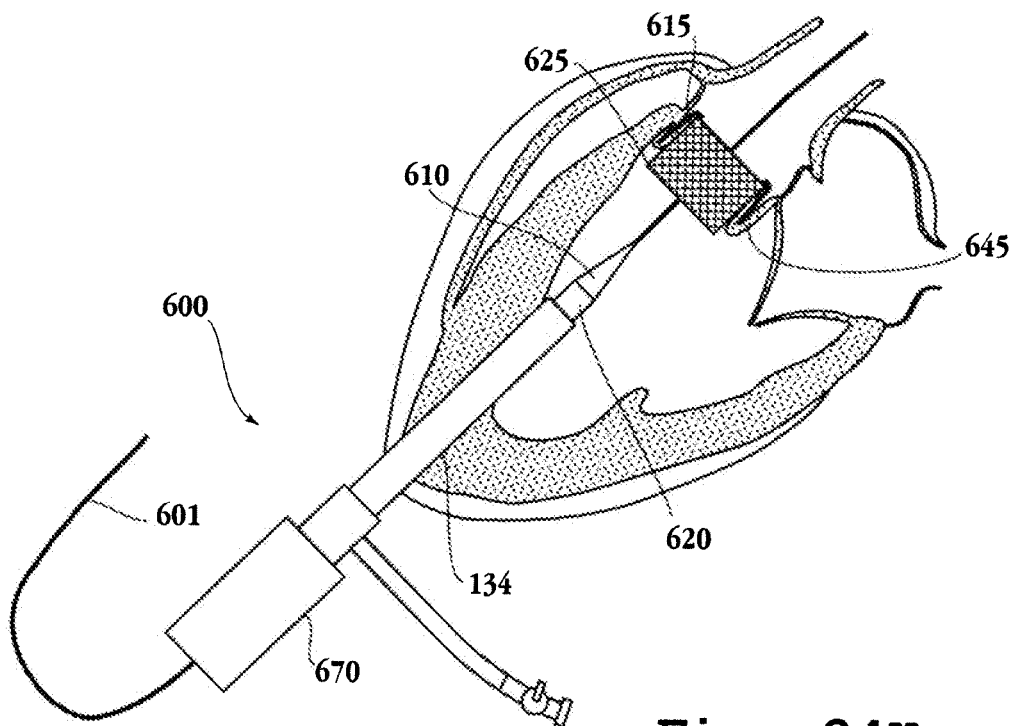

FIG. 24H shows removal of the implantation device from the heart while leaving the prosthetic valve in place.

In an alternative embodiment, first sheath 620 is moved in a proximal direction to expose only a portion of the valve prosthesis support frame. A valve support frame as depicted in FIGS. 1C-1D could be implemented for this procedure and encased in first sheath 620.

When the valve prosthesis is fully deployed in the annulus of the native heart valve, the native valve leaflets become sandwiched in between the u-shaped members and the leg members of each of valve clasper 615. This provides additional anchoring of the valve prosthesis within the heart.

IX. Method for Deploying a Mitral Valve Prosthesis Via Inferior Vena Cava Delivery In a seventh aspect, a method for delivering a valve prosthesis in a compressed form or compact condition to the heart using an implantation device 100 via delivery through the inferior vena cava is provided. In one embodiment, the valve prosthesis is a mitral valve prosthesis.

The method of delivering a mitral valve via the inferior vena cava using implantation device 100 is illustrated in FIGS. 25A-25L. The implantation device can be inserted into the femoral vein of the patient then advanced to the inferior vena cava as shown in FIG. 26. Prior to inserting the implantation device into the patient, a guidewire 110 can be introduced into the femoral vein and then advanced using imaging through the inferior vena cava, then advanced through the intra-atrial septum with a needle according to methods known to a skilled artisan, into the left atrium and distal through the mitral valve into the right ventricle. Implantation device 100 is then advanced along guidewire 110 through the intra-atrial septum and through the mitral valve into the left ventricle.

Figure 25A:
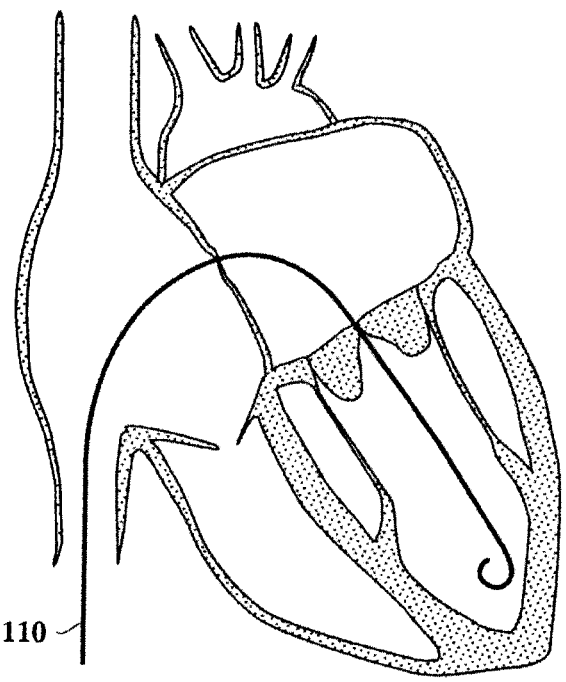
FIGS. 25A-25L are schematic illustrations of an alternative embodiment for an implantation device and a method for implanting a mitral valve prosthesis in a native mitral valve of a heart.
Figure 25B:
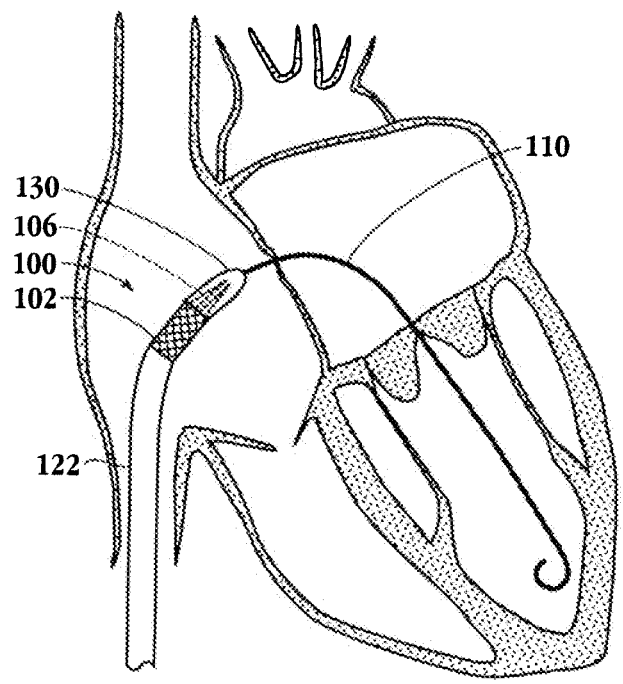
Figure 26:
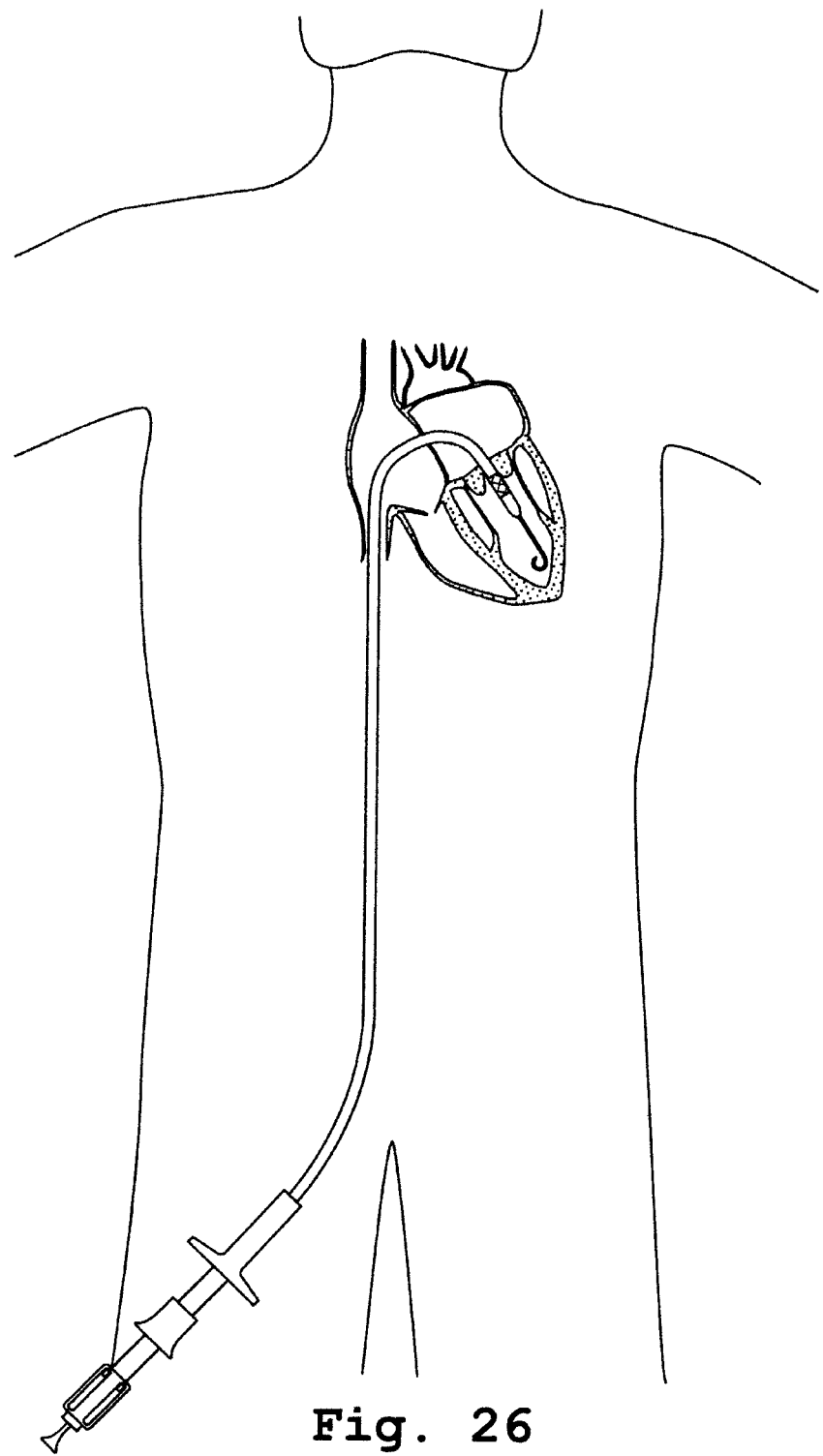
FIG. 26 illustrates a path for delivery of a prosthetic heart valve which includes advancing an implantation device through the inferior vena cava.

FIG. 25B shows the implantation device prior to be advanced along guidewire 110 through the transeptal wall into the left atrium.

Figure 25C:
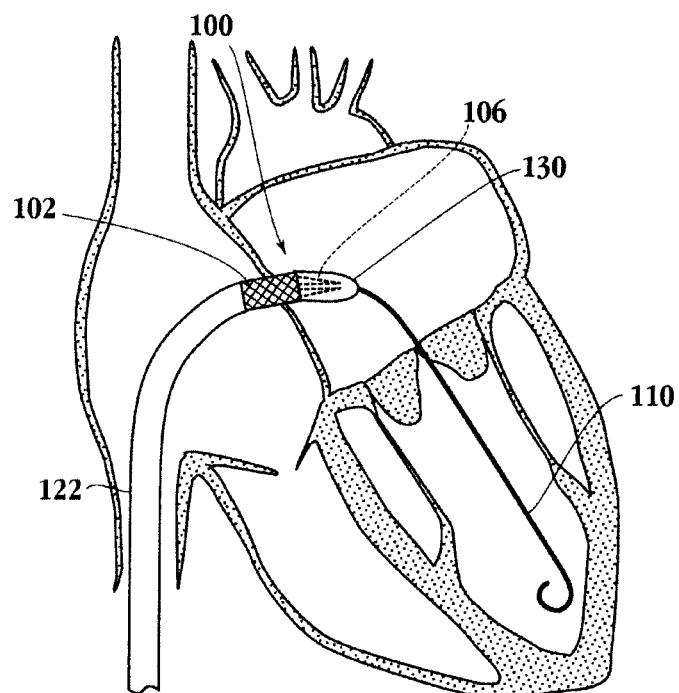

FIG. 25C shows advancement of the implantation through the transeptal wall into the left atrium. An embodiment of the first sheath, shown in FIGS. 25A-25K as 122, illustrates that the first sheath can be very long and flexible to allow delivery from an insertion point distant from the heart as is understood by the skilled artisan.

Figure 25D:
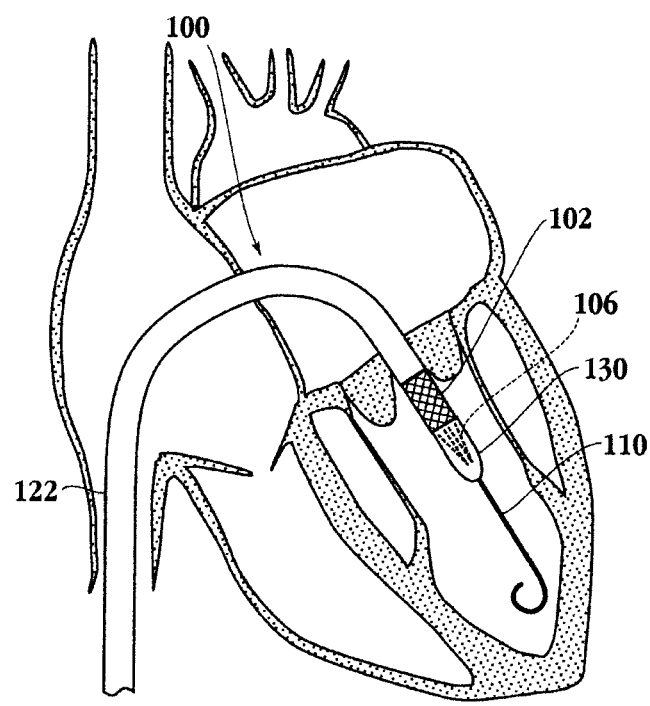

FIG. 25D shows that the distal end of the implantation device has been advanced through the mitral valve such that at least a portion of the first sheath which encases the valve prosthesis support frame is located within the left ventricle. In an alternative embodiment, the implantation device may be advanced distally until the valve prosthesis within the first sheath is positioned within the native valve.

Figure 25E:
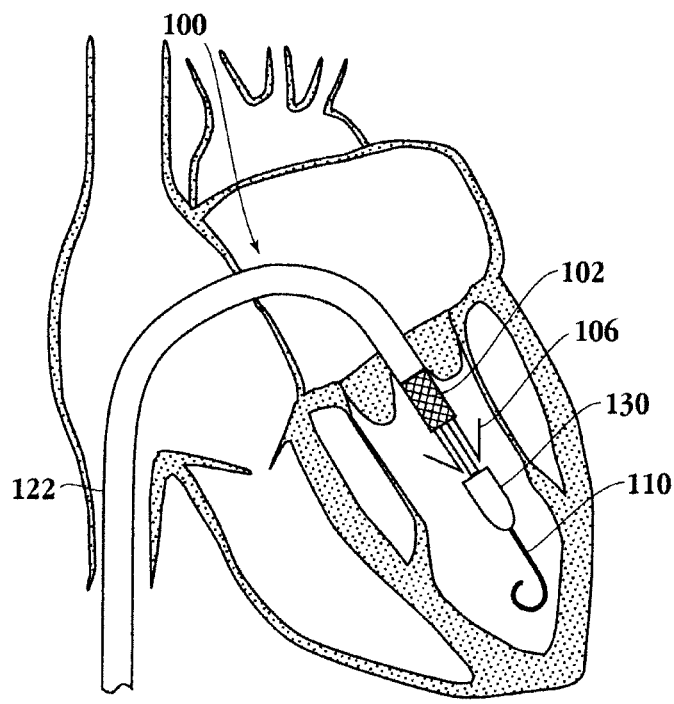

FIG. 25E shows that second sheath 130 has been pushed distally while valve claspers, e.g., valve clasper 106, is held stationary, to uncover the valve claspers, allowing the u-shaped members of the valve claspers to expand radially from the central axis of the delivery device.

Figure 25F:
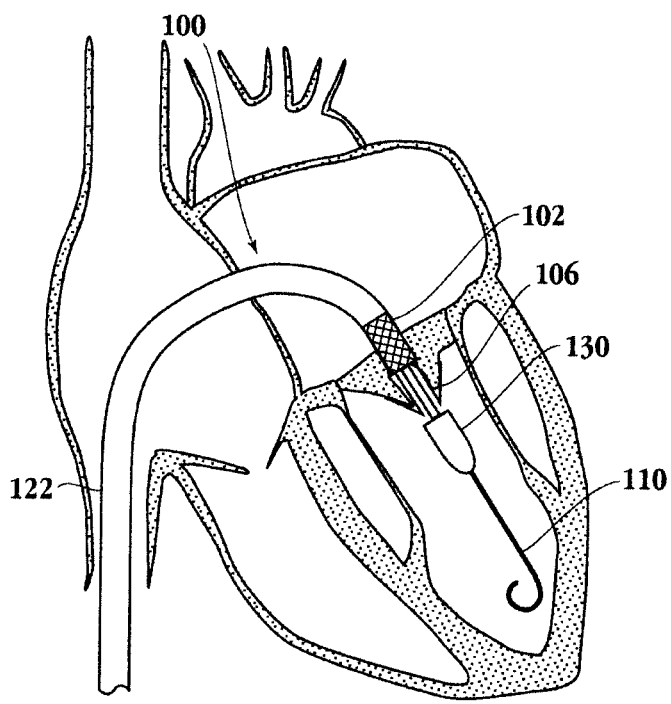

FIG. 25F shows that the first sheath with encased valve prosthesis support frame 102 in its compact condition is pulled proximally with valve claspers, e.g., valve clasper 106, until the u-shaped members of the valve claspers contact or otherwise engage the native valve. The user does not need to rely on imaging for this manipulation as the user is able to feel resistance when the u-shaped members of the valve claspers contact the native valve.

Figure 25G:
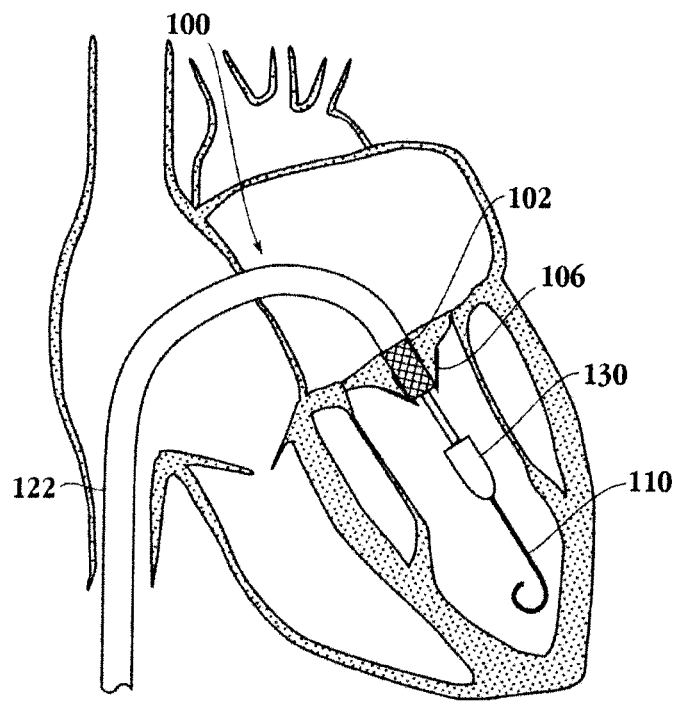

FIG. 25G shows that first sheath 122 has been advanced in a distal direction until the distal edge of first sheath 122 abuts or contact the apex of the valve claspers.

Figure 25H:
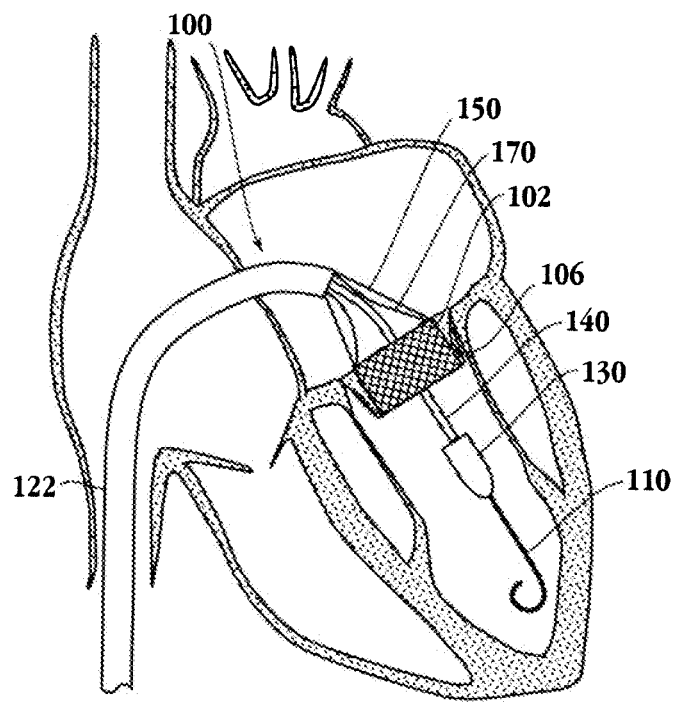

FIG. 25H shows the implantation device after first sheath 122 has been pulled in a proximal direction to uncover valve prosthesis support frame 102 allowing the support frame to expand or deploy to its expanded condition. At this time, the native valve leaflets are positioned between the valve claspers and the support frame. More specifically, the valve leg member of the valve clasper is positioned between the native valve leaflet and the support frame, and the native valve leaflet is positioned between the valve clasper leg member and the valve clasper u-shaped member. FIG. 25H also shows track wire 150 still reversibly attached to valve clasper 106 and pusher wire 170 still engaged with support frame 102.

Figure 25I:
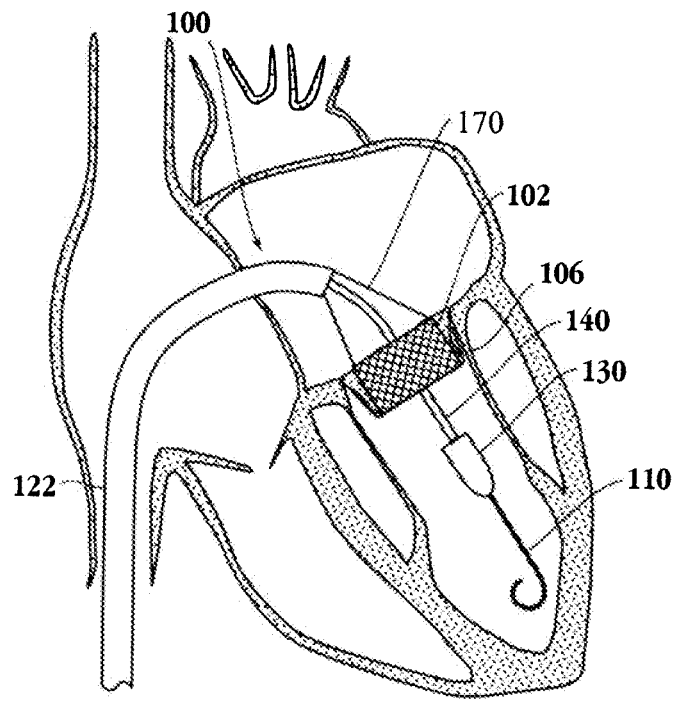

FIG. 25I shows that the track wires have been pulled in a proximal direction to unattach them from the valve claspers. Pusher wires 170 are still engaged with the valve prosthesis support frame, helped to maintain the valve prosthesis in its desired position as the track wires are unattached.

Figure 25J:
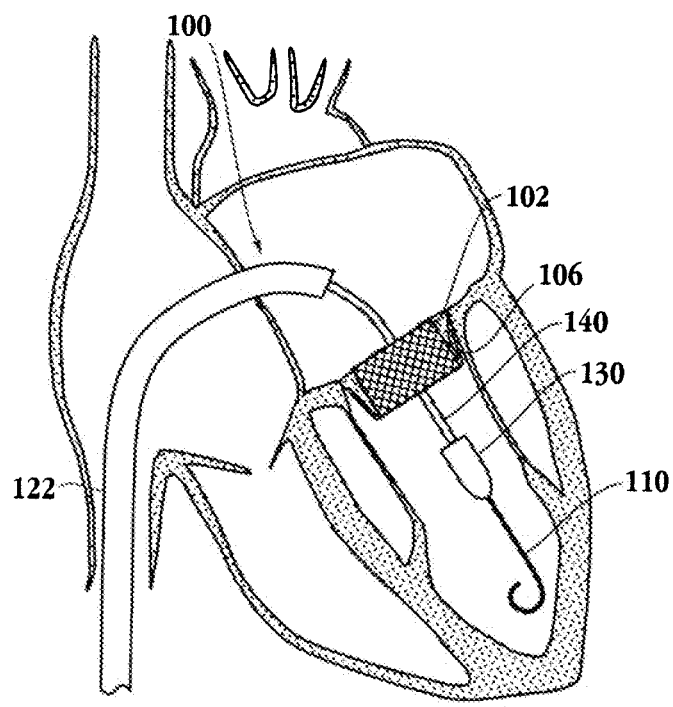

FIG. 25J shows that the pusher wires have been pulled in a proximal direction to disengage each pusher wire from the valve prosthesis support frame.

Figure 25K:
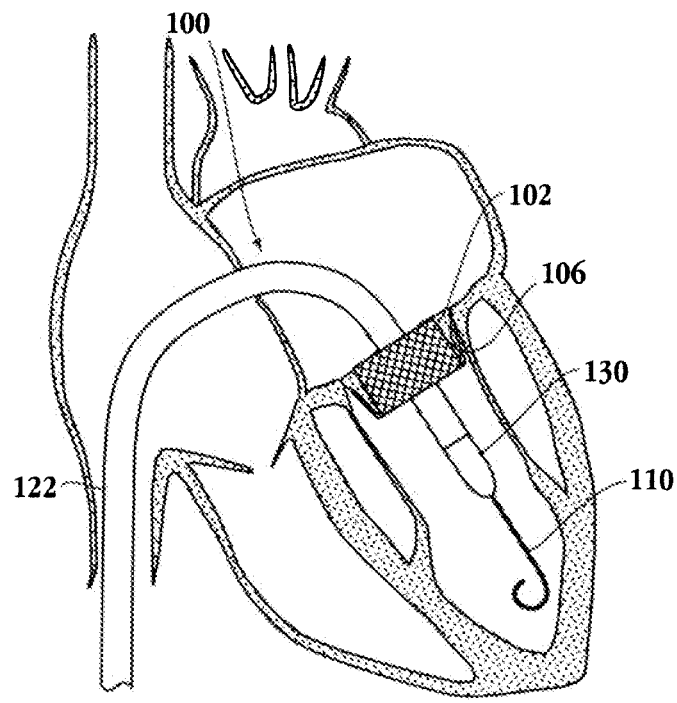

FIG. 25K shows that first sheath 122 has been pushed in a distal direction until it abuts the proximal edge of second sheath 130.

Figure 25L:
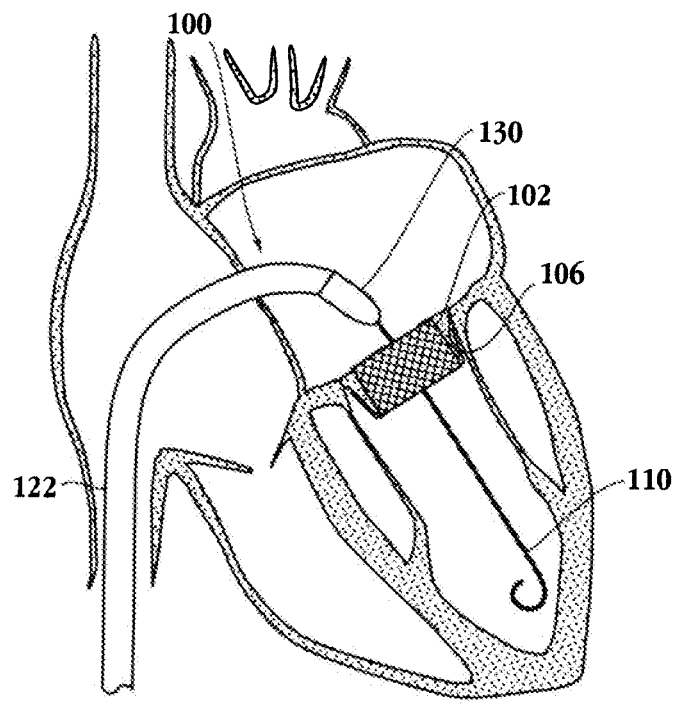

FIG. 25L shows proximal movement of the implantation device to remove the device from the patient while leaving the valve prosthesis in the native heart valve.

X. Method for Deploying a Valve Prosthesis Via Superior Vena Cava Delivery

Figure 27:
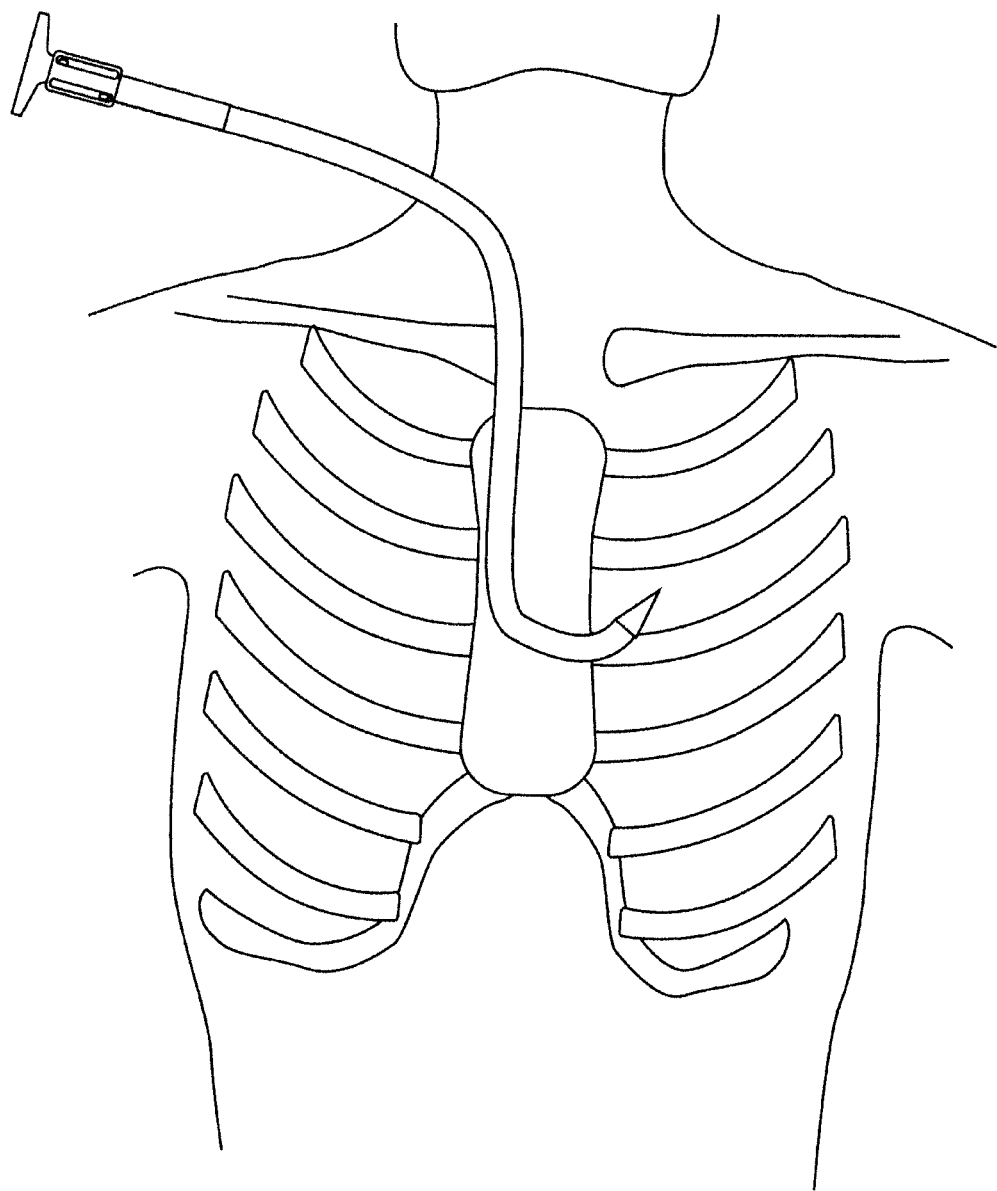
FIG. 27 illustrates a path for delivery of a prosthetic heart valve which includes introducing an implantation device into the jugular vein and advancing the device through the superior vena cava.

In an eighth aspect, a method for delivering the valve prosthesis described herein in a compressed form or compact condition to the heart using an implantation device 100 via percutaneous delivery through the superior vena cava is provided and is shown in FIG. 27. In this aspect, the valve prosthesis is a pulmonary valve prosthesis.

Implantation device 100 for delivery of a pulmonary valve prosthesis through the superior vena cava is inserted into the superior vena cava of the patient. Prior to inserting the implantation device into the heart, a guidewire 110 is introduced into the jugular vein and then advanced using an imaging through the superior vena cava into the right atrium, then through the tricuspid valve into the right ventricle and through the native pulmonary valve annulus into the pulmonary artery.

Figure 28:
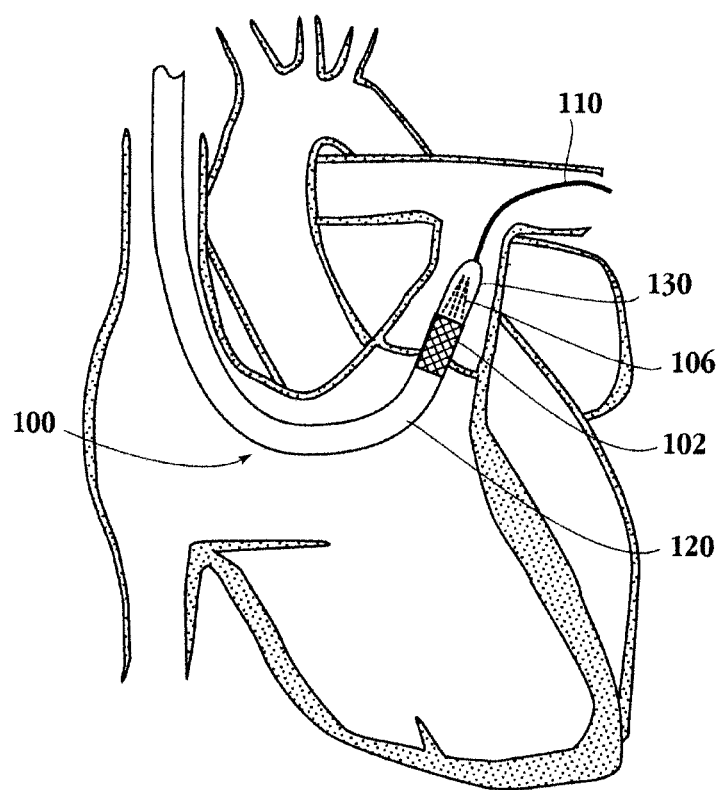
FIG. 28 illustrates a path for delivery of a prosthetic pulmonary valve which includes an implantation device into the jugular vein and advancing the device through the superior vena cava.

In one embodiment, an introducer is first inserted into the jugular vein along guidewire 110 and implantation device 100 is inserted through the introducer. In one embodiment, implantation device 100 as described above may be inserted into the jugular vein and advanced through the superior vena cava into the right atrium. The distal end of the implantation device is then advanced through the tricuspid valve into the right ventricle, then through the native pulmonary valve and into the pulmonary artery as shown in FIG. 28.

After introduction of the implantation device into the right ventricle, the device is advanced along the guidewire until the valve claspers are located past the native pulmonary valve. First sheath 120 encasing prosthetic valve support frame 102 in a compact condition is also advanced to a position approximately adjacent and proximal to (below) the native pulmonary valve. It can be appreciated that the once second sheath 130 encasing the valve claspers is located past the native pulmonary valve and in the pulmonary artery, methods for positioning and deploying the prosthetic pulmonary valve are the same or very similar to those described above for implanting a mitral prosthetic valve using implantation device 100.

XI. Method for Deploying a Valve Prosthesis Via Femoral Artery Delivery

In a ninth aspect, a method for delivering the valve prosthesis described herein in a compressed form or compact condition to the heart using implantation device 300 is provided. In one embodiment, the valve prosthesis is an aortic valve prosthesis delivered via the femoral artery.

Figure 29A:
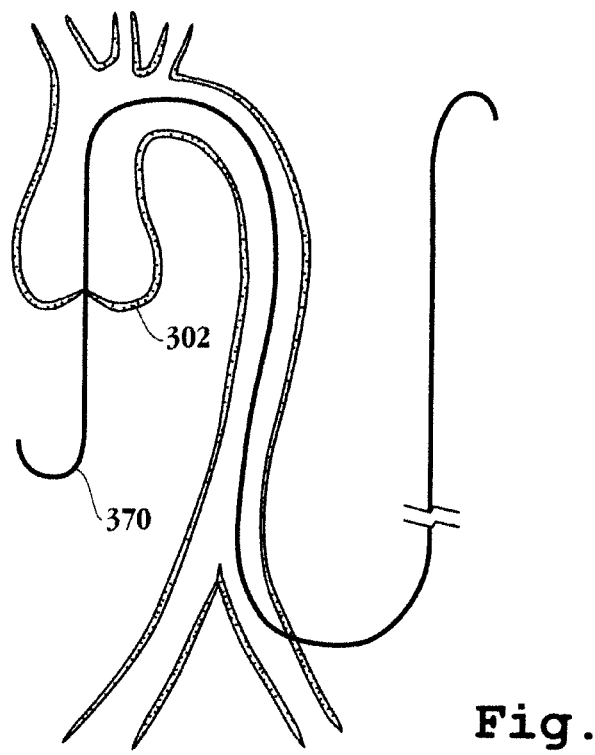
FIGS. 29A-29H illustrates a method of using one embodiment of an implantation device for implanting a prosthetic aortic valve which includes advancing the implantation device through the femoral artery and aortic arch.

A guidewire is inserted into the femoral artery according to methods known in the art and advanced through the femoral artery, the aortic arch, and the aortic valve as shown in FIG. 29A.

Figure 29B:
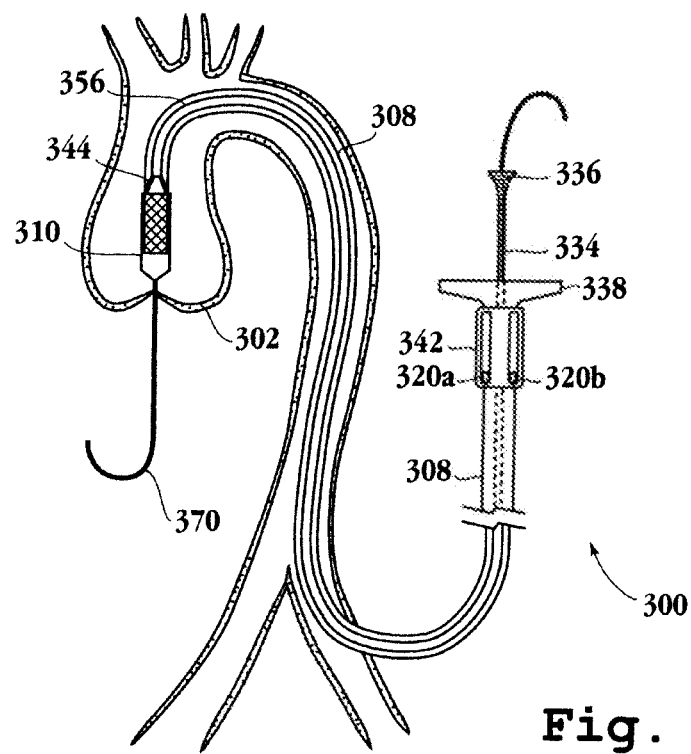

FIG. 29B shows implantation device 300 after it has been inserted into the femoral artery and guided through the aortic arch, then advanced along the guidewire until the distal end of the second sheath positioned above the native aortic valve 302. One would readily understand that in this embodiment, the first sheath has a length sufficient to extend from the location at which the implantation device enters the patient past the aortic valve. The first sheath is also made of a material flexible enough and with a diameter small enough to be advanced safely through the femoral artery.

Figure 29C:
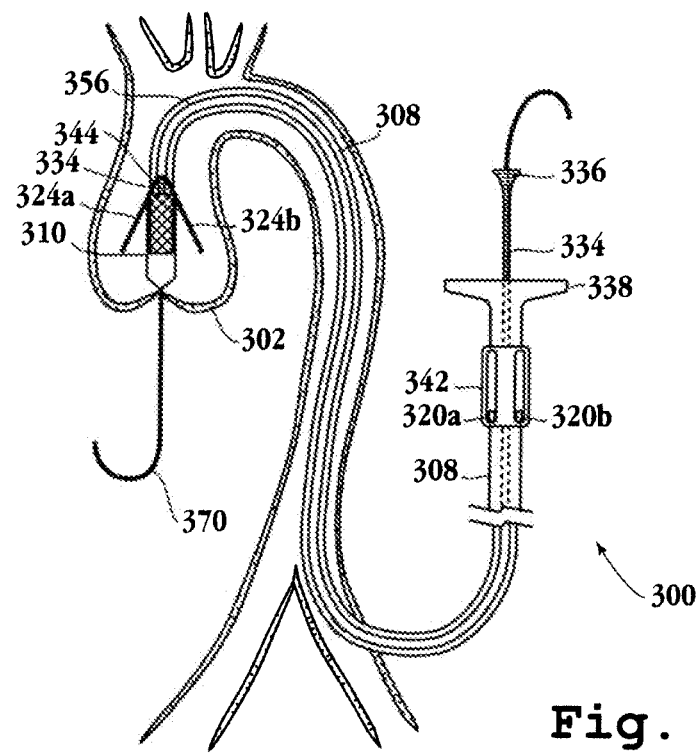

FIG. 29C shows implantation device 300 after the valve claspers, such as valve claspers 324a, 324b, have expanded radially from the central axis of the implantation device. In this embodiment, the implantation device comprises three valve claspers, each with a u-shaped member having a curved portion and a straight portion as described above. The curved portion of each valve clasper 324 may be uncovered by moving second sheath 310 distal while holding the valve claspers stationary, or moving track wires 344 in a proximal direction. Prior to insertion of the implantation device into the patient, the curved portion of the valve claspers are only slightly covered by the proximal end of the second sheath. After the curved portion of valve clasper 324 is uncovered, track wires 344 are moved in a proximal direction to uncover the entirety of each of the valve claspers. At this time, shown in FIG. 29C, the straight portions of each valve clasper are encased at least partially in the track wires such that each track wire encases one straight portion of two separate valve claspers. In this embodiment, the implantation device comprises three track wires. Additionally, as shown in FIG. 13B, each track wire can encase a locking wire. As shown in FIGS. 14A-14D, the delivery device in one embodiment may comprise a track wire support 356 which may encase the plurality of track wires. FIG. 29C shows the valve claspers in an engagement position.

Figure 29D:
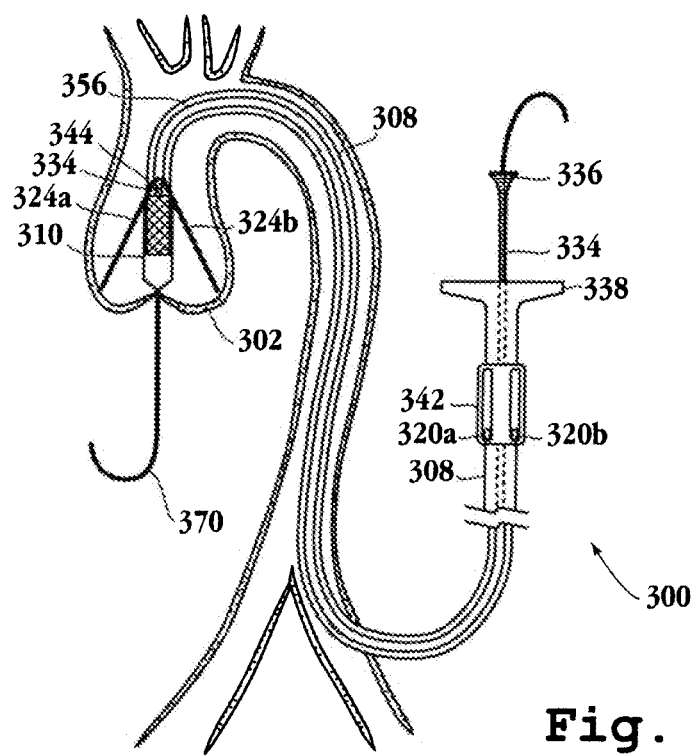

FIG. 29D shows that the track wires are advanced distally until the curved portion of each valve clasper engages the floor of the aortic sinus. Here, the valve claspers are in the nested position. This movement may be accomplished by pushing track wire controller 342 in a distal direction.

Figure 29E:
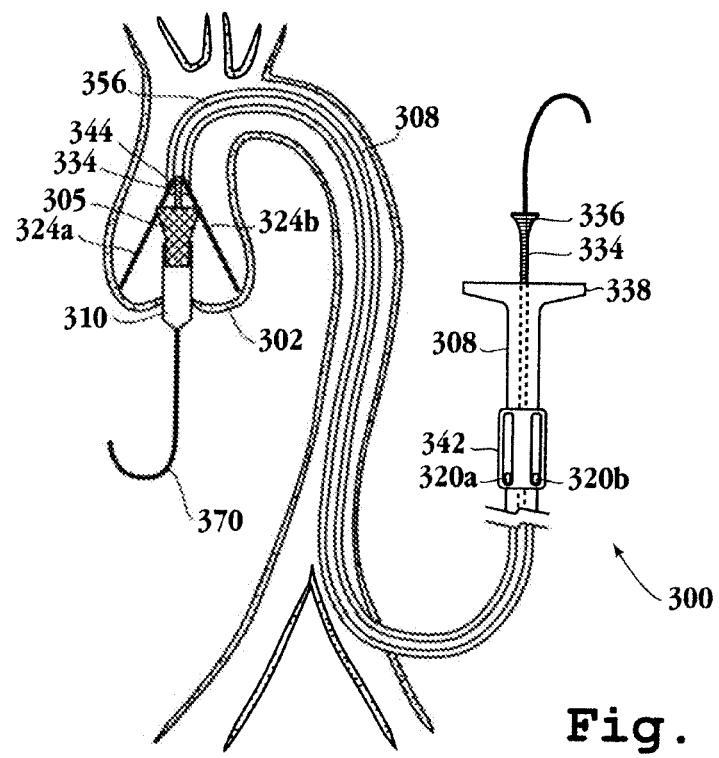

FIG. 29E shows that second sheath 310 is pushed in a distal direction to move second sheath 310 in a distal direction to at least partially uncover prosthetic valve 305. This movement may be accomplished by second sheath controller 338 in a distal direction. At this time, prosthetic valve support frame 305 partially expands or deploys. As prosthetic valve support frame 305 partially deploys, the straight portions of the valve claspers are still encased by a track wire. Expanding only a portion of the support frame (as indicated in FIGS. 1C-1D) may help to prevent the support frame from "jumping" out of position upon partial or full deployment of the support frame. Alternatively, the entire support frame may be uncovered and expanded in a single step. In some embodiments, the straight portions of the valve claspers have been threaded through a covering on the external face of the valve prosthesis support frame such that a minimal portion of the valve clasper is positioned between the covering and the valve support frame.

Figure 29F:
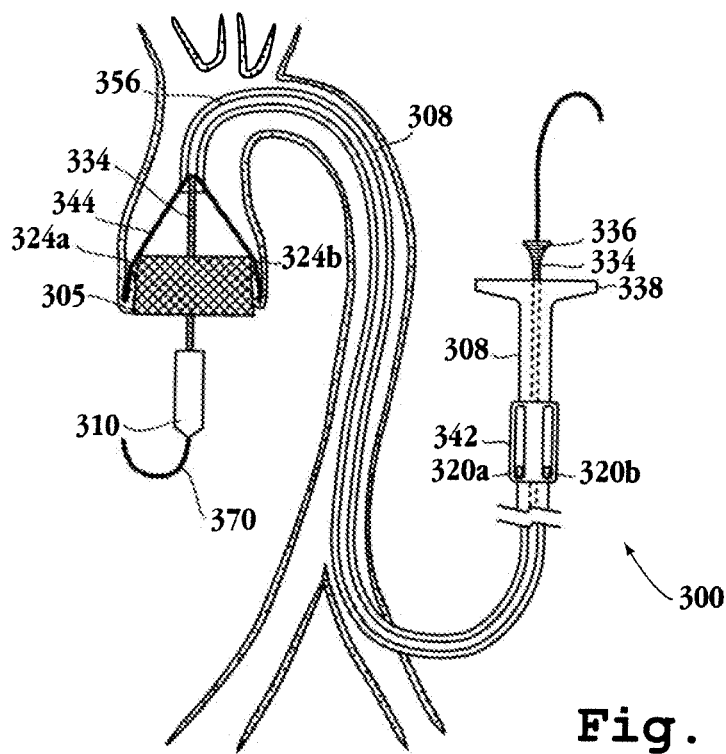

FIG. 29F shows that second sheath 310 has been moved in a distal direction to advance second sheath 310 in a distal direction to fully uncover and deploy valve prosthesis support frame 305. This movement of the second sheath may be achieved by distally moving second sheath controller 336. Upon full deployment of valve prosthesis support frame 305, straight portions of valve claspers 324 are still encased by track wires 344.

Figure 29G:
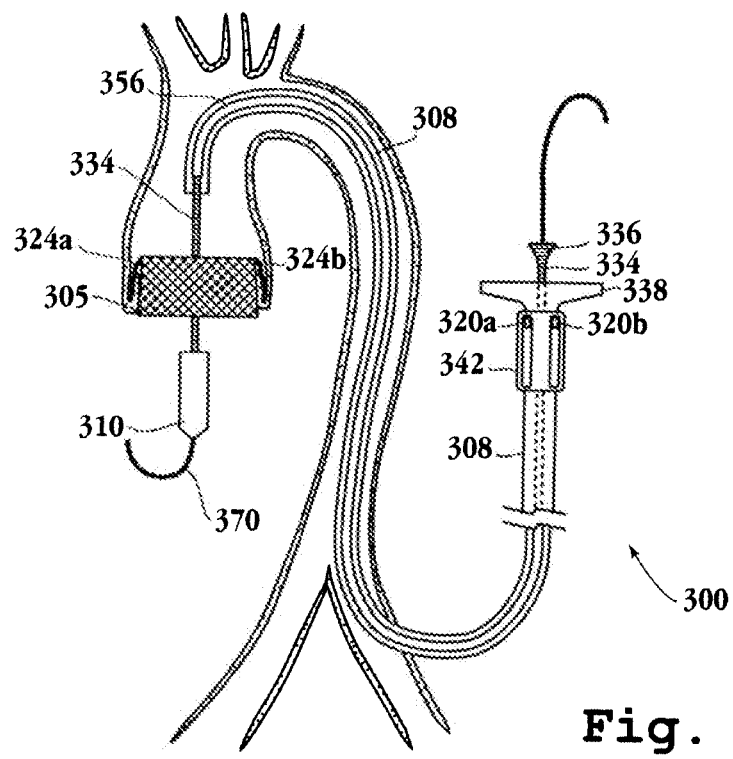

Track wires can be detached from the valve claspers by moving at least one release switch, such as release switch 320a or 320b in a proximal direction while holding the delivery device stationary so that at least one locking wire 328 is held stationary. In doing so, friction between locking member 329, the straight portions of two valve claspers 324, and track wire 344 is removed and at least one track wire and a locking wire may be moved in a proximal direction without applying any pulling force on valve clasper 324 such that the valve claspers 324 are released from the track wires. The delivery device after release of the valve claspers from the track wires is shown in FIG. 29G. In one embodiment, illustrated in FIG. 29G, the track wires are moved in a proximal direction by pulling track wire controller 342 in a proximal direction.

Figure 29H:
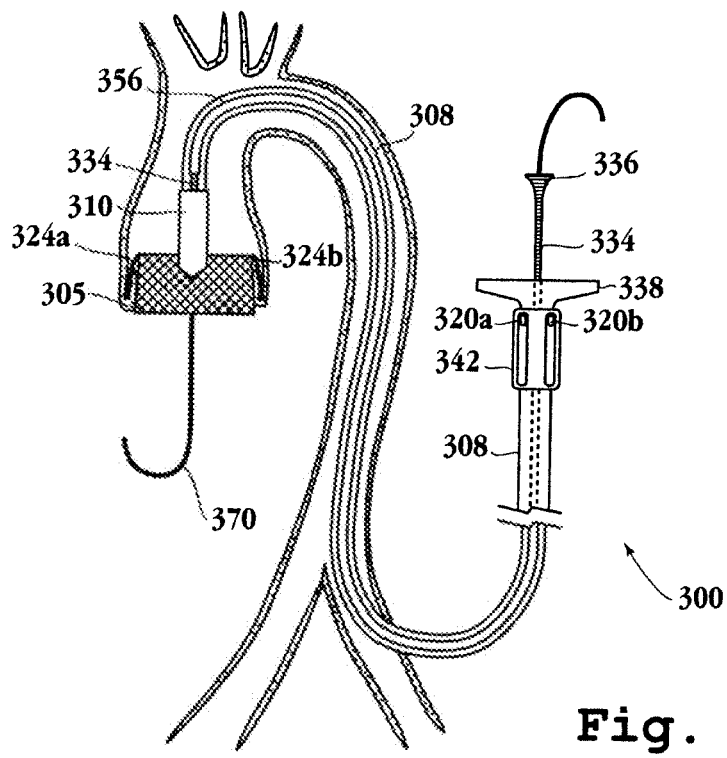

FIG. 29H shows that second sheath controller 336 can be pulled in a proximal direction to position second sheath 310 adjacent to first sheath 308. Delivery device 300 is then removed from the patient while leaving the valve prosthesis deployed within the native aortic valve.

XII. An Alternative Method for Deploying a Valve Prosthesis Via Femoral Artery Delivery In a tenth aspect, a method for delivering the valve prosthesis described herein to the aortic valve using implantation device 400 via the femoral artery is provided. Implantation device 400 can be used to deliver a variety of valve prostheses included those described herein with valve claspers 425 in which the valve claspers are movable along the longitudinal axis of the valve prosthesis or in which the valve claspers are fixed on support frame 470 of the valve prosthesis.

An embodiment of a method for deploying implantation device 400 by way of the femoral artery is illustrated in FIGS. 15A-15C. In this embodiment, a guidewire 110 is inserted into a femoral artery of a subject and advanced along the guidewire past the malfunctioned aortic heart valve into the left ventricle of the heart under the guidance of an imaging system using methods known to those having ordinary skill in the art. Implantation device 400 is then inserted into the femoral artery along the guidewire such that first sheath 420 which encases support frame 440 of a valve prosthesis is pushed into the target site in the vicinity of the malfunctioned native heart valve by following the path of the guidewire such that second sheath 430 which encases valve claspers 425 is above the native heart valve. This placement of the implantation device is guided by an imaging system and by moving the implantation device along the guidewire. It will be appreciated by a person having ordinary skill in the art that the implantation device is in the vicinity of the malfunctioned native heart valve when the position of the implantation device is such that upon removal of the first sheath, the valve prosthesis will deploy in a position that will allow the valve prosthesis to perform its intended function.

In one embodiment, implantation device 400 further comprises a control unit 410. The control unit comprises a first sheath switch 445 and a second sheath switch 435. The first sheath switch is attached by a wire or comparable member to the first sheath. The second sheath switch is attached by a wire or comparable member to the second sheath. Once implantation device 400 is in the vicinity of the target site, the second sheath switch is moved or adjusted such that the second sheath is moved in a proximal direction (toward the control unit) to uncover the valve claspers, as illustrated in FIGS. 15A-15B. This action allows the valve claspers to extend radially from the leg members.

In one embodiment, the implantation device further comprises a clasper pusher 460 located within and/or movably attached to the second sheath. When the second sheath switch is, for example, moved from the initial position distal position to a proximal position, this action moves the clasper pusher to the distal end of the second sheath. The clasper pusher engages the proximal end of the valve claspers such that when the second sheath switch is moved from the proximal position to the distal position (see FIGS. 15B-15C), the clasper pusher engages the proximal end of the valve claspers to push the valve claspers in a distal direction. In one embodiment, the valve claspers are pushed down (distal) by the clasper pusher to a position approximately adjacent to the native heart valve sinus. In one embodiment, the valve claspers are pushed down a predefined distance.

In one embodiment, implantation device 400 further comprises a valve stopper 450 located within and/or attached to first sheath 420. The valve stopper functions to hold the prosthetic valve in place as the valve claspers are pushed in a distal direction.

After the valve claspers are positioned in the native heart sinus, first sheath 420 is pushed down (in a distal direction, further into the left ventricle) to release support frame 440 of the valve prosthesis from the first sheath by switching first sheath switch 445 from its initial proximal position (FIG. 15B) to its distal position (FIG. 15C). Unsheathed valve support frame 470 radially expands, causing the valve claspers to clasp onto the native heart valve leaflets 490 as shown in FIG. 15C.

After ensuring the valve prosthesis is properly placed, the first sheath is pulled in a proximal direction to abut the second sheath. In one embodiment, this motion is accomplished by switching first sheath switch 445 back from its distal position to its proximal position. This is done to prepare the implantation device for retrieval. The implantation device is then gently pulled out in a proximal direction from the subject along the guidewire, which is next retrieve. The deployed heart prosthesis is held in place by the radial expansion force of valve support frame 440 and by the plurality of valve claspers 425 clasping onto the native heart valve leaflets.

XIII. An Alternative Deployment Method

Figure 30A:
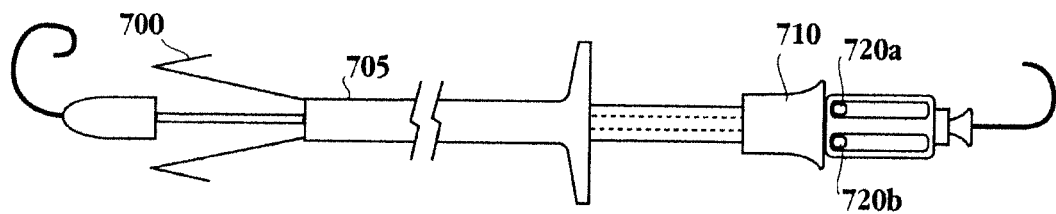
FIGS. 30A-30C illustrate an alternative embodiment for a method of delivering and deploying a valve prosthesis.
Figure 30B:
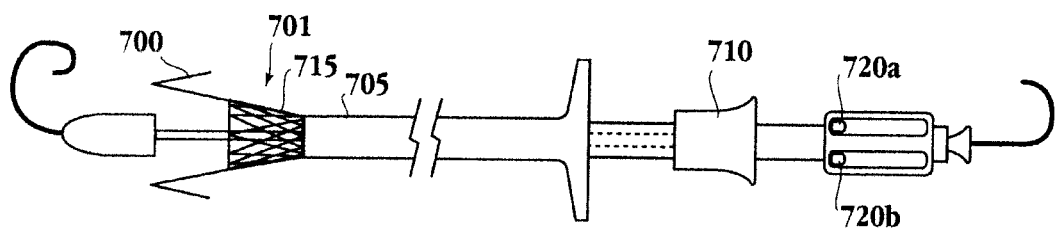
Figure 30C:
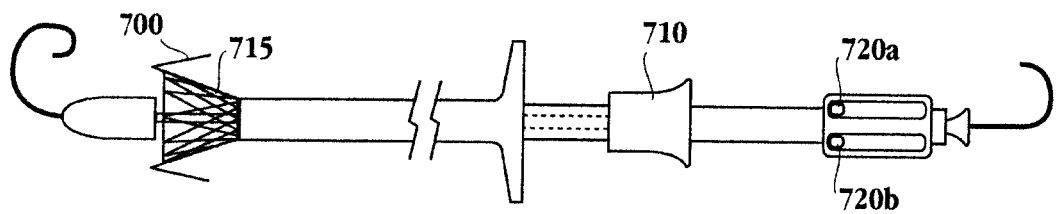

FIGS. 30A-30C depict an alternative method of releasing a valve prosthesis support frame 715 from a sheath when positioning the support frame within a native valve. As shown in FIG. 30A, valve claspers 700 are released from sheath 705. In one embodiment, the valve claspers are pushed distally from sheath 705 by pushing release buttons 720a, 720b in a distal direction.

FIG. 30B shows that only the distal portion of valve prosthesis support frame 715 has been pushed distally out of sheath 705 and only this portion has expanded. Pushing support frame 715 distally out of sheath 705 may be accomplished by pushing pusher wire controller 710 distally while holding sheath 705 stationary. This method may be accomplished using a valve prosthesis support frame as illustrated in FIGS. 1C-1D.

Sheath 705 is then pushed distally to push partially expanded support frame 715 distally to abut the apex of valve claspers 700, as shown in FIG. 30C. Note that pusher wire controller 710 can be moved at the same time.

Also noted with this embodiment, when claspers 700 are exposed, track wires which are still attached to leg members extend at an outward angle from sheath 705 as shown in FIG. 30A. Pusher wire controller 710 can then be moved in a proximal direction to uncover the distal portion of valve prosthesis support frame 715, as shown in FIG. 30B. The distal portion of support frame 715 then radially expands while the proximal portion of valve prosthesis support frame 715, remains in a compact condition within sheath 705. Pusher wire controller 710 and the first sheath are then moved in a distal direction until the distal end of the valve prosthesis abuts the clasper apex. Sheath 705 is then moved in a proximal direction to fully expose and deploy the valve prosthesis.

XIV. Delivery Device

In an eleventh aspect, a device for delivery of a medical prosthesis into a patient is provided. In one embodiment, the device for delivery of a medical prosthesis into a patient comprises a tubular steering wire extending from a distal end of the device to a proximal end of the device, a control unit at the proximal end of the device, a first sheath comprising an open lumen and positioned distally with respect to the control unit, and at least one track wire. The at least one track wire may be a solid or hollow wire or cable.

In one embodiment, the device for delivery further comprises a track wire controller. The track wire may be fixed to the track wire controller at its proximal end. In another embodiment, the track wire controller is fixed at its proximal end to a switch, dial or other movable control or member. The movable control or member may allow an operator to control the movement and/or position of the track wire independently of the device.

In one embodiment, the device further comprises a pusher wire having a proximal end fixed to the control unit and a distal end which may engage the medical prosthesis.

In one embodiment, the device further comprises a second sheath. In another embodiment, the second sheath is positioned serially with the first sheath. In one embodiment, the second sheath is positioned proximal to the first sheath. In another embodiment, the second sheath is positioned distal to the first sheath. In yet another embodiment, the second sheath is positioned concentric with the first sheath.

In one embodiment, the control unit of the device for delivery further comprises a second sheath controller. In one embodiment, the second sheath controller comprises a central control cable (second sheath control cable) that extends from the second sheath to the second sheath controller. The second sheath controller may allow the operator to move the second sheath independently of the other device components.

In one embodiment, the second sheath controller comprises the tubular steering wire secured at its distal end to the second sheath and affixed at its proximal end to the second sheath controller.

In one embodiment, the control unit of the delivery device further comprises a first sheath controller.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method for deploying a heart valve prosthesis within a native heart valve, the method comprising:
providing an implantation device and a valve prosthesis carried by the implantation device, the valve prosthesis having (i) a radially expandable support frame having an outer surface and a longitudinal axis, (ii) a plurality of flexible leaflets attached to the support frame, and (iii) a valve clasper movably coupled to the support frame to permit the valve clasper to be movable relative to the support frame along the longitudinal axis from an engagement configuration in which the valve clasper and the support frame are collapsed against the implantation device to a nesting configuration in which the support frame is positioned within the valve clasper, the implantation device having a control unit, a track wire, and first and second sheaths, the track wire having a proximal end attached to the control unit and a distal end removably coupled with the valve clasper, the first sheath encasing at least a portion of the valve clasper in a compact condition, the second sheath encasing at least a portion of the support frame, the second sheath being positioned serially to and distally from the first sheath;
inserting at least the distal end of the implantation device into a patient; and
releasing the valve prosthesis at the native heart valve.

2. The method of claim 1, wherein the native heart valve is an aortic valve, and the inserting comprises inserting the implantation device into the femoral artery and advancing the implantation device to the aortic valve.

3. The method of claim 1, wherein the native heart valve is a mitral valve, and the inserting comprises inserting the implantation device into the left ventricle.

4. The method of claim 1, further comprising proximally withdrawing the first sheath relative to the valve clasper to permit expansion of the valve clasper.

5. The method of claim 4, further comprising manipulating the track wire to advance the valve clasper into a sinus of the native heart valve.

6. The method of claim 5, further comprising detaching the track wire from the valve clasper to release the valve clasper at the native heart valve.

7. The method of claim 1, wherein the releasing comprises interposing a native heart valve leaflet between the valve clasper and the support frame.

8. A method for deploying a heart valve prosthesis within a native heart valve annulus, the method comprising:
advancing an implantation device into a patient, the implantation device carrying a radially expandable support frame of the valve prosthesis within a frame sheath of the device and a valve clasper of the valve prosthesis within an anchor sheath of the device, the valve clasper being longitudinally movably coupled to the support frame, the frame sheath being positioned serially to and distally from the anchor sheath;
moving the anchor sheath of the implantation device longitudinally relative to the valve clasper to expose at least a portion of the valve clasper;
engaging the valve clasper with the native valve annulus;
moving the frame sheath of the implantation device longitudinally relative to the support frame to permit expansion of the support frame; and
removing the implantation device from the patient.

9. The method of claim 8, wherein the moving the anchor sheath comprises proximally retracting the anchor sheath relative to the valve clasper.

10. The method of claim 8, wherein the moving the frame sheath comprises distally advancing the frame sheath relative to the support frame.

11. The method of claim 8, further comprising after engaging the valve clasper with the native valve annulus, longitudinally positioning the support frame within the valve clasper.

12. The method of claim 11, wherein the longitudinally positioning comprises proximally retracting the support frame relative to the valve clasper to position the support frame within the valve clasper.

13. The method of claim 8, wherein the moving the frame sheath comprises permitting the support frame to expand and compress against valve leaflets of the native heart valve within the valve clasper.

14. The method of claim 8, wherein the native heart valve is an aortic valve, and the advancing comprises inserting the implantation device into the femoral artery and advancing the implantation device to the aortic valve.

15. The method of claim 8, wherein the native heart valve is a mitral valve, and the advancing comprises inserting the implantation device into the left ventricle.

* * * * *